(12) United States Patent
Evans et al.

(10) Patent No.: US 7,807,075 B2
(45) Date of Patent: *Oct. 5, 2010

(54) PHOTOCHROMIC COMPOSITIONS AND LIGHT TRANSMISSIBLE ARTICLES

(75) Inventors: Richard Alexander Evans, Glen Waverley (AU); Melissa Ann Skidmore, McKinnon (AU); Lachlan Hartley Yee, Woy Woy (AU); Tracey Lee Hanley, Werombi (AU); David Andrew Lewis, Marion (AU)

(73) Assignee: Advanced Polymerik Pty Ltd, Notting Hill, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/775,328

(22) Filed: Jul. 10, 2007

(65) Prior Publication Data

US 2008/0006798 A1    Jan. 10, 2008

Related U.S. Application Data

(60) Division of application No. 11/121,293, filed on May 3, 2005, now Pat. No. 7,247,262, which is a continuation of application No. PCT/AU03/01453, filed on Nov. 3, 2003.

(30) Foreign Application Priority Data

Nov. 4, 2002  (AU)  .............................. 2002952454
Jun. 20, 2003  (AU)  .............................. 2003903133

(51) Int. Cl.
G02B 5/23  (2006.01)
(52) U.S. Cl. ........................ 252/586; 252/582; 359/326; 549/331; 549/381
(58) Field of Classification Search .................. 252/582, 252/586; 524/89; 544/99; 526/260; 359/326; 549/31, 381

See application file for complete search history.

(56) References Cited

U.S. PATENT DOCUMENTS

| 2,370,567 | A |   | 2/1945  | Muskat et al. |
| 2,403,113 | A |   | 7/1946  | Muskat et al. |
| 2,918,972 | A |   | 12/1959 | Tubbs |
| 3,918,972 | A |   | 11/1975 | Evens et al. |
| 4,062,865 | A |   | 12/1977 | Moggi |
| 4,220,708 | A |   | 9/1980  | Heller |
| 4,286,957 | A |   | 9/1981  | Le Naour-Sene |
| 4,454,219 | A |   | 6/1984  | Yamadera et al. |
| 4,880,667 | A |   | 11/1989 | Welch |
| 5,322,945 | A |   | 6/1994  | Krongauz et al. |
| 5,383,959 | A | * | 1/1995  | Sirdesai et al. ........... 106/31.21 |
| 5,589,306 | A |   | 12/1996 | Takahashi et al. |
| 5,623,040 | A |   | 4/1997  | Fischer et al. |
| 5,683,628 | A |   | 11/1997 | Mizuno et al. |
| 5,776,376 | A |   | 7/1998  | Nagoh et al. |
| 5,821,287 | A |   | 10/1998 | Hu et al. |
| 6,113,814 | A |   | 9/2000  | Gemert et al. |
| 6,133,390 | A |   | 10/2000 | Kozlovski et al. |
| 6,316,569 | B1 |   | 11/2001 | Henry et al. |
| 6,362,248 | B1 |   | 3/2002  | Hara et al. |
| 6,733,689 | B1 | * | 5/2004  | Meyer et al. ........... 252/299.01 |
| 2001/0025948 | A1 |   | 10/2001 | Walters et al. |
| 2003/0043447 | A1 |   | 3/2003  | Toh et al. |
| 2003/0099910 | A1 |   | 5/2003  | Kim et al. |
| 2003/0141490 | A1 |   | 7/2003  | Walters et al. |
| 2005/0004361 | A1 |   | 1/2005  | Kumar et al. |
| 2005/0254003 | A1 |   | 11/2005 | Jani et al. |

FOREIGN PATENT DOCUMENTS

| EP | 277639          |   | 8/1988  |
| EP | 1119 572        |   | 8/2001  |
| JP | 63-250381       |   | 4/1990  |
| JP | 03-091578       |   | 4/1991  |
| JP | 02-042084       |   | 10/1991 |
| JP | 07-134356       | * | 5/1995  |
| WO | WO 97/00523     |   | 1/1997  |
| WO | WO97/05213      | * | 2/1997  |
| WO | WO 97/05213 A1  |   | 2/1997  |
| WO | WO 00/05325     |   | 2/2000  |
| WO | WO 00/15629     |   | 3/2000  |
| WO | WO 00/15629 A1  |   | 3/2000  |
| WO | WO 00/21968     |   | 4/2000  |
| WO | WO 01/70719     |   | 9/2001  |
| WO | WO 01/70719 A2  |   | 9/2001  |
| WO | WO 2004/041961 A1 |   | 5/2004 |

OTHER PUBLICATIONS

Didier Gaude, et al., Photochromism of Spiropyrans Study of the Degradation of Substituted and Polymeric Indoline Derivatives, Journal of the French Chemistry Society (1979), No. 9-10, France.
Christian Goett, et al., Synthese et etude de Copolymeres Sequences Photochromiques, Book, (1979), Promol. Chem. 180, pp. 1865-1875, France.
Kobunshi Ronbunshu, Living Polymer Employed High Molecule Spiropyran Synthesis and its Nature, Japanese Journal of Polymer Science and Technology, (1974), pp. 551-557, vol. 31, No. 9, Japan.

* cited by examiner

Primary Examiner—Ling-Siu Choi
Assistant Examiner—Bijan Ahvazi
(74) Attorney, Agent, or Firm—Smith, Gambrell & Russell, LLP

(57) ABSTRACT

The invention relates to a photochromic polymeric composition comprising a polymer matrix and a photochromic compound which is an adduct comprising a photochromic moiety and at least one pendant oligomer group to provide a rate of fade of the photochromic polymeric composition which is significantly changed when compared with the corresponding composition comprising the photochromic compound without said pendent oligomer.

The invention also relates to a photochromic compound which is an adduct comprising a photochromic moiety and at least one pendent oligomer.

22 Claims, 14 Drawing Sheets

Figure 5

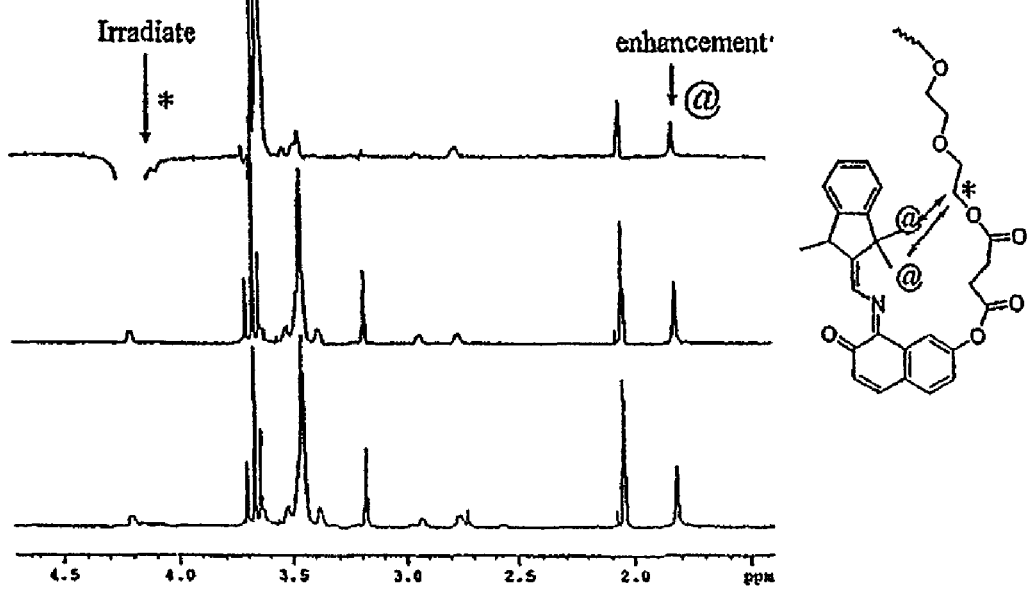

ROE experiment of Example 1 showing nanoencapsulation of coloured form in acetone-$d_6$ Irradiate ↓ *   enhancement ↓ @

ROE NMR experiment. Evidence of Nano solvation/encapsulation of Example 5. Interaction of PDMS oligomer with central H of coloured form of Spirooxazine in acetone-$d_6$

Figure 6

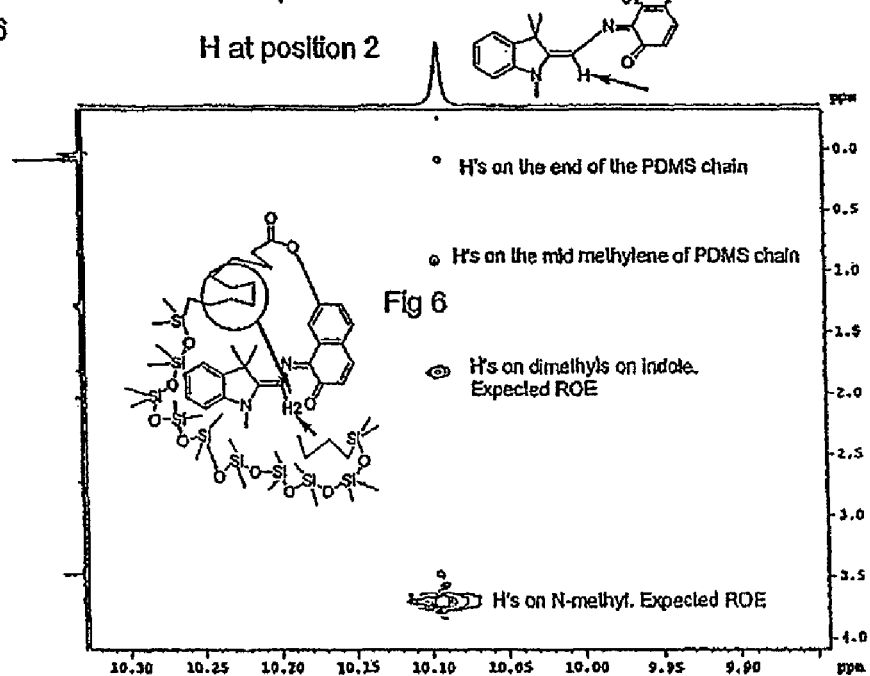

H at position 2

° H's on the end of the PDMS chain
◦ H's on the mid methylene of PDMS chain
◉ H's on dimethyls on indole. Expected ROE
H's on N-methyl. Expected ROE ROE NMR experiment. Evidence of Nano solvation/encapsulation of example 5. Interaction of PDMS oligomer with Indole H4 of coloured form of Spirooxazine in acetone-$d_6$.

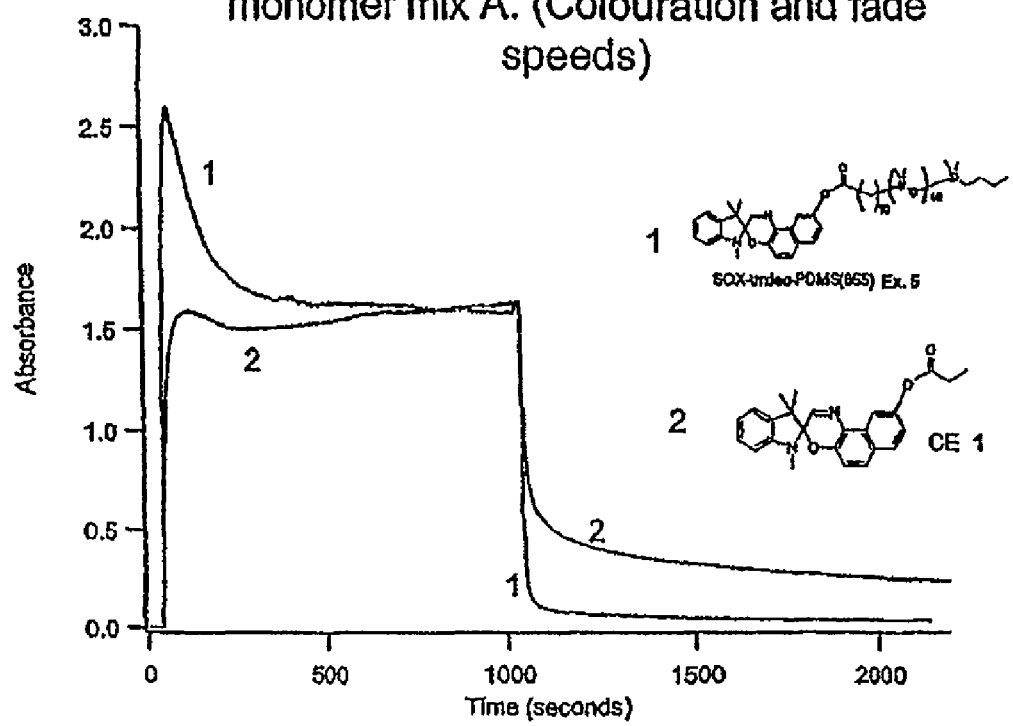
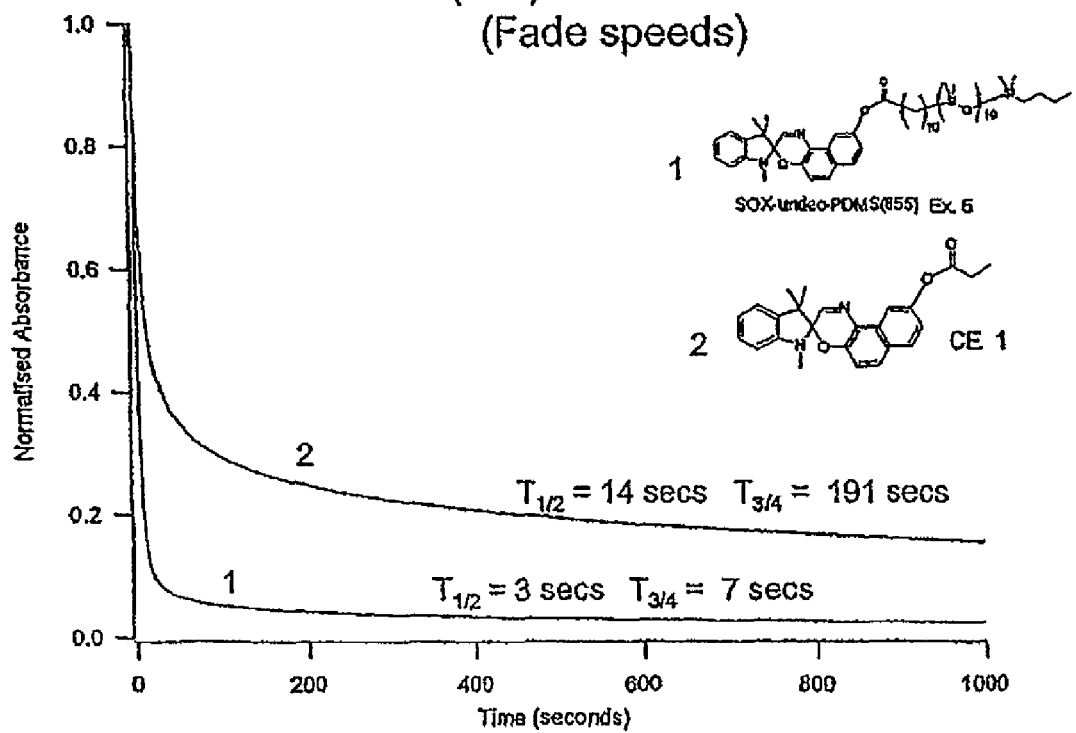

Chromene Ex 16 cast in monomer mix A, I (Colouration and fade speeds)

Chromene Ex. 16 cast in monomer mix A, II (Fade speeds)

Ex 20 in monomer mix A, I. (Colouration and fade speeds)

Ex 20 in monomer mix A, II. (Fade speed)

Dyes Ex. 5 and CE3 cast in monomer mix A. Oligomer must be attached to the dye for fast colouration and fade speeds.

Dyes Ex. 5 and CE3 cast in monomer mix A. Low Tg oligomer must be attached to the dye for fast colouration and fade speeds.

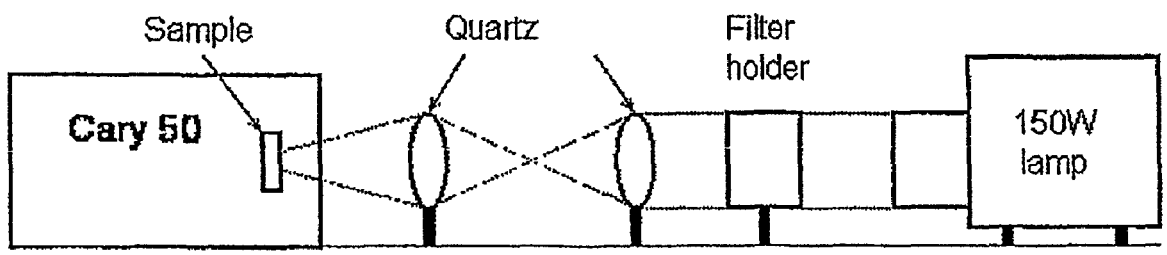
Figure 17 Instrumental setup for irradiation and absorption measurements of photochromic samples. A number of filters can be integrated into the system to select for ranges of wavelengths exciting the sample. Equally, a monochromator can also be incorporated between the 2 lenses to select for wavelength.

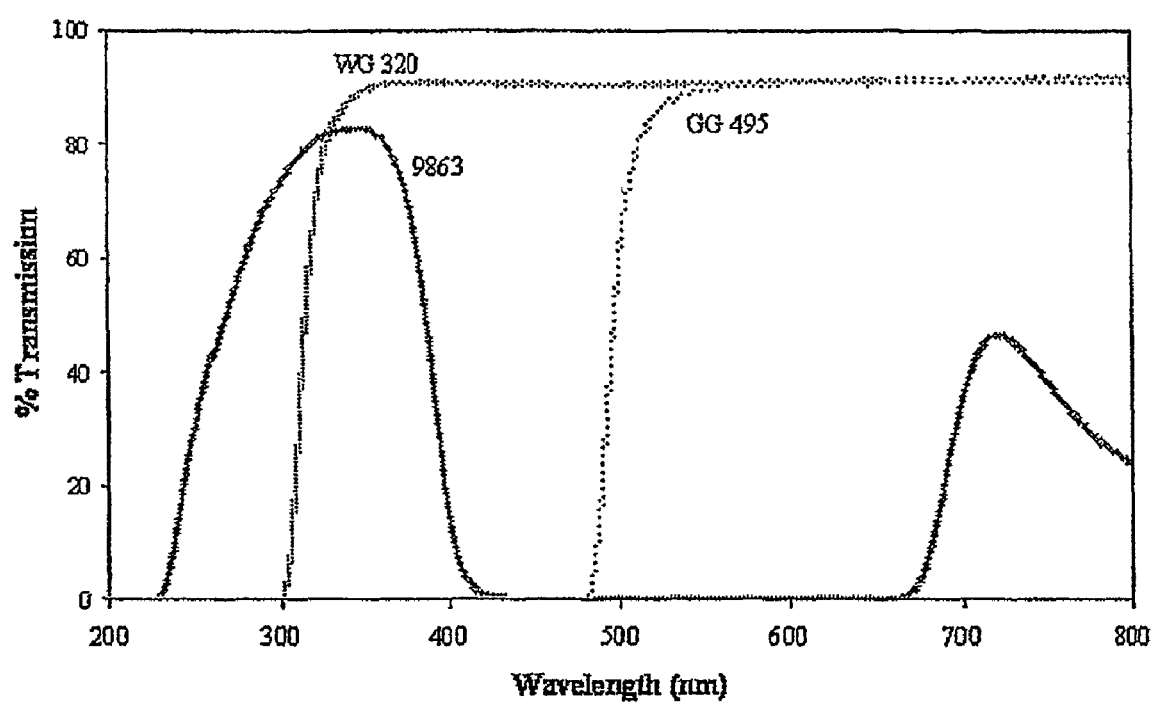
Figure 18: Transmission spectra of the filters employed in the experimental setup.

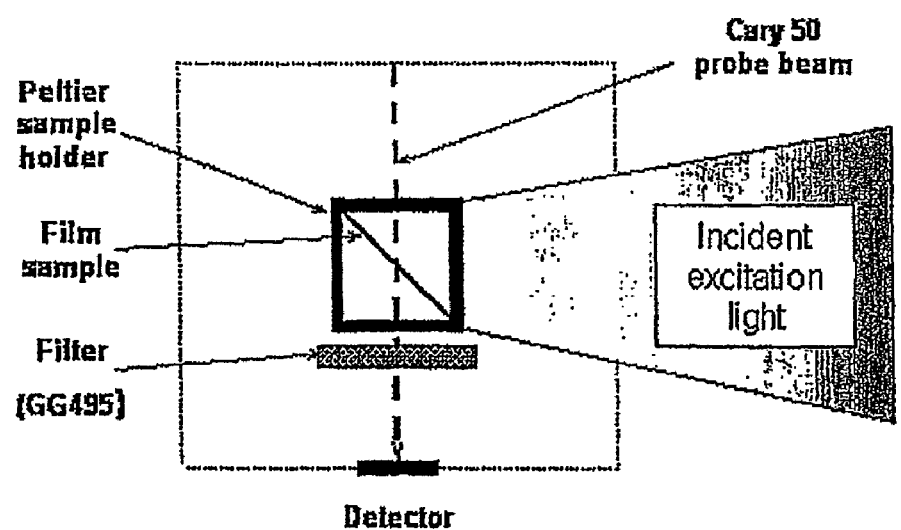
*Figure 19:* Top view of the Cary 50 sample holder and experimental setup geometries for films.

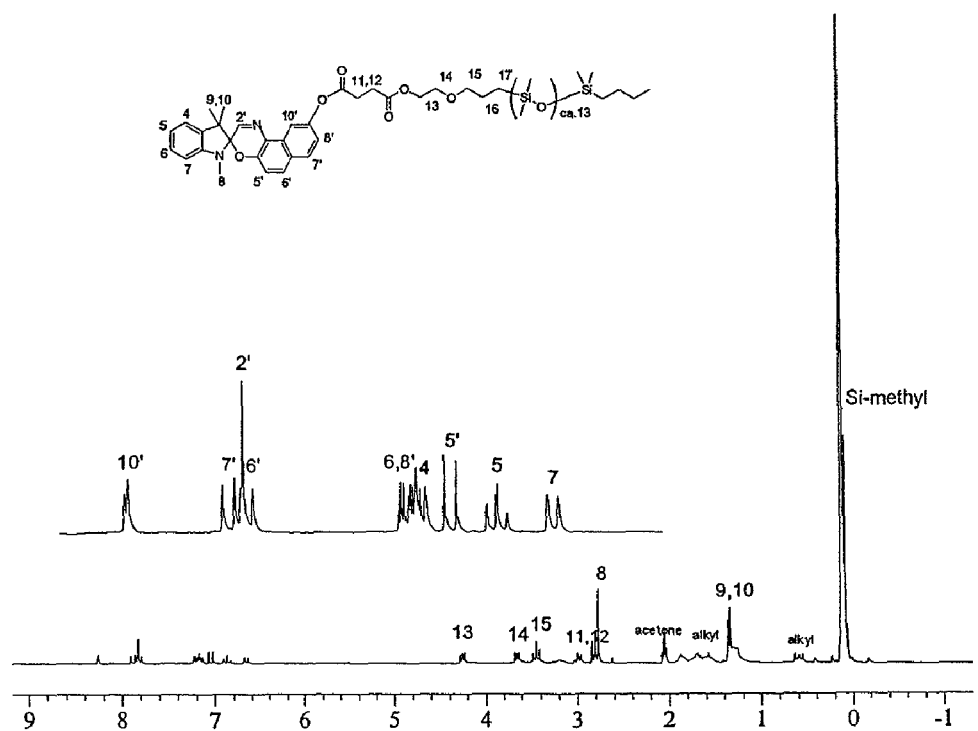
Figure 20 for Example 18
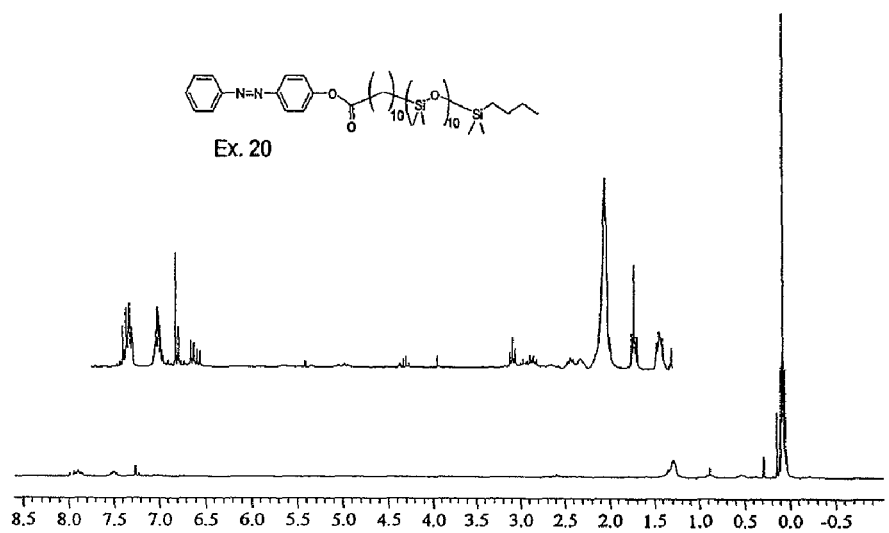
Figure 21 for Example 20

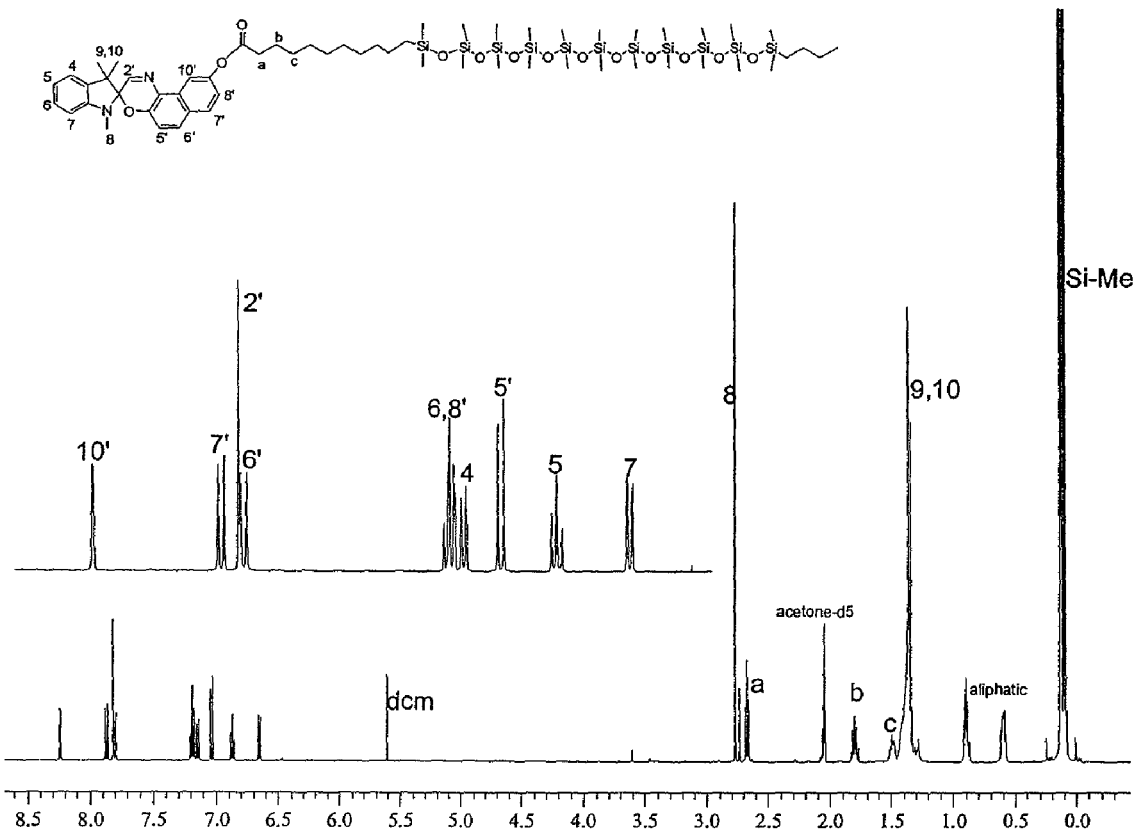
Figure 22 for Example 5

PHOTOCHROMIC COMPOSITIONS AND LIGHT TRANSMISSIBLE ARTICLES

REFERENCE TO RELATED APPLICATIONS

This application is a divisional application of our U.S. patent application Ser. No. 11/121,293 filed May 3, 2005, now U.S. Pat. No. 7,247,262 which in turn is a continuation of PCT Application Number PCT/AU2003/001453 filed Nov. 3, 2003, which claims priority to Australian Patent Application Number 2002952454 filed Nov. 2, 2002, and Australian Patent Application Number 2003903133 filed Jun. 20, 2003, all of which are relied on and incorporated herein by reference.

FIELD

The present invention relates to a class of functionalised photochromic dyes, to compositions containing the functionalised dyes, and to a method for forming polymeric compositions and light transmissible polymeric articles exhibiting photochromic response.

BACKGROUND

Photochromism is a property which has been used in the manufacture of light transmissible articles for many years. A compound is said to be photochromic if it changes colour when irradiated and reverts to its original colour when irradiation ceases. The use of photochromics in the manufacture of spectacle lenses is a particular benefit as it enables the efficiency with which radiation is filtered to be varied with the intensity of radiation. Photochromics also have potential for use in a range of other polymeric compositions in products or in applications such as windows, automotive windshields, automotive and aircraft transparencies, polymeric films coating compositions, optical switches and data storage devices. Photochromics could also be used in inks and to improve the security of documents and currency, for example by providing a security check under UV light or by indicating exposure to light during photocopying.

Despite the use of photochromic compounds in applications such as lenses there have been a number of problems which reduce the versatility and potential of this technology.

It is advantageous to control the rate at which photochromic polymeric compositions colour when exposed to radiation and fade on cessation of this exposure. In many situations, it is important to provide rapid colouring and fading kinetics, particularly for lenses and spectacles. In some polymers however, the rate of coloration and fade is slow so that a compromise needs to be made in the components and properties of the substrate to enhance the rate of coloration and fade. For example, many photochromics colour and fade more rapidly in soft materials and yet, for applications such as spectacles or structural panels, abrasion resistance and hardness are important. This trade off between rate of transformation and hardness produces a dilemma for manufacturers between toughness and photochromic efficiency. In polymeric lenses many photochromics exhibit a slower rate of fade than is desirable. It would be desirable to have photochromic dyes which fade rapidly regardless of the hardness of the matrix.

One approach taken by previous workers is to produce photochromics which are an integral part of the host matrix. This is achieved by functionalising the photochromic with an unsaturated group which is polymerised with the polymer matrix. The photochromic thus becomes covalently tethered to the host polymer matrix. However unless the matrix is relatively soft the rate of fade is adversely effected. Hu et al, *Pure Appln. Chem.*, AA(6) pp 803-810 (1996) also reported that tethering of the photochromic leads to the decolouration rate remaining almost constant with increasing dye concentration. Further the fade observed is significantly slower when this photochromic is tethered at concentrations less than 15 wt %.

Another example of cases where control of fade is desirable is with the a mixture of photochromic compounds. It is sometimes necessary to use a mixture of photochromic compounds to achieve the desirable colour such as brown or grey. However, the different photochromic dyes used in combination to achieve these colours often differ slightly in the rate of fade so that the mixture undergoes an unattractive variation in colour during fade. In other cases it may be desirable to reduce the rate of fade so that colouration or fade is gradual and controlled. For example in optical switches it may be desirable for the photochromic article to undergo rapid switching under specific thermal or electromagnetic stimulus but otherwise not fade under the ambient conditions of temperature and light.

Another problem associated with photochromic compounds is their lifetime. Many photochromic compounds have a relatively short lifetime before they fatigue, due to chemical degradation, and either no longer undergo reversible colour change or become less efficient. This is a problem, for example, in more hostile chemical environments such as in high index lenses containing sulfur-containing polymers or paper.

SUMMARY

We have now found that the photochromic properties of photochromic dyes in a polymeric substrate can be controlled by using a photochromic compound in which the photochromic moiety is functionalised to contain one or more pendant oligomer groups. Without wishing to be bound by theory we believe that certain oligomer groups provide a nanoenvironment to produce a significant change in the rate of fade. The one or more pendant oligomer groups change the rate of fade of the photochromic moiety in the polymeric matrix.

In one aspect the invention provides a photochromic polymeric composition comprising a polymer matrix and a photochromic compound which is an adduct comprising a photochromic moiety and at least one pendant oligomer group to provide a rate of fade of the photochromic polymeric composition which is significantly changed when compared with the corresponding composition comprising the photochromic compound without said pendent oligomer.

The oligomer is preferably not reactive the host matrix so that it does not become covalently tethered to the matrix polymer.

In a further aspect the invention provides a photochromic compound which is an adduct comprising a photochromic moiety and at least one pendant oligomer.

In the preferred embodiment of the invention the oligomer significantly increases the rate of fade so that the fade half life and/or the time taken to reach ¾ reduction in absorbance is reduced by at least 50% compared with the corresponding composition in absence of the oligomer.

DETAILED DESCRIPTION

In a rigid polymeric material of high glass transition temperature (Tg) the photochromic action of many photochromic compounds is reduced significantly when compared with softer materials. Without wishing to the bound by theory, we believe that the reduction in photochromic performance in polymeric substrates may occur as a result of the restriction in the volume available for the dye to transform by ring opening and/or effects of polar interaction.

One possible explanation of the more rapid transition observed for many compounds of the invention is that the oligomer chain may coil about the photochromic group to provide nanoencapsulation facilitating more rapid conversion between ring-open and ring-closed forms. The oligomer chains may provide a low Tg nanoenvironment or otherwise favourably alter the local environment. Accordingly it is preferred that the oligomer attached to the photochromic compound of the invention has a relatively low Tg. For example the Tg is preferably less than 25° C. More preferably the compounds of the invention are liquids at room temperature.

The compatibility of the oligomer chain with the host matrix may also influence the rate of fade.

The rate of fade of a photochromic chromophore may be slowed by using a plurality of oligomer substituents including a first oligomer chain and a second oligomer chain each on opposite sides of the photochromic moiety (such as spirooxazine group). This trend is especially the case as the Tg of the oligomers increases or they become more compatible with the host matrix. For example, in the case of Spiro indolene aryleneoxazine compounds, one oligomer may be attached to fused benzene ring of the indolene portion and one oligomer chain attached to the aryl portion fused with the oxazine. When the oligomer chains are each compatible with the host matrix they may restrict motion of the photochromic moiety by becoming included into the matrix and restricting opposite ends of the spiro-oxazine. Fade speed may also be slowed by a single oligomer of relatively high Tg.

The trend in compatibility of an oligomer with the polymer matrix in many cases is consistent with polarity. Thus, an oligomer of similar polarity to the first polymer matrix is regarded as compatible. For example polyalkylene glycol oligomer groups are compatible with polar polymeric hosts such as acrylate and polyalkylene and poly(arylalkylene) oligomers are compatible with non-polar resins such as polyolefins and styrenic polymers (eg polystyrene, SBR etc) respectively.

We have also found that the nanoenvironment provided by the presence of one or more oligomer chains significantly improves the photochromic life of compounds of the invention when compared with unsubstituted photochromic compounds.

The invention relates to photochromic compounds comprising a photochromic moiety and at least one pendant oligomer group. Said at least one oligomer may be selected from the group consisting of polyether oligomers, polyalkylene oligomers, polyfluoroalkylene oligomers, poly fluoroalkylether oligomers, polydi($C_1$ to $C_{10}$ hydrocarbyl)silyloxy oligomers, polysilicic acid oligomers (silicates) or derivatives thereof, poly (ZSi(OH)$_3$) oligomers and derivatives thereof, poly (ZSiCl$_3$) oligomers and derivatives thereof, poly (ZSi(OMe)$_3$) oligomers and derivatives thereof, and mixtures thereof wherein Z is an organic group. Preferably Z is selected from the group consisting of hydrogen, alkyl, optionally substituted alkyl, haloalkyl, cycloalkyl, optionally substituted cycloalkyl, hydroxy, amino, optionally substituted amino, alkoxy, aryloxy, aryl, optionally substituted aryl, carboxylic acid and derivatives thereof. A particularly preferred subset of these later oligomers are colloquially known as Polyhedral Oligomeric Silsesquioxanes (POSS). Compounds that contain a photochromic moiety and a POSS oligomer can display crystalline state photochromism.

The combined number of monomer units in the oligomers is preferably at least 5 and more preferably at least 7 and still more preferably at least 10. The oligomer and any group linking the oligomer to the chromophore preferably together provide a longest chain length of at least 12 atoms in the backbone of the chain, more preferably at least 15 atoms and most preferably at least 17 atoms.

The modified photochromics of the invention generally are of formula I

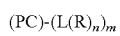

wherein

PC is the photochromic moiety;

L is a bond or linking group;

R is an oligomer chain;

n is an integer of from 1 to 3;

m is an integer of from 1 to 3 and wherein the total number of monomer units in the oligomer groups (R) is at least 5, preferably at least 7, more preferably at least 10. It is particularly preferred that the linking group (when present) and the oligomer [ie. the radical .L(R)n)$_m$] together provide a longest chain length of at least 12 atoms, more preferably at least 15 atoms and most preferably 17 to 40 atoms in the chain backbone.

Examples of suitable oligomer groups R include groups of formula Ia:

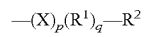

wherein:

X is selected from oxygen, sulfur, amino such as $C_1$ and $C_6$ alkyl amino, $C_1$ to $C_4$ alkylene (preferably methylene);

p is 0 or 1;

q is the number of the monomer units $R^1$ in said oligomer and is preferably at least 5;

$R^1$, which may be the same or different, are selected from the group consisting of:

$C_2$ to $C_4$ alkylene such as ethylene, propylene and butylene;

halo ($C_2$ to $C_4$ alkylene) such as perfluoroethylene, perfluoropropylene, and perfluorobutylene;

$C_2$ to $C_4$ alkyleneoxy;

$C_2$ to $C_4$ haloalkyleneoxy;

di ($C_1$ to $C_{10}$ hydrocarbyl)silyloxy wherein the hydrocarbyl may be alkyl, aryl alkyl substituted aryl or aryl substituted alkyl and particularly di($C_1$ to $C_4$ alkyl)silyloxy such as dimethylsilyloxy; and $R^2$ is selected from hydrogen, $C_1$ to $O_6$ alkyl and $C_1$ to $C_6$ haloalkyl, hydroxy, optionally substituted amino, optionally substituted aryl carboxylic acid and derivatives thereof and preferably $R^2$ is selected from the group consisting of hydrogen, $C_1$ to $C_6$ alkyl, substituted amino, optionally substituted aryl and alkyl and aryl esters of carboxyl.

Examples of suitable oligomer group R also include groups of formula 1B or 1C

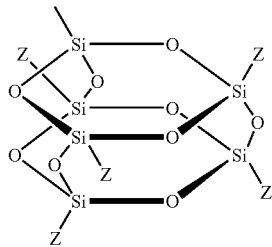
1B

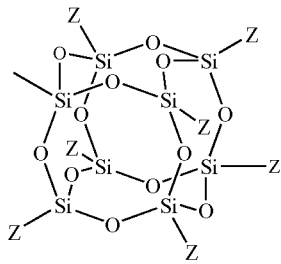
1C wherein Z is an organic group, preferably an organic group selected from the group consisting of hydrogen, alkyl, optionally substituted alkyl, haloalkyl, cycloalkyl, optionally substituted cycloalkyl, hydroxy, amino, optionally substituted amino, alkoxy, aryloxy, aryl, optionally substituted aryl, carboxylic acid and derivatives thereof. It is particularly preferred that Z is selected from the group consisting of isobutyl, iso-ocytl, cyclopentenyl, cyclohexyl and phenyl.

The oligomer group preferably does not contain groups which undergo radical or condensation reactions. Thus the oligomer will generally not have a terminal unsaturated group or terminal activated hydrogen such as amino hydroxyl or carboxyl.

Preferably L is selected from the group consisting of a bond or the polyradical selected from the group of formula IIa, IIb, IIc, IId, IIe, IIf, IIg, III, IIi, IIj and IIk.

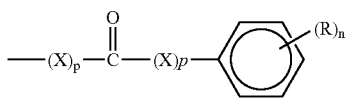
IIa wherein n is from 1 to 3;

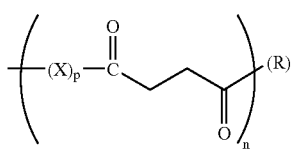
IIb

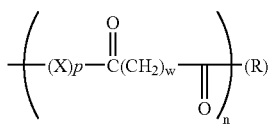
IIc

IId

IIe

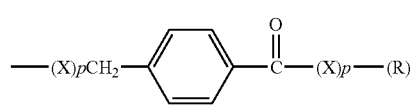
IIf

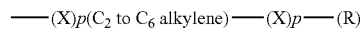
IIg

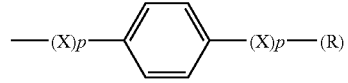
IIh

IIi

IIj

IIk

wherein in the formula IIa to IIk:
X which may be the same or different is as hereinbefore defined;
$R^4$ is selected from the group consisting of hydroxy, alkoxy, amino and substituted amino such as alkyl amino;
n is an integer from 1 to 3;
w is an integer from 1 to 4;
q is an integer from 0 to 15;
p which when there is more than one may be the same or different is 0 or 1; and
(R) shows the radial for attachment of oligomer R.

The purpose of the linking group is to join the oligomer(s) to the photochromic moiety. A linking group may be needed when the oligomer has a functional group that cannot be used directly to join to the dye. For example the terminal hydroxyl of a PEG oligomer can be converted to an acid by reaction with succinic anhydride. This could then be readily joined to the hydroxy group on a photochromic moiety such as 9'-hydroxy-1,3,3-trimethylspiro[indoline-2,3'-93H]naphtha[2,1-b][1,4]oxazine]. Another example is in Example 16 where the carboxylic acid on the chromene was esterified with ethylene glycol to provide a hydroxy group that can react with the acid group (via the acid chloride) of the poly(dimethylsiloxane) monocarboxydecyl chloride.

The linking group may in some case be available as part of the oligomer. For example in the examples we demonstrate the use of poly(dimethylsiloxane) monocarboxydecyl chloride. The undecyl carboxy group is part of the commercially available oligomer MCR-B11 and acts as the linking group between the dye and the oligomer.

Specific examples of linker groups L include:

(i) a bond (ii) 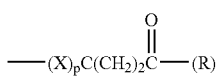

(iii) 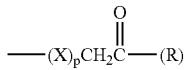

(iv) 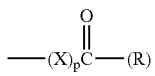

(v) 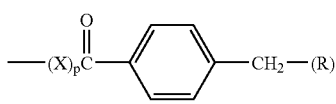

(vi) 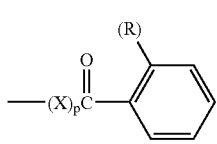

(vii) 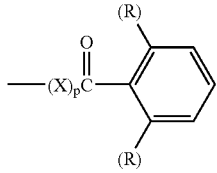

(viii) 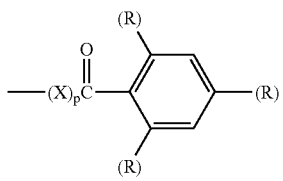

(ix) 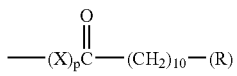

(x) 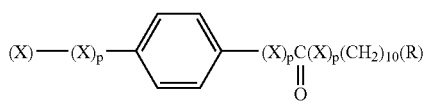

(xi) 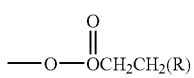

(xii) 

The compounds of the present invention comprise oligomer groups wherein the total number of monomeric units is as least 5, preferably at least 7, and most preferably at least 10. The oligomer chain and linking group preferably provide a longest chain length of at least 12 atoms, more preferably at least 15 atoms and most preferably from 17 to 40 atoms. The chain length we refer to here is the number of atoms linked in sequence in the polymer backbone.

The oligomer(s) may be in the form of linear chains, branched chains, copolymers including block or random copolymers; however, it is particularly preferred that each oligomer comprise at east 5 monomer units of the same type, and more preferably at least 7.

Preferably, the monomer units are selected from the groups consisting of perfluruoalkylene, alkylene, arylalkylene, alkyleneoxy, haloalkyleneoxy, and di($C_1$ to $C_{10}$ hydrocarbyl)silyloxy. More preferred monomer units are alkyleneoxy, and dialkylsilyloxy and even more preferred are ethyleneoxy, propyleneoxy and random and block copolymers thereof.

The photochromic compound of the invention of formula I includes up to three groups each of which may include one, two or three oligomer groups R.

Examples of preferred oligomer groups include:

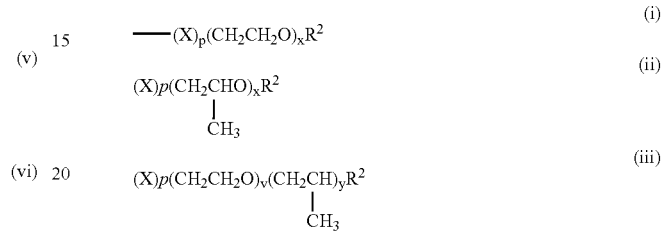

(i), (ii), (iii)

wherein the monomer units are distributed randomly or in block form

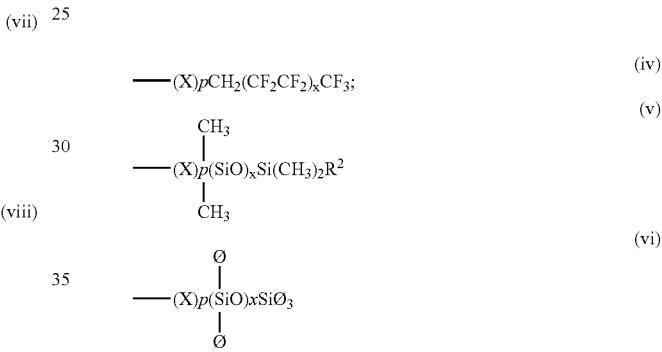

(iv), (v), (vi)

wherein ø is alkyl or aryl and includes at least a portion of aryl groups $$Xp(CF_2CF_2O)x\text{-}(CF_2)nCF_3 \qquad (vii)$$

wherein X and $R^2$ and p are hereinbefore defined and x, v and y are the number of repeating units, and alkyl is $C_1$ to $C_{20}$ alkyl, preferably $C_1$ to $C_{10}$ alkyl such as methyl, ethyl, propyl, butyl, pentyl or hexyl. Preferably the compounds of the invention include at least one oligomer group wherein the number of monomer units (x or y+v in the above examples) is at least 7 and are most preferably at least 10.

A further preferred oligomer group is a group of formula:

1C

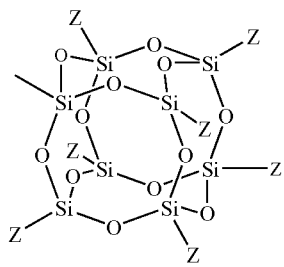

wherein Z is an organic group, preferably an organic group selected from the group consisting of hydrogen, alkyl, optionally substituted alkyl, haloalkyl, cycloalkyl, optionally substituted cycloalkyl, hydroxy, amino, optionally substituted amino, alkoxy, aryloxy, aryl, optionally substituted aryl, carboxylic acid and derivatives thereof. It is particularly preferred that Z is selected from the group consisting of isobutyl, iso-ocytl, cyclopentenyl, cyclohexyl and phenyl.

The most preferred oligomer groups contain at least 10 monomer units. The monomer units may be up to thirty or more units in length but we have found the range of from 10 to 30 to be particularly suitable.

It will be appreciated by those skilled in the art that the presence and nature of the group X is dependent on the linker group. When the linker group is a bond and the oligomer is linked to a heteroatom such as nitrogen, then p is preferably zero.

However, when the group $L\text{-}(R)_n$ is attached to a carbon radical of the photochromic moiety, or a linker of formula IIa to IIk then in the oligomer group R the integer, p is preferably 1.

The photochromic moiety may be chosen from a wide range of photochromic moieties known in the art. The most appropriate photochromic moieties for use in the compounds used in accordance with the invention are photochromics which undergo a molecular isomerism such as a cis-trans isomerism or pericyclic reaction such as 6π, −6 atom, 6π, −5 atom processes and [2+2],[4+4] or [4+2]cycloadditions. The compositions of the invention (and in particular the oligomer chains) are believed to provide a nanoenvironment to provide a desired environment which may lead to a more rapid transformation between the colour-producing chromophore and colourless state of the photochromics.

Photochromic oligomer adducts in accordance with the invention may comprise a photochromic moiety selected from the group consisting of:
chromenes such as those selected from the group consisting of naphthopyrans, benzopyrans, indenonaphthopyrans and phenanthropyrans;
spiropyrans such as those selected from the group consisting of spiro(benzindoline) naphthopyrans, spiro(indoline)benzopyrans, spiro(indoline)naphthopyrans, spiroquinopyrans, and spiro(indoline)pyrans and spirodihydroindolizines;
spiro-oxazines such as those selected from the group consisting of spiro(indoline)naphthoxazines, spiro(indoline)pyridobenzoxazines, spiro(benzindoline)pyridobenzoxazines, spiro(benzindoline)naphthoxazines and spiro(indoline)-benzoxazines;
fulgidies, fulgimides;
anils;
perimidinespirocyclohexadienones;
stilbenes;
thioindigoids;
azo dyes; and
diarylethenes.

Examples of photochromic moieties may be selected from the group consisting of fulgide photochromic compounds, chromene photochromic compounds and spiro-oxazine photochromic compounds. A wide range of photochromic compounds of each of the classes referred to above have been described in the prior art and having regard to the teaching herein the skilled addressee will have no difficulty in preparing a wide range of photochromic oligomer adducts. Examples of chromene photochromic compounds, fulgide photochromic compounds and spiro-oxazine photochromic compounds are described in U.S. Pat. No. 5,776,376.

The most preferred photochromic compounds are the chromenes and spirooxazines, specifically spiroindolene aroxazines.

Sprio-oxazines such as sprioindoline naphthoxazines depicted below are clear but in the presence of light undergo ring opening to give a coloured form as shown:

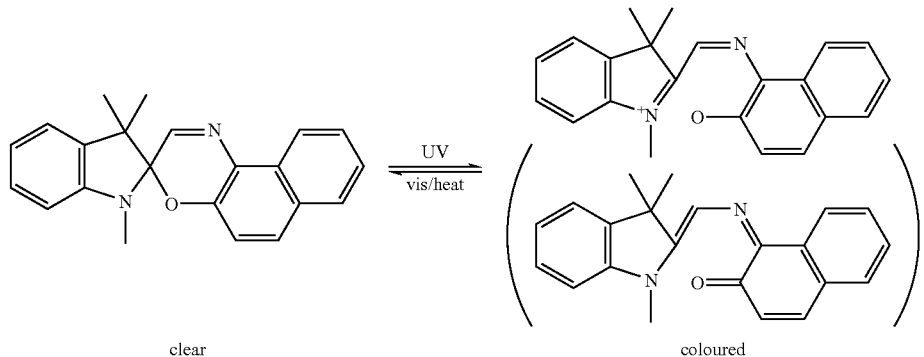

clear          coloured

A further embodiment of the invention is a photochromic compound of formula

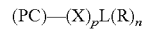

wherein PC is a photochromic moiety particularly a spirooxazine of formula III, chromene of formula XX, fulgideffulgamide of formula XXX or an azo dye of formula XL and L, R, X and n and p are as hereinbefore defined. Formulae III, XX, XXX and XL are described below with reference to examples.

Preferred spiro-oxazines of the general formula III can be suitably used.

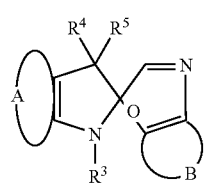

III

In the general formula III, $R^3$, $R^4$ and $R^5$ may be the same or different and are each an alkyl group, a cycloalkyl group, a cycloarylalkyl group, an alkoxy group, an alklyleneoxyalkyl group, an alkoxycarbonyl group, a cyano, an alkoxycarbonylalkyl group, an aryl group, an arylalkyl group, an aryloxy group, an alkylenethioalkyl group, an acyl group, an acyloxy group or an amino group, $R^4$ and $R^5$ may together form a ring, and $R^3$, $R^4$ and $R^5$ may optionally each have a substituent(s). The substituent(s) can includes (include), besides the above-mentioned groups, halogen atom, nitro group, heterocyclic group, etc. The group represented by moiety IIIa

IIIa is a substituted or unsubstituted bivalent aromatic hydrocarbon group or a substituted or unsubstituted bivalent unsaturated heterocyclic group. The group represented by moiety IIIb

IIIb is a substituted or unsubstituted bivalent aromatic hydrocarbon group or a substituted or unsubstituted bivalent unsaturated heterocyclic group. Specific examples of the bivalent aromatic hydrocarbon group are groups of 6 to 14 carbon atoms derived from benzene ring, naphthalene ring, phenanthrene ring, anthracene ring or the like. Specific examples of the bivalent unsaturated heterocyclic group are groups of 4 to 9 carbon atoms derived from furan ring, benzofuran ring, pyridine ring, quinoline ring, isoquinoline ring, pyrrole ring, thiophene ring, thiophene ring, benzothiophene ring or the like.

The substituents can be the same groups as mentioned above with respect to $R^3$, $R^4$ and $R^5$. In particular, a group represented by

—$NR^6R^7$ (wherein $R^6$ and $R^7$ are each an alkyl group, an alkoxy group, an allyl group or the like, each of which may be substituted; and $R^6$ and $R^7$ may be bonded and cyclized with each other to form a nitrogen-containing heterocyclic ring) is preferable from the standpoint of high density of its developed colour in the initial photochromic performance.

In a particularly preferred embodiment the photochromic compounds of the invention are of formula IV

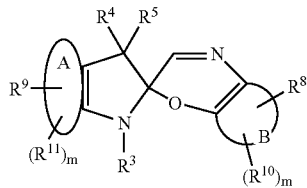
IV wherein $R^3$, $R^4$, $R^5$, $R^8$, $R^9$, $R^{10}$ and $R^{11}$ are independently selected from the group consisting of hydrogen, alkyl, halo, haloalkyl, cycloalkyl, cycloarylalkyl, hydroxy, alkoxy, alkyleneoxyalkyl, alkoxycarbonyl, aryl, arylalkyl, aryloxy, alkylenethioalkyl, acyl, acyloxy, amino, $NR^6R^7$, cyano and the group $L(R)_n$ wherein at least one of $R^3$, $R^8$ and $R^9$ is the oligomer group of formula $L(R)_n$ wherein L, R and n are hereinbefore defined and wherein there is more than one $L(R)_n$ group in the groups $R^8$, $R^3$, $R^4$ and $R^5$ and one or more R groups may optionally be linked together to form one or more bridging oligomers. The subscript m is an integer and may be 0, 1 or 2 wherein m is 2 the groups may be independently selected.

In the compound of formula IV the total of the number of monomer units in oligomer substituents, $(R)_n$, is at least 7 and preferably at least 12.

More preferably, the substituents $R^3$ is selected from the group consisting of alkyl, cycloalkyl, cycloarylalkyl, alkyleneoxyalkyl, aryl, arylalkyl alkylenethioalkyl, and the group $L(R)_n$ and more preferably $R^3$ is selected from alkyl, cycloalkyl, cycloarylalkyl, alkenyloxyalkyl, aryl, arylalkyl, and the group $L(R)_n$ and preferably $R^4$ and $R^5$ are indefinitely selected from alkyl, cycloalkyl and aryl.

$R^8$ and $R^9$ are independently selected from hydrogen and $L(R)_n$; $R^{10}$ and $R^{11}$ are independently selected from the group consisting alkyl, cycloalkyl, cycloarylalkyl, alkoxy, —$NR^6R^7$, cyano, alkyleneoxyalkyl, alkoxycarbonyl, aryl, arylalkyl, aryloxy, alkylenethioalkyl, aryl aryloxy and amino and most preferably $R^{10}$ and $R^{11}$ are independently selected from alkyl, cycloalkyl, alkoxy, $NR^6R^7$ and cyano; and m is 0 or 1.

Examples of the preferred fused aromatic ring groups of formula IIIa include IIIa(i);

IIIa(i)

wherein $R^9$ and $R^{11}$ are as hereinbefore defined.

Examples of the preferred fused aromatic ring group of formula IIIb include IIIb(i), IIIb(ii), IIIb(iii) and IIIb(iv).

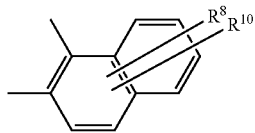

IIIb(i)

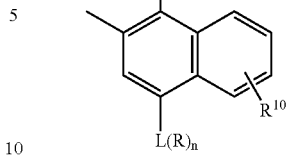

IIIb(ib)

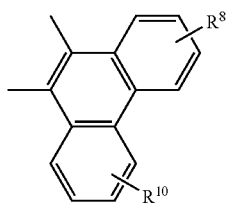

IIIb(ii)

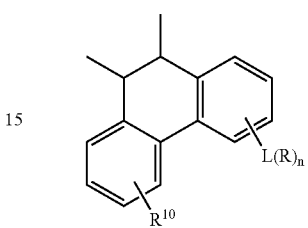

IIIb(iia)

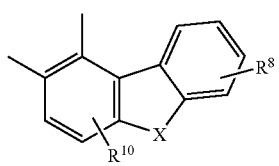

IIIb(iii)

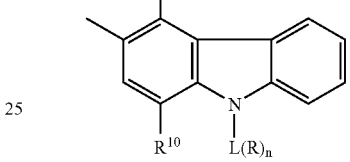

IIIb(iiia)

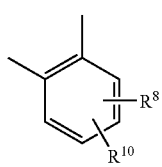

IIIb(iv)

One particularly preferred embodiment of the compounds of formula IV has the formula IVa

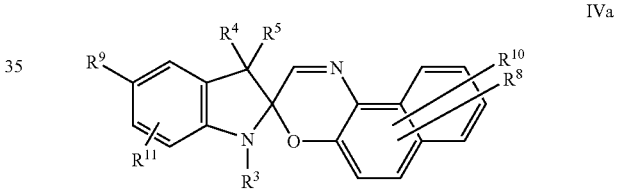

IVa

Specific examples of the group of formula IIIa(i) include

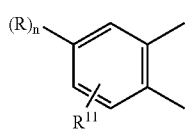

IIIa(ia)

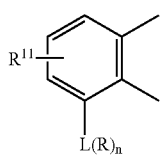

IIIa(ib)

Specific examples of the group of formula IIIb include

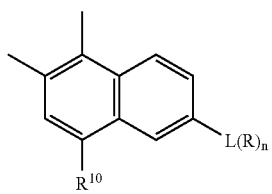

IIIb(ia)

The more preferred compounds of formula IVa are compounds wherein $R^4$ and $R^5$ are preferably independently selected from the group consisting of $C_1$ to $C_4$ alkyl and the group wherein $R^4$ and $R^5$ link together to form a cycloalkyl of from 4 to 6 carbon atoms.

$R^8$ and $R^9$ are independently selected from the group consisting of hydrogen, halogen, cycloalkyl, cycloarylalkyl, hydroxy alkoxy, cyano, alkenyloxyalkyl, alkoxycarbenzyl, aryl, aralkyl, aryloxy, alkylene, thioalkyl and the oligomer of formula $L(R)_n$ wherein L, R and n are as hereinbefore defined;

$R^{10}$ and $R^{11}$ are independently selected from the group consisting of hydrogen, halogen, cycloalkyl, cycloarylalkyl, alkoxy, cyano, alkenyloxyalkyl, alkoxycarbonyl, aryl, arylalkyl, acyloxy and alkylenethioalkyl. Most preferably $R^{10}$ and $R^{11}$ are hydrogen; and at least one of $R^8$ and $R^9$ is the group $L(R)_n$ wherein the total number of monomer units in R is at least 10 and more preferably at least 12.

In order to provide an increase in fade rate of the photochromic in a polymer (preferably a polymer of high Tg) article, the size of the polymer chain must be greater than a certain size. The minimum size will depend on the nature of the oligomer chain and the linking group. It is believed that the fade is significantly accelerated where a polymer chain may adopt a conformation in which a portion of the chain is adjacent the oxazine ring. Accordingly, linking groups which direct the oligomer chain across the molecule (such as the group of formula VI to VIII comprising at least one polymer chain R in a portion otho to the link) may enable the minimum number of effective monomer units to be reduced when compared with other linking groups.

Surprisingly, we have found that a single substituent containing at least one oligomer chain may accelerate fade in a wide variety of polymers whereas in the case of at least two oligomer chains, each on opposite sides of the oxazine ring, the rate of fade of photochromic compounds in polymers may be reduced. Without wishing to be bound by theory, we believe that interaction between oligomer chains on opposite sides of the oxazine portion with the host polymer may restrict or constrain the photochromic molecule to reduce the rate of ring opening and closure of the spiro-oxazine.

Accordingly, in one preferred embodiment one of $R^3$, $R^8$ and $R^9$ is $L(R)_n$ where the R groups together include at least 10 monomer units. Alternatively, $R^8$ and at least one of $R^9$ and $R^3$ (preferably $R^9$) is $L(R)_n$ and the two or more groups $L(R)_n$ contain at least 10 monomer units.

Specific examples of compounds of the invention include those listed in Table 1.

TABLE 1

| | $R^8$ | $R^3$ | $R^9$ | $R^{10}$ | $R^{11}$ |
|---|---|---|---|---|---|
| 1 | 9'-O(CO)(CH$_2$)$_2$CO$_2$(EO)$_7$CH$_3$ | CH$_3$ | H | H | H |
| 2 | 9'-O(CO)(CH$_2$)$_2$CO$_2$(EO)$_{16}$CH$_3$ | CH$_3$ | H | H | H |
| 3 | 9'-O(CO)(CH$_2$)$_2$CO$_2$(EO)$_7$CH$_3$ | CH$_3$ | 5-O(CO)(CH$_2$)$_2$CO$_2$(EO)$_7$CH$_3$ | H | H |
| 4 | H | (EO)$_7$CH$_3$ | H | H | H |
| 5 | 9'-O(CO)(CH$_2$)$_2$CO$_2$(EO)$_{10}$CH$_3$ | CH$_3$ | H | H | H |
| 6 | 9'-OCO(CH$_2$)$_2$CO$_2$(EO)$_{20}$CH$_3$ | CH$_3$ | H | H | H |
| 7 | 6'-OCO(CH$_2$)$_2$CO$_2$(EO)$_{16}$CH$_3$ | CH$_3$ | H | H | H |
| 8 | 6'-N(CH$_2$CH$_3$)CH$_2$CH$_2$O(EO)$_{16}$CH$_3$ | CH$_3$ | H | H | H |
| 9 | 9'-OCO(CH$_2$)$_2$CO$_2$(EO)$_{16}$CH$_3$ | CH$_3$ | H | 6'-N(Et)$_2$ | H |
| 10 | H | CH$_3$ | 5-O(CO)(CH$_2$)CO$_2$(EO)$_{16}$CH$_3$ | H | H |
| 11 | 9'-OC(O)-C$_6$H$_4$-CO$_2$(EO)$_{16}$ | CH$_3$ | H | H | H |
| 12 | 9'-OC(O)-C$_6$H$_2$(EO)$_7$(EO)$_7$(EO)$_7$ | CH$_3$ | H | H | H |
| 13 | H | CH$_3$ | 5-O(CO)(CH$_2$)$_2$CO$_2$(EO)$_{16}$CH$_3$ | H | H |
| 14 | H | CH$_3$ | 5-O(CO)(CH$_2$)$_2$CO$_2$(EO)$_{10}$CH$_3$ | H | H |
| 15 | H | CH$_3$ | 5-O(CO)(CH$_2$)$_2$CO$_2$(EO)$_{20}$CH$_2$ | H | H |
| 16 | H | CH$_3$ | 5-NH(CH$_2$CH$_3$)CH$_2$CH$_2$O(EO)$_{16}$CH$_3$ | H | H |
| 17 | H | CH$_3$ | 5-OC(O)-C$_6$H$_4$-CO$_2$(EO)$_{16}$CH$_3$ | H | H |
| 18 | H | CH$_3$ | 5'-OC(O)-C$_6$H$_2$(EO)$_7$(EO)$_7$(EO)$_7$ | H | H |
| 19 | H | CH$_3$ | 5-O(CO)(CH$_2$)$_2$CO$_2$(EO)$_7$CH$_3$ | 6-N(piperidine) | H |

TABLE 1-continued

| | R⁸ | R³ | R⁹ | R¹⁰ | R¹¹ |
|---|---|---|---|---|---|
| 20 | H | $CH_3$ | 5-O(CO)(CH$_2$)$_2$CO$_2$(EO)$_{16}$CH$_3$ | 6-N(piperidine) | H |
| 21 | H | $CH_3$ | 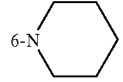 5-OC(O)–C$_6$H$_4$–CO$_2$(EO)$_{16}$CH$_3$ | 6-N(piperidine) | H |
| 22 | H | $CH_3$ | 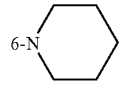 5'-OC(O)-aryl(EO)$_7$/(EO)$_7$/(EO)$_7$ | 6-N(piperidine) | H |
| 23 | H | $CH_3$ | 5-O(CO(CH$_2$)$_2$CO$_2$(EO)$_7$CH$_3$ | 6-CN | H |
| 24 | H | $CH_3$ | 5-O(CO(CH$_2$)$_2$CO$_2$(EO)$_{16}$CH$_3$ | 6-CN | H |
| 25 | H | $CH_3$ | 5-OC(O)–C$_6$H$_4$–CO$_2$(EO)$_{16}$CH$_3$ | 6-CN | H |
| 26 | H | $CH_3$ | 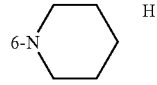 5'-OC(O)-aryl(EO)$_7$/(EO)$_7$/(EO)$_7$ | 6-CN | H |
| 27 | H | $CH_3$ | 5-CH$_2$NH(CO)CH$_2$)$_2$CO$_2$(EO)$_{16}$CH$_3$ | 6-CN | H |
| 28 | H | $CH_3$ | 5-CH$_2$NH(CO)CH$_2$)$_2$CO$_2$(EO)$_{16}$CH$_3$ | 6-N(piperidine) | H |
| 29 | H | $CH_3$ | 5-CH$_2$NH(CO)CH$_2$)$_2$CO$_2$(EO)$_{16}$CH$_3$ | 6-H | H |
| 30 | 9'-O—(CO)(CH2)10-PDMS(855) | $CH_3$ | H | H | H |
| 31 | 9'-O—(CO)(CH2)10-PDMS(855) | $CH_2$—CH(CH$_3$)$_2$ | H | H | H |
| 32 | 9'-O—(CO)(CH2)10-PDMS(855) | $CH_3$—C(CH$_3$)$_3$ | H | H | H |
| 33 | 9'-O—(CO)(CH2)10-PDMS(855) | $CH_3$ | H | 6'-N(Et)$_2$ | H |
| 34 | 9'-O—CH$_2$CH$_2$—O—(CO)(CH2)10-PDMS(855) | $CH_3$ | H | H | H |
| 35 | 9'-O—CH$_2$CH$_2$—O—(CO)(CH2)10-PDMS(855) | $CH_3$ | H | 6'-N(Et)$_2$ | H |
| 36 | 9'-O—(CO)(CH2)10-PDMS(855) | $CH_3$ | 5-OCH$_3$ | H | H |
| 37 | 9'-O—(CO)(CH2)10-PDMS(855) | $CH_3$ | 5-OCH$_3$ | 6'-N(Et)$_2$ | H |
| 38 | 9'-O—CH$_2$CH$_2$—O—(CO)(CH2)10-PDMS(855) | $CH_3$ | 5-OCH$_3$ | H | H |
| 39 | 9'-O—CH$_2$CH$_2$—O—(CO)(CH2)10-PDMS(855) | $CH_3$ | 5-OCH$_3$ | 6'-N(Et)$_2$ | H |
| 40 | H | $CH_3$ | 5-O—(CO)(CH$_2$)$_{10}$-PDMS(855) | H | H |
| 41 | H | $CH_3$—CH(CH$_3$)$_2$ | 5-O—(CO)(CH$_2$)$_{10}$-PDMS(855) | H | H |
| 42 | H | $CH_2$—C(CH$_3$)$_3$ | 5-O—(CO)(CH$_2$)$_{10}$-PDMS(855) | H | H |
| 43 | H | $CH_3$ | 5-O—(CO)(CH$_2$)$_{10}$-PDMS(855) | 6'-CN | H |
| 44 | H | $CH_3$ | 5-O—(CO)(CH$_2$)$_{10}$-PDMS(855) | 6'-N(Et)$_2$ | H |

TABLE 1-continued

|   | R8 | R3 | R9 | R10 | R11 |
|---|---|---|---|---|---|
| 45 | H | $CH_2-C(CH_3)_3$ | 5-O—(CO)(CH$_2$)10-PDMS(855) | 6'-N(Et)2 | H |
| 46 | H | $CH_3$ | 5-O—CH$_2$CH$_2$—O—(CO)(CH2)10-PDMS(855) | H | H |
| 47 | H | $CH_3$ | 5-O—CH$_2$CH$_2$—O—(CO)(CH2)10-PDMS(855) | 6'-N(Et)2 | H |
| 48 | H | $CH_3$ | 5-O—CH$_2$CH$_2$—O—(CO)(CH2)10-PDMS(855) | 6'-CN | H |
| 49 | H | $CH_2-C(CH_3)_3$ | 5-O—CH$_2$CH$_2$—O—(CO)(CH2)10-PDMS(855) | 6'-N(Et)2 | H |
| 50 | O—CO—CH$_2$CH$_2$—COO—CH$_2$CH$_2$CH$_2$-((hepta-isobutyl)POSS) | $CH_3$ | H | H | H | wherein (EO) is the group (CH$_2$CH$_2$O). and PDMS (855)= polydimethylsiloxane with an average molecular weight of 855 including a terminal butyl dimethyl silane end group.

Further preferred compounds are provided in Table 2

TABLE 2

|   | R9 | R3 | R11 | R12 | R13 |
|---|---|---|---|---|---|
| 1 | 5-O—(CO)(CH$_2$)10-PDMS(855) | $CH_3$ | H | Me | Me |
| 2 | 5-O—(CO)(CH$_2$)10-PDMS(855) | $CH_3$ | H | Et | Ft |
| 3 | 5-O—(CO)(CH$_2$)10-PDMS(855) | $CH_3$ | H | pyrrolidino | |
| 4 | 5-O—(CO)(CH$_2$)10-PDMS(855) | $CH_2-CH(CH3)_2$ | H | Me | Me |
| 5 | 5-O—(CO)(CH$_2$)10-PDMS(855) | $CH_2-CH(CH_3)_2$ | H | Et | Et |
| 6 | 5-O—(CO)(CH$_2$)10-PDMS(855) | $CH_2-CH(CH_3)_2$ | H | pyrrolidino | |
| 7 | 5-O—(CO)(CH$_2$)10-PDMS(855) | $CH_2-C(CH_3)_3$ | H | Me | Me |
| 8 | 5-O—(CO)(CH$_2$)10-PDMS(855) | $CH_2-C(CH_3)_3$ | H | Et | Et |
| 9 | 5-O—(CO)(CH$_2$)10-PDMS(855) | $CH_2-C(CH_3)_3$ | H | pyrrolidino | |
| 10 | 5-O—CH$_2$CH$_2$—O—(CO)(CH2)10-PDMS(855) | $CH_3$ | H | Me | Me |
| 11 | 5-O—CH$_2$CH$_2$—O—(CO)(CH2)10-PDMS(855) | $CH_3$ | H | Et | Et |
| 12 | 5-O—CH$_2$CH$_2$—O—(CO)(CH2)10-PDMS(855) | $CH_3$ | H | pyrrolidino | |
| 13 | 5-O—CH$_2$CH$_2$—O—(CO)(CH2)10-PDMS(855) | $CH_2-CH(CH_3)_2$ | H | Me | Me |
| 14 | 5-O—CH$_2$CH$_2$—O—(CO)(CH2)10-PDMS(855) | $CH_2-CH(CH_3)_2$ | H | Et | Et |
| 15 | 5-O—CH$_2$CH$_2$—O—(CO)(CH2)10-PDMS(855) | $CH_2-CH(CH_3)_2$ | H | pyrrolidino | |
| 16 | 5-O—CH$_2$CH$_2$—O—(CO)(CH2)10-PDMS(855) | $CH_2-C(CH_3)_3$ | H | Me | Me |
| 17 | 5-O—CH$_2$CH$_2$—O—(CO)(CH2)10-PDMS(855) | $CH_2-C(CH_3)_3$ | H | Et | Et |
| 18 | 5-O—CH$_2$CH$_2$—O—(CO)(CH2)10-PDMS(855) | $CH_2-C(CH_3)_3$ | H | pyrrolidino | |

TABLE 2-continued

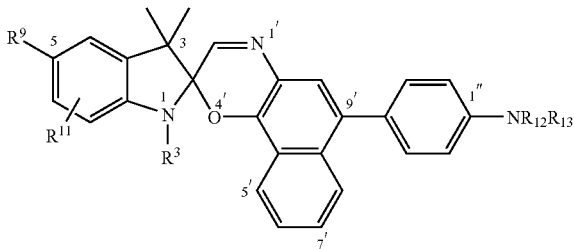

| | R9 | R3 | R11 | R12 | R13 |
|---|---|---|---|---|---|
| 19 | —O—CO—$CH_2CH_2$—COO—$CH_2CH_2CH_2$-((hepta-isobutyl)POSS) | $CH_3$ | H | Me | Me |
| 20 | —O—CO—$CH_2CH_2$—COO—$CH_2CH_2CH_2$-((hepta-isobutyl)POSS) | $CH_3$ | H | Et | Et |
| 21 | —O—CO—$CH_2CH_2$—COO—$CH_2CH_2CH_2$-((hepta-isobutyl)POSS) | $CH_3$ | H | pyrrolidino | |
| 22 | —O—CO—$CH_2CH_2$—COO—$CH_2CH_2CH_2$-((hepta-isobutyl)POSS) | $CH_2$—$CH(CH_3)_2$ | H | Me | Me |
| 23 | —O—CO—$CH_2CH_2$—COO—$CH_2CH_2CH_2$-((hepta-isobutyl)POSS) | $CH_2$—$CH(CH_3)_2$ | H | Et | Et |
| 24 | —O—CO—$CH_2CH_2$—COO—$CH_2CH_2CH_2$-((hepta-isobutyl)POSS) | $CH_2$—$CH(CH_3)_2$ | H | pyrrolidino | |
| 25 | —O—CO—$CH_2CH_2$—COO—$CH_2CH_2CH_2$-((hepta-isobutyl)POSS) | $CH_2$—C$(CH_3)_3$ | H | Me | Me |
| 26 | —O—CO—$CH_2CH_2$—COO—$CH_2CH_2CH_2$-((hepta-isobutyl)POSS) | $CH_2$—C$(CH_3)_3$ | H | Et | Et |
| 27 | —O—CO—$CH_2CH_2$—COO—$CH_2CH_2CH_2$-((hepta-isobutyl)POSS) | $CH_2$—C$(CH_3)_3$ | H | pyrrolidino | |

The more preferred compounds of the invention are of formula (Ivb)

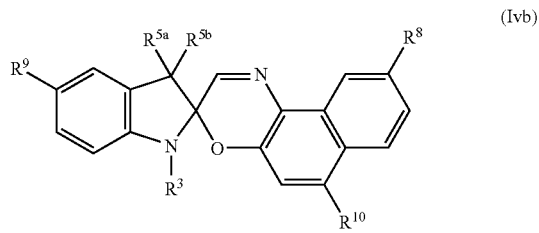

(Ivb)

where the substituents are hereinbefore described and even more preferably $R^3$ is $C_1$ to $C_4$ alkyl; $C_3$ to $C_6$ cycloalkyl, aryl, alkylaryl, arylalkyl and $L(R)_n$; $R^{5a}$ and $R^{5b}$ are independently selected from $C_1$ to $C_6$ alkyl $C_3$ to $C_6$ cycloalkyl, aryl; $R^8$ and $R^9$ are selected from hydrogen, hydroxy, $C_1$ to $C_6$ alkoxy; $R^{19}$ is selected from the group hydrogen, hydroxy, $C_1$ to $C_9$ alkoxy —$NR^6R^7$ wherein $R^6$ and $R^7$ are independently hydrogen, $C_1$ to $C_6$ alkyl and wherein $R^6$ and $R^7$ may together form a divisional hydrocarbon chain of 4 to 6 carbon atoms.

As we have discussed above, in order to maximise the rate of colouration and fade in polar and non-polar polymers it is preferred that one of $R^3$, $R^8$ and $R^9$ is $L(R)_n$ comprising at least 10, more preferably at least 12 monomer units and the other two of $R^3$, $R^8$ and $R^9$ are other than $L(R)_n$ where $L(R)_n$ contains 7 monomer units.

In compounds where more than one of $R^3$, $R^8$ and $R^9$ is $L(R)_n$ comprising at least 7 monomer units, the effect on the rate of colouration and fade will depend to some extent on the oligomer and type of polymer. In cases where the polymer and oligomers are compatible, the rate of fade may be decreased and when the oligomer and resin are less compatible, the effect may be less or fade may be increased.

We have found that for compounds of formula IV a (preferably IVb) if $R^8$ and $R^9$ are shorter chains or smaller substituents they are also useful in controlling the rate of fade though to a more limited extent.

In a further embodiment, the invention therefore provides compounds of formula IVa (preferably IVb) wherein $R^8$ and $R^9$ are each selected from groups of formula I and groups of formula L(R), as hereinbefore defined and the group $LR^{11}$ wherein $R^{11}$ is lower alkyl, lower haloalkyl, lower polyalkyleneoxy aryl and aryl(lower alkyl). The term lower is used to mean up to 6 carbon atoms in the chain and preferably up to 4.

In yet another embodiment we provide an intermediate for preparation of compounds of the invention, the intermediate being of formula IVa and more preferably IVb wherein $R^8$ and $R^9$ are selected from XH wherein X is hereinbefore defined. Preferably $R^8$ and $R^9$ are the same.

Compounds of the invention may be prepared by reaction of intermediates Va or Vb and VI.

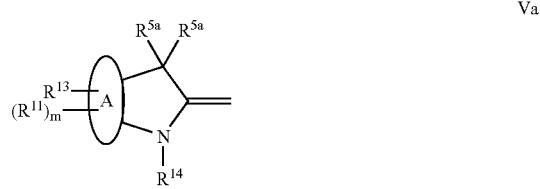

Va

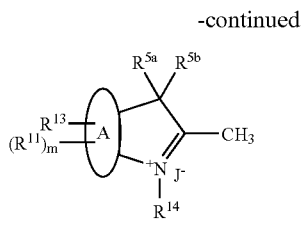

Vb

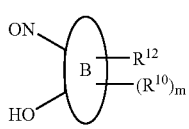

VI

One method for preparing compounds of the invention comprises reacting a methylene indolene of formula Va or Fishers base or indolium salt of formula Vb where J is halogen, particularly the iodide salt, wherein $R^{13}$ is $R^9$ and $R^{14}$ is $R^3$ with a nitrosohydroxy compound of formula VI to provide a compound of the invention of formula IV.

Alternatively, a methylene indolene of formula Va or indolium salt of formula Vb may be reacted with a nitrosohydroxy compound of formula VI wherein $R^{12}$ and $R^{13}$ are independently selected from the group consisting of hydrogen and —XH and at least one of $R^{12}$ and $R^{13}$ is —XH to provide an intermediate of formula VII.

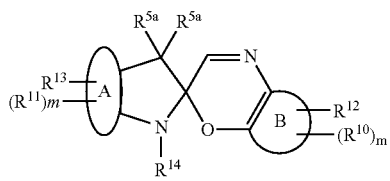

VII and reacting the compound of formula VIII with a compound of formula VII

JL(R)$_n$

VIII wherein J is a leaving group to form a compound of formula IV wherein at least one of $R^9$ and $R^9$ are the group L(R)$_n$.

Alternatively or in addition the compound of formula IV wherein $R^3$ is L(R)$_n$ may be prepared by (a) reacting the compound of formula Va or Vb with a compound of formula VIII to provide a compound of formula Va and Vb where $R^{14}$ is L(R)$_n$ and reacting the compound of formula VIa or VIb with a compound of formula VI to provide a compound of formula IV wherein $R^3$ is L(R)$_n$.

Specific examples of compounds of formula VIII, include J L(R)$_n$ where J is chlorine, L is of formula IIa to IIc where p is 0 and R is any one of the R group examples (i) to (v) shown above.

Compounds of formula IV where L is a bond may additionally be prepared by using a toluene sulfonyl leaving group for example by reaction of the compound of formula IX

IX with a compound of formula IV wherein at least one of $R^8$ or $R^9$ is XH and/or $R^3$ is hydrogen to provide a compound where one or more groups is alkoxylated.

Compounds of formula X

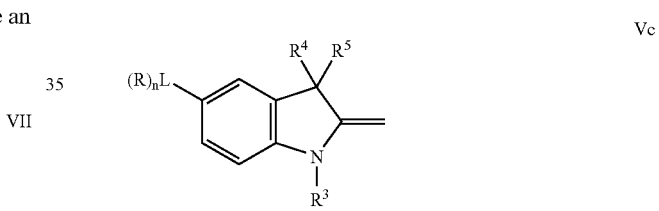

X having a wide variety of the fused aromatic groups B may be prepared using the intermediate of formula Vc.

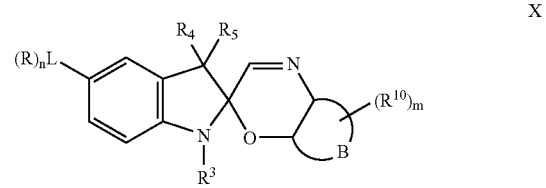

Vc

The fused aromatic group B and its substituents may be chosen to provide the disused colour of the photochromic compound. Such compounds provide a versatile method of preparation of rapid fade spiroindolineoxazines.

Examples of suitable substituted methylene indolene compounds of formula Va and Vb include 5-amino indolene compounds described by Gale & Wiltshire (J. Soc. Dye and Colourants 1974, 90, 97-00), 5-amino methylene compounds described by Gale, Lin and Wilshire (Aust. J. Chem. 1977 30 689-94) and 5-hydroxy compounds described in Tetrahedron Lett, 1973 12 903-6 and in U.S. Pat. No. 4,062,865.

One of the preferred groups of photochromics are the spiropyrans. Examples of spiropyrans include compounds of formula XIX and XX

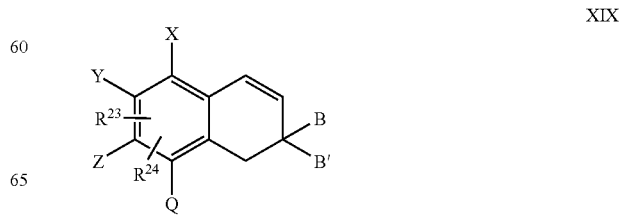

XIX

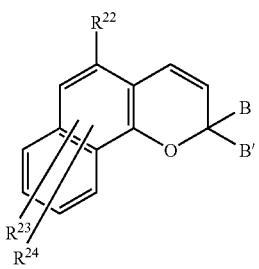

wherein in XIX the groups X, Y, Z and Q may be substituents including where one or more thereof form a carbocyclic ring optionally fused with aryl and the substituents $R^{23}$ and $R^{24}$ may be present in any ring; and wherein B and B are optionally substitutedaryl and heteroaryl; and $R^{22}$, $R^{23}$ and $R^{24}$ are independently selected from hydrogen; halogen; $C_1$ to $C_3$ alkyl; the group $L(R)_n$; and the group of formula COW wherein W is $OR^{25}$, $NR^{26}R^{27}$, piperidino or morpholino wherein $R^{25}$ is selected from the group consisting of $C_1$ to $C_6$ alkyl, phenyl, ($C_1$ to $C_6$ alkyl)phenyl, $C_1$ to $C_6$ alkoxyphenyl, phenyl $C_1$ to $C_6$ alkyl ($C_1$ to $C_6$ alkoxy)phenyl, $C_1$ to $C_6$ alkoxy $C_2$ to $C_4$ alkyl and the group $L(R)_n$; $R^{26}$ and $R^{27}$ are each selected from the group consisting of $C_1$ to $C_6$ alkyl, $C_5$ to $C_7$ cycloalkyl, phenyl, phenyl substituted with one or two groups selected from $C_1$ to $C_6$ alkyl and $C_1$ to $C_6$ alkoxy and the group $L(R)_n$; $R^{22}$ and $R^{23}$ may optionally from a carboxylic ring of 5 or 6 ring members optionally fused with an optionally substituted benzene and wherein at least one of the substituents selected from the group of substituents consisting of B and B', $R^{22}$, $R^{23}$, $R^{24}$, $R^{25}$, $R^{26}$ and $R^{27}$ is the group $L(R)_n$.

When $R^{22}$ and $R^{23}$ are carbocyclic a preferred compound is of formula XX(d)

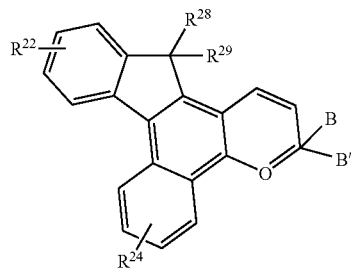

where $R^{22}$, $R^{28}$ and $R^{29}$ are as defined for $R^{22}$ above.

Preferably B and B' are independently selected from the group consisting of aryl optionally substituted with from 1 to 3 substituents, heteroaryl optionally substituted with from 1 to 3 substituents. The substituents where present are preferably selected from the group consisting of hydroxy, aryl, ($C_1$ to $C_6$) alkoxyaryl, ($C_1$ to $C_6$) alkylaryl, chloroaryl ($C_3$ to $C_7$) cycloalkylaryl, ($C_3$ to $C_7$) cycloalkyl, ($C_3$ to $C_7$) cycloalkoxy, ($C_3$ to $C_7$) cycloalkoxy, ($C_1$ to $C_6$) alkyl, aryl ($C_1$ to $C_6$) alkyl, aryl ($C_1$ to $C_6$) alkoxy, aryloxy, aryloxyalkyl, aryloxy ($C_1$ to $C_6$) alkoxy, ($C_1$ to $C_6$) alkylaryl, ($C_1$ to $C_6$) alkyl, ($C_1$ to $C_6$)) alkoxyaryl, ($C_1$ to $C_6$) alkyl, ($C_1$ to $C_6$) alkoxyaryl, ($C_1$ to $C_6$) alkyl, ($C_1$ to $C_6$) alkoxyaryl, ($C_1$ to $C_6$) alkoxy, amino, N—($C_1$ to $C_6$) alkyl ipirazino, N-aryl piperazino, indolino, piperidino, aryl pipersillins, morpholino, thiomorpholino, tetrahydro quinolino.

$NR^{29}R^{30}$ wherein $R^{29}$ and $R^{30}$ are independently selected from the group selected from $C_1$ to $C_6$ alkyl, phenyl, $C_5$ to $C_7$ cycloalkyl and the group wherein $R^{29}$ and $R^{30}$ form a linking group of 4 or 5 linking groups comprising methylene groups and optionally containing one or two hetero atoms and optionally further substituted by $C_1$ to $C_3$ alkyl and the group $L(R)_n$.

$R^{22}$ is selected from the group consisting of hydrogen, $C_1$ to $C_6$ alkyl; COW where W is $OR^{25}$ wherein $R^{25}$ $C_1$ to $C_6$ alkyl; and the group $NR^{26}R^{27}$; wherein $R^{26}$ and $R^{27}$ are independently $C_1$ to $C_6$ alkyl; and the group $L(R)_n$.

Particularly referred naphthopyran compounds are of formula XX(a)

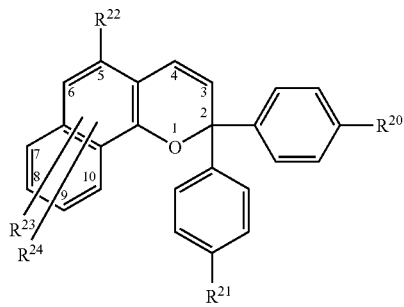

wherein $R^{20}$ and $R^{21}$ are independently selected from the group consisting of hydrogen, hydroxy, alkoxy, amino, alkylamino, dialkylamino and $L(R)_n$;

$R^{22}$ is the group COW where W is $C_1$ to $C_6$ alkoxy or the group $L(R)_n$;

$R^{23}$ is selected from the group consisting of hydrogen and $NR^{26}R^{27}$ where $R^{26}$ are independently selected from the group consisting of $C_1$ to $C_6$ alkyl and where $R^{26}$ and $R^{27}$ may together form an alkylene group of 4 to 6 carbon atoms;

$R^{24}$ is hydrogen or the group $L(R)_n$; and wherein at least one of $R^{22}$ and $R^{24}$ is $L(R)_n$.

Specific example of the naphthopyran compounds of formula XX(a) include those shown in Table 3:

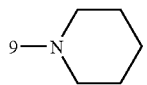

| $R^{20}$ | $R^{21}$ | $R^{22}$ | $R^{23}$ | $R^{24}$ |
|---|---|---|---|---|
| $OCH_3$ | H | $CO_2CH_3$ | H | $6\text{-}O(CO)(CH_2)_{10}(SiMe_2O)_{10}Si(CH_2)_3CH_3$ |
| $OCH_3$ | $OCH_3$ | $OO2CH_3$ | H | $6\text{-}O(CO)(CH_2)_{10}(SiMe_2O)_{10}Si(CH_2)_3CH_3$ |
| $(CH_3)_2N$ | $(CH_3)_2N$ | $CO_2CH_3$ | H | $6\text{-}O(CO)(CH_2)_{10}(SiMe_2O)_{10}Si(CH_2)_3CH_3$ |
| $(CH_3)_2N$ | H | $-(CO)O(CH_2)_2 O(CO)(CH_2)_{10}(SiMe_2 O)_{10}Si(CH_2)_3CH_3$ | $9\text{-}(CH_3)_2NH$ | H |
| $(CH_3)_2N$ | H | $CO_2CH_3$ | 9—N(piperidine) | $6\text{-}O(CO)(CH_2)_{10}(SiMe_2O)_{10}Si(CH_2)_3CH_3$ |
| $(CH_3)_2N$ | H | $CO_2CH_3$ | H | $6\text{-}OCO(CH_2)_2CO_2(EO)_{16}CH_3$ |
| $4\text{-}O(CO)(CH_2)_{10}(SiMe_2O)_{10}Si(CH_2)_3CH_3$ | H | $CO_2CH_3$ | H | H |

Compounds of formula XX wherein $R^{23}$ and/or $R^{24}$ comprise the oligomer group $L(R)_n$ may be prepared from a suitably substituted acetophenone, benzophenone or benzaldehyde of formula XXI(a). In this process the compound of formula XXI(a) (or a polyhydroxy compound where more than one substituent is required) is reacted with an oligomer esterified toluene sulfonate of formula XXI to provide the corresponding oligomer ether of formula XXI(b). THE aromatic oligomer ether of formula XXI(b) is reacted with an ester of succinic acid such as the dialkyl succinate of formula XXI(c). A Stobbe reaction produces the condensed half ester of formula XXII which undergoes cyclo dehydration in the presence of acidic anhydride to form the naphthalene oligomer ether of formula XXIII. This compound of formula XXIII may be reacted with acid such as hydrochloride acid and an anhydrous alcohol such as methanol to form the corresponding naphthol shown in formula XXIV which is in turn coupled with the propargyl alcohol of formula XXV to form the oligomer substituted naphthopyran of the invention of formula XX(b).

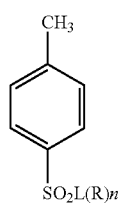

XXI

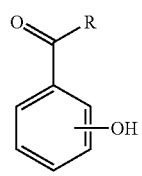

XXI(a)

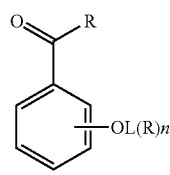

XXI(b)

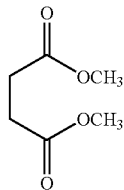

XXI(c)

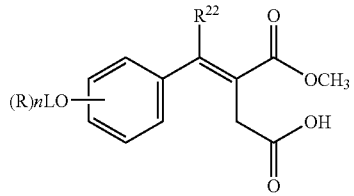

XXII

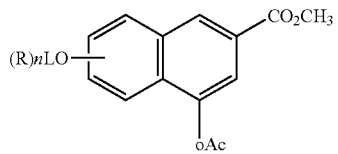

XXIII

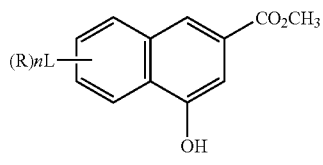

XXIV

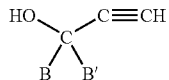

XXV

-continued

XX(b)

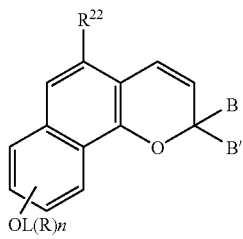

Alternatively, compounds of formula XX(c) in which at least one of the germinal phenyl groups is substituted by an oligomer may be prepared from the benzophenone of formula XXI(f). In this process the benzophenone substituted with the appropriate hydroxyl groups is reacted with the oligomer ester of toluene sulfonate of formula XXI(e) to form the corresponding oligomer substituted benzophenone of formula XXI(g). The corresponding propargal alcohol of formula XXV(a) is prepared from the benzophenone by reaction with sodium acetylide in a solvent such as THF. This propargal alcohol of formula XXV(a) is coupled with the appropriate substituted naphthol of formula XXIV(b) to form the oligomer substituted naphthopyrane of formula XX(c).

-continued

XX(c)

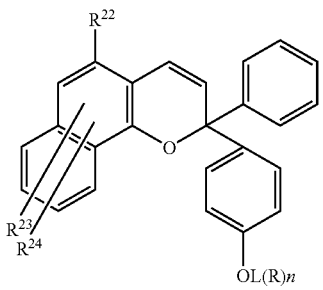

A further option for forming oligomer substituted pyrans of the invention of formula XX(d) in which the oligomer is present in the 5-position of the naphthopyran may utilise the corresponding carboxylated naphthol of formula XXIII(a). In such a process the naphthol of formula XXIII(a) is reacted with an appropriate oligomer of formula XXI(d) (particularly where linking group L comprising oxygen) to provide an oligomer ester of formula XXIV(a). The oligomer naphthol ester of formula XXIV(a) may be reacted with propargyl alcohol of formula XXV to provide the naphtholpyran of formula XX(d) in which the oligomer is present in the five position.

XXI(e)

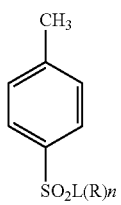

XXI(f)

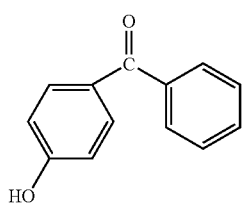

XXI(g)

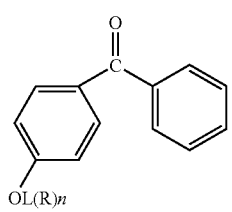

XXV(a)

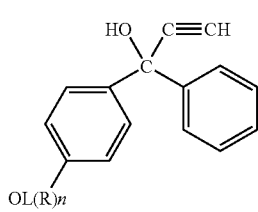

XXIV(b)

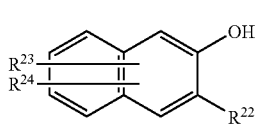

XXIII(a)

HL(R)n    XXI(d)

COL(R)n    XXIV(a)

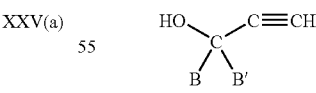

XXV

L(R)n    XX(d)

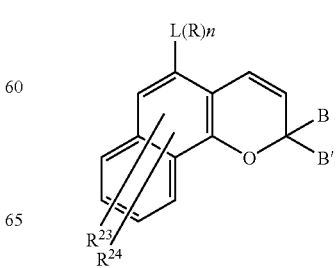

In a further alternative compounds of formula XX wherein R²² comprises the oligomer L(R)ₙ may be formed by reacting a compound of formula XX(e) with an acid chloride or anhydride substituted oligomer to provide a compound of formula:

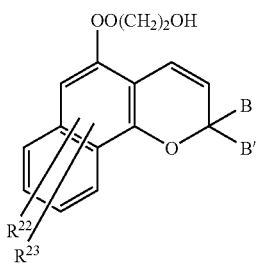

XX(e)

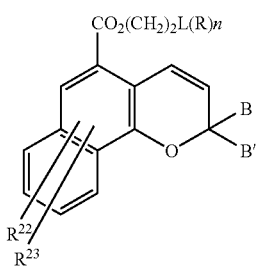

XX(f)

Examples of fulgides and fulgimides include compounds of formula XXX and more preferably XXXa:

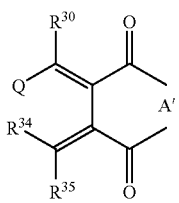

XXX

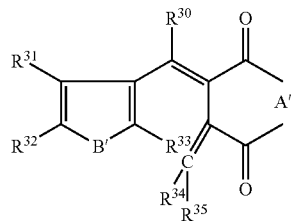

XXXa wherein

Q is selected from the group consisting of optionally substituted aromatic, optionally substituted heteroaromatic (where said aromatic/heteroaromatic may be mono or polycyclic aromatic/heteroaromatic);

$R^{30}$, $R^{32}$ and $R^{33}$ are independently selected from the group consisting of a $C_1$ to $C_4$ alkyl, $C_1$ to $C_4$ alkoxy phenyl, phenoxy mono- and di($C_1$-$C_4$) alkyl substituted phenyl or phen($C_1$-$C_4$)alkyl and $R^{32}$ and $R^{32}$ optionally together form a fused benzene which may be further substituted;

A' is selected from the group consisting of oxygen or =N—$R^{36}$, in which $R^{36}$ is $C_1$-$C_4$ alkyl or phenyl, B' is selected from the group consisting of oxygen or sulfur;

$R^{34}$ and $R^{35}$ independently represents a $C_1$-$C_4$ alkyl, phenyl or phen($C_1$-$C_4$) alkyl or one of $R^{34}$ and $R^{35}$ is hydrogen and the other is one of the aforementioned groups, or $R^{34}R^{35}$=represents an adamantylidene group;

and wherein at least one of $R^{30}$, $R^{31}$, $R^{32}$, $R^{35}$ and $R^{36}$ is the group L(R)ₙ.

When B is $NR^{30}$ then $A^1$ is generally oxygen.

Specific examples of compounds of formula XXX include those shown in the following Table 4:

| No. | A' | B' | $R^{30}$ | R31, $R^{32}$ | $R^{33}$ | $R^{34}$ | $R^{35}$ |
|---|---|---|---|---|---|---|---|
| 1 | O | O | $CH_3$ | $CH_3$, $CH_3$ | $CH_3$ | $CH_3$ | $CH_3$ |
| 2 | O | O | $CH_3$ | (methylphenyl structure) | $CH_2C_6H_4OCO$ (POS) | $CH_3$ | $CH_3$ |
| 3 | O | O | $CH_3$ | H, $CH_3$ | $CH_3$ | $CH_3$ | $CH_3$ |
| 4 | N—$CH_2CH_3$ | O | $CH_3$ | H, $CH_3$ | $CH_3$ | $CH_3$ | $CH_3$ |
| 5 | O | O | $CH_3$ | H, $CH_3$ | $CH_3$ | $CH_3$ | $CH_3$ |
| 6 | O | O | $CH_3$ | H, $C_6H_5$ | $C_6H_5$ | $CH_3$ | $CH_3$ |
| 7 | O | O | $CH_3$ | H, $CH_3$ | $CH_3$ | H | $C_6H_5O$ (POS) |
| 8 | O | $NCH_3$ | $CH_3$ | H, $CH_3$ | $CH_3$ | $CH_3$ | $CH_3$ |
| 9 | $NC_6H_4OCO$ (POS) | O | $CH_3$ | H, $CH_3$ | $CH_3$ | $CH_3$ | $CH_3$ |
| 10 | O | $NC_6H_5CH_3$ | $CH_3$ | H, $CH_3$ | $CH_3$ | $CH_3$ | $CH_3$ |
| 11 | O | $NC_6H_5$ | $CH_3$ | H, $C_6H_5$ | $CH_3$ | $CH_3$ | $CH_3$ |
| 12 | O | $NC_6H_5$ | $CH_3$ | H, $CH_3$ | $CH_3$ | Cyclopropyl | cyclopropyl |

POS is —$(CH_2)_{10}(SiMe_2O)_{10}Si(CH_2)_3CH_3$

The fulgides and fulgimides comprising oligomer substituents in accordance with the invention may be particularly useful in molecular switches.

The fulgides and fulgimides of formula XXX may be formed in accordance with procedures similar to those described in U.S. Pat. No. 4,220,708. Fulgides of formula XXX(a) in which the group A- is oxygen may be prepared from five membered heterocycle of formula XXX by reaction with an ester of succinic acid of formula XXXII wherein $R^{37}$ is a residue of an alcohol, by a Stobbe condensation reaction. Hydrolysing the half ester product of XXXIII formed in the reaction provides the diacid of XXXIII wherein $R^{37}$ is hydrogen. Heating of the diacid of formula XXXIII yields the succinic anhydride product of formula XXXIII(a). The Stobbe condensation may be carried out by refluxing in t-butanol containing potassium t-butoxide or with sodium hydride in anhydrous toluene. Compounds of the invention of formula XXX(b) in which A- of formula XXX is N-36 may be prepared from the compound of XXX(a) by heating the anhydride and a primary amine $R^{36}NH_2$ to produce the corresponding half amide which can in turn be cyclised to form the imide of formula XXX(b) for example by heating with an acid chloride or acid anhydride. Alternatively the half ester Stobbe condensation product of formula XXX can be converted to the imide of XXX(b) by reaction with a compound of formula $R^{36}NHMgBr$ to produce the corresponding succinamic acid which may be dehydrated with an acid chloride to provide the compound of formula XXX(b). Compounds of formula XXX(b)

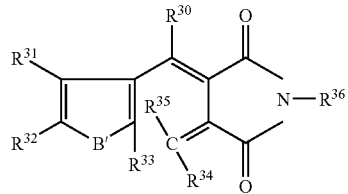

XXXI

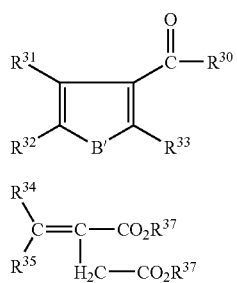

XXXII wherein $R^{36}$ comprises an oligomer group are particularly preferred.

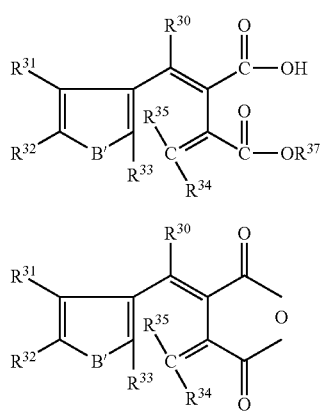

XXXIII

XXX(a)

-continued

XXX(b)

Compounds of formula XXXI wherein $R^{30}$ includes the oligomer $L(R)_n$ may be prepared by reaction of an oligomer acid chloride such as (XXXV) with the appropriate furon in the presence of a Lewis acid catalyst (such as tin tetrachloride):

$$ClCO(CH_2)_{10}(Si(Me)_2O)_{10}(CH_2)_3CH_3 \quad (XXXV)$$

Fulgimide compounds of formula XXX in which
A' is the group of formula XXXVI may be prepared by reaction of an amine with a free nucleophilic group such as 4-hydroxyaniline with the corresponding fulgide of formula XXX where A' is oxygen to provide the intermediate fulgimide having a free nuclophilic group such as hydroxy (eg formula XXXVII) and reaction of the free nucleophilic of the fulgimide with the oligomer acid chloride or anhydride (such as formula XXXV) to provide the oligomer substituted fulgimide of (eg formula XXXVI).

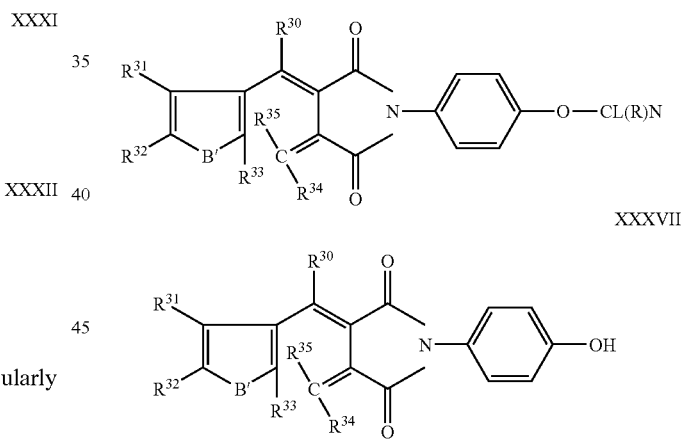

XXXVI

XXXVII

The compounds of the invention tend to be oils. This makes them more soluble in monomers and polymer matrices. It also means they are less likely to crystallise in the matrix, thus this may allow higher loading of dyes and may also prevent the crystallisation that may occur with conventional photochromic dyes.

Photochromic compounds of the invention comprising a dialkyl siloxane oligomer may be prepared by anionic polymerization of the appropriate halo-substituted photochromic moiety.

For example a chlorinated photochromic may be functionalised with a dialkyl siloxane as follows:

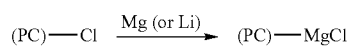

-continued

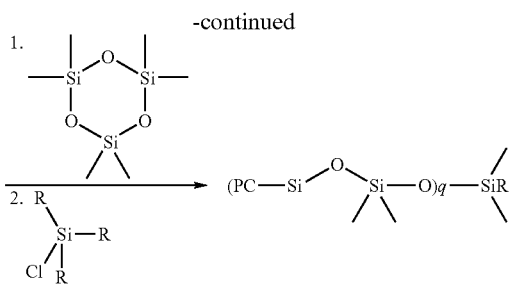

An alternative method for oligomer growth on a photochromic moiety is the ATRP and RAFT method or other living polymer growth methods.

This general method of growing oligomers from living initiation sites on the photochromic moiety provides a controlled growth process which may be adapted to use with a wide range of photochromic moieties. Furthermore it will be understood that a range of living polymerisation methods including anionic, ATRP and RAFT may be chosen depending on the types oligomers to be prepared.

Examples of azo dyes include compounds of formula XL

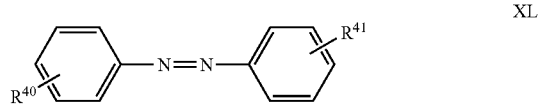

XL wherein:

$R^{40}$ and $R^{41}$ are independently selected from the group consisting of hydrogen, $C_1$ to $C_6$ alkyl, $C_1$ to $C_6$ alkoxy, —$NR^{42}R^{43}$ wherein $R^{42}$ and $R^{43}$ are as defined for $R^{26}$ and $R^{27}$ aryl (such as phenyl) aryl substituted with one or more substituents selected from $C_1$ to $C_6$ alkyl and $C_1$ to $C_6$ alkoxy, substituted $C_1$ to $C_6$ alkyl wherein the substituent is selected from aryl and $C_1$ to $C_6$ alkoxy, substituted $C_1$ to $C_6$ alkoxy wherein the substituent is selected from $C_1$ to $C_6$ alkoxy aryl and aryloxy.

Specific examples of azo dyes include the following compounds of formula XL:

| $R^{40}$ | $R^{41}$ |
|---|---|
| H | $OCO(CH_2)_2COOCH_2(CF_2)_9CF_3$ |
| $OCH_3$ | $OCO(CH_2)_2OCO(CH_2)_{10}(SiMe_2O)_{10}SiMe_2C_4H_9$ |

The compounds of the invention tend to be oils. This makes them more soluble in monomers and polymer matrices. It also means they are less likely to crystallise in the matrix, thus this may allow higher loading of dyes and may also prevent the crystallisation that may occur with conventional photochromic dyes.

The compounds of the invention have their own built-in nanoenvironment because the dye can never be separated from a favourable oligomer.

The compounds of the invention may contain one or more photochromic dyes. The compounds of the invention may also be used in mixtures with conventional photochromics.

The use of compounds of the invention allows the fade speed of the photochromic to be changed without changing its colour. Thus it allows the tuning of fade speed for different coloured dyes. This is important to get a consistent colour when fading occurs. Thus, if a blue dye of a particular speed is needed, modification can be made to include an oligomer of an appropriate length in accordance with the invention.

The photochromic compounds (or compositions containing same) of the present invention may be applied or incorporated into a host material by methods known in the art. Such methods include dissolving or dispersing the compound in the host material. The compound may be melt blended with the host matrix.

Imbibation of the photochromic compound into the host material, by immersion, thermal transfer, or coating, and incorporation of the photochromic layer as part of a separation layer between adjacent layers of the host material. The term "imbibation" or "imbibe" is intended to mean and include diffusion of the photochromic compound alone into the host material, solvent assisted diffusion, absorption of the photochromic compound into a porous polymer, vapor phase transfer, and other such transfer mechanisms. For example:

(a) The photochromic compounds (or compositions containing same) of the present invention can be mixed with a polymerizable composition that, upon curing, produces an optically clear polymeric host material and the polymerizable composition can be cast as a film, sheet or lens, or injection molded or otherwise formed into a sheet or lens;

(b) The photochromic compounds of the present invention can be dissolved or dispersed in water, alcohol or other solvents or solvent mixtures and then imbibed into the solid host material by immersion for from several minutes to several hours, eg, 2-3 minutes to 2-3 hours for the host material in a bath of such solution or dispersion. The bath is conventionally at an elevated temperature, usually in the range of 50° C. to 95° C. Thereafter, the host material is removed from the bath and dried;

(c) The photochromic compounds (and compositions containing the same) may also be applied to the surface of the host material by any convenient manner, such as spraying, brushing, spin-coating or dip-coating from a solution or dispersion of the photochromic material in the presence of a polymeric binder. Thereafter, the photochromic compound is imbibed by the host material by heating it, eg, in an oven, for from a minute to several hours at temperatures in the range of from 80° C. to 180° C.;

(d) In a variation of the above imbibation procedure, the photochromic compound or composition containing the same can be deposited onto a temporary support, or fabric, which is then placed in contact with host material and heated, eg, in an oven;

(e) The photochromic compounds can be dissolved or dispersed in a transparent polymeric material which can be applied to the surface of the host in the form of a permanent adherent film or coating by any suitable technique such as spraying, brushing, spin-coating or dip-coating;

(f) The photochromic compounds can be incorporated or applied to a transparent polymeric material by any of the above mentioned methods, which can then be placed within the host material as a discrete layer intermediate to adjacent layers of a host material(s);

(g) The photochromic adduct of the invention may be incorporated into a dye composition by ball milling with a carrier to disperse it in a binder matrix. Such a composition may be used as an ink, for example in ink jet printing and suitable (PC) moieties may be chosen to allow security markings on documents to be visible on exposure to UV light used in photocopy;

(h) The photochromic compound may be compounded with suitable resins and the resin melted to shape it to form a film, for example by blow moulding or to form more complex extruded shapes, e.g. by injection moulding and/or blown structures.

The transfer method is described, inter alia, in the documents U.S. Pat. Nos. 4,286,957 and 4,880,667. In this technique, a surface of the transparent polymer substrate is coated with a layer of a varnish containing the photochromic substance to be incorporated. The substrate, thus coated, is then treated thermally in order to cause the photochromic substance to migrate into the substrate.

It is a significant advantage of the adduct photochromic of the invention that they are relatively stable even at elevated temperature. In contrast attempt made to improve fade results using unsaturated functional groups result in compounds which polymerise at elevated temperature and must generally be stored to avoid premature polymerisation.

The present invention is more particularly described in the following examples which are intended as illustrative only since numerous modifications and variations therein will be apparent to those skilled in the art.

Examples of host materials that may be used with the photochromic compounds of the present invention include polymers, i.e., homopolymers and copolymers of polyol(allyl carbonate) monomers, homopolymers and copolymers of polyfunctional acrylate monomers, polyacrylates, poly(alkylacrylates) such as poly(methylmethacrylate), cellulose acetate, cellulose triacetate, celluslose acetate propionate, cellulose acetate butyrate, poly(vinyl acetate), poly(vinylalcohol), poly(vinylchloride), poly(vinylidene chloride), polyurethanes, polycarbonates, poly(ethylene-terephthalate), polystyrene, copoly(styrene-methylmethacrylate), copoly(styrene-acrylateonitrile), poly(vinylbutryal), and homopolymers and copolymers of diacylidene pentaerythritol, particularly copolymers with polyol(allylcarbonate) monomers, e.g. diethylene glycol bis(allyl carbonate), and acrylate monomers. Transparent copolymers and blends of the transparent polymers are also suitable as host materials.

The host material may be an optically clear polymerized organic material prepared from a polycarbonate resin, such as the carbonate-linked resin derived from bisphenol A and phosgene which is sold under the trademark LEXAN; a poly (methylmethacrylate), such as the material sold under the trademark PLEXIGLAS; polymerizates of a polyol(allyl carbonate), especially diethylene glycol bis(allyl carbonate), which is sold under the trademark CR-39, and its copolymers such as copolymers with vinyl acetate, eg copolymers of from about 80-90 percent diethylene glycol bis(allyl carbonate) and 10-20 percent vinyl acetate, particularly 80-85 percent of the bis(allyl carbonate) and 15-20 percent vinyl acetate, cellulose acetate, cellulose propionate, cellulose butyrate, polystyrene and copolymers of styrene with methyl methacrylate, vinyl acetate and acrylonitrile, and cellulose acetate butyrate.

Polyol (allyl carbonate) monomers which can be polymerised to form a transparent host material are the allyl carbonates of linear or branched aliphatic glycol bis(allyl carbonate) compounds, or alkylidene bisphenol bis(allyl carbonate) compounds. These monomers can be described as unsaturated polycarbonates of polyols, eg glycols. The monomers can be prepared by procedures well known in the art, eg, U.S. Pat. Nos. 2,370,567 and 2,403,113. The polyol (allyl carbonate) monomers can be represented by the graphic formula:

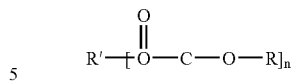

wherein R is the radical derived from an unsaturated alcohol and is commonly an allyl or substituted allyl group, R' is the radical derived from the polyol, and n is a whole number from 2-5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

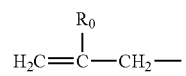

wherein $R_0$ is hydrogen, halogen, or a $C_1$-$C_4$ alkyl group. Specific examples of R include the groups: allyl 2-chloroalyl, 2-bromoalyl, 2-fluoroalyl, 2-methylalyl, 2-ethylalyl, 2-isopropylalyl, 2-n-propylalyl, and 2-n-butylalyl. Most commonly R is the allyl group:

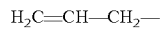

R' is the polyvalent radical derived from the polyol, which can be an aliphatic or aromatic polyol that contains 2, 3, 4 or 5 hydroxy groups. Typically, the polyol contains 2 hydroxy groups, ie a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$-$C_4$) alkylene glycol, ie ethylene glycol, propylene glycol, trimethylene glycol, tetramethylene glycol, or diethylene glycol, triethylene glycol etc.

In a further embodiment, the invention provides a photochromic article comprising a polymeric organic host material selected from the group consisting of poly(methyl methacrylate), poly(ethylene glycol bismethacrylate), poly(ethoxylated bisphenol A dimethacrylate) thermoplastic polycarbonate, poly(vinyl acetate), polyvinylbutyral, polyurethane, and polymers of members of the group consisting of diethylene glycol bi(allylcarbonate) monomers, diethylene glycol dimethacrylate monomers, ethoxylated phenol blsmethylacrylate monomers, diisopropenyl benzene monomers and ethoxylated trimethylol propane triacrylate monomers, and a photochromic amount of a compound of the invention.

The polymeric organic host material is selected from the group consisting of polyacrylates, polymethacrylates, poly ($C_1$-$C_{12}$) alkyl methacrylates, polyoxy(alkylene methacrylates), poly(alkoxylates phenol methacrylates), cellulose acetates, cellulose triacetate, cellulose acetate propionate, cellulose acetate butyrate, poly(vinyl acetate), poly(vinyl alcohol), poly(vinyl chloride) poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methylacrylate monomers, diethylene glycol dimethacrylate monomers, diisopropenyl benzene monomers, alkoxylates polyhydric alcohol monomers and diallylidene pentaerythritol monomers.

The photochromic article may comprise a polymeric organic material which is a homopolymer or copolymer of monomer(s) selected from the group consisting of acrylates, methacrylates, methyl mathacrylate, ethylene glycol bis methacrylate, ethoxylated bisphenol A dimethacrylate, vinyl acetate, vinylbutyral, urethane, thiourethane, diethylene glycol bis(allyl carbonate), diethylene glycol dimethacrylate, diisopropenyl benzene, and ethoxylated trimethyl propane triacrylates.

The photochromic composition of the invention may contain the photochromic compound in a wide range of concentrations depending on the type of photochromic moiety and its intended application. For example in the case of inks in which high colour intensity is required a relatively high concentration of up to 30 wt % photochromic may be required. On the other hand it may be desirable in some cases such as optical articles to use photochromics in very low concentrations to provide a relatively slight change in optical transparency on irradiation. For example, as low as 0.01 mg/g of host resin may be used. Generally the photochromic resin will be present in an amount of from 0.01 mg/g of host resin up to 30 wt % of host resin. More preferably the photochromic compound will be present in an amount of from 0.01 mg/g to 100 mg/g of host matrix and still more preferably from 0.05 mg/g to 100 mg/g of host matrix.

The photochromic article may contain the photochromic compound in an amount of from 0.05 to 10.0 milligram per square centimeter of polymeric organic host material surface to which the photochromic substance(s) is incorporated or applied.

The compounds of the invention may be used in those applications in which the organic photochromic substances may be employed, such as optical lenses, eg, vision correcting ophthalmic lenses and piano lenses, face shields, goggles, visors, camera lenses, windows, mirrors, automotive windshields, jewellery, aircraft and automotive transparencies, e.g., T-roofs, sidelights and backlights, plastic films and sheets, textiles and coatings, e.g. coating compositions. As used herein, coating compositions include polymeric coating composition prepared from materials such as polyurethanes, epoxy resins and other resins used to produce synthetic polymers; paints, i.e., a pigmented liquid or paste used for the decoration, protection and/or the identification of a substrate; and inks, i.e., a pigmented liquid or paste used for writing and printing on substrates, which include paper, glass, ceramics, wood, masonry, textiles, metals and polymeric organic materials. Coating compositions may be used to produce verification marks on security documents, e.g. documents such as banknotes, passport and driver' licenses, for which authentication or verification of authenticity may be desired. Security documents, for indicating exposure to light during photocopying.

Throughout the description and claims of this specification, use of the word "comprise" and variations of the word, such as "comprising" and "comprises", is not intended to exclude other additives, components, integers or steps.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed in Australia before the priority date of each claim of this application.

EXAMPLES

Note on Poly(ethylene glycol) {PEG} Methyl Ethers and Polydimethylsiloxane Oligomers and Naming of Compounds The PEG mono methyl ethers are supplied with an average molecular weight. For example the Aldrich Chemical Company supplies them with average number molecular weights such as 350, 750 etc which approximately but not exactly correspond to 7 PEG units, 16 PEG units etc. Thus the 350 Mn PEG contains a distribution of molecular weights and therefore PEG units. Similar comments can be made about the PDMS oligomers. They are supplied with an average molecular weight. Any number quoted as the number of repeat units of dimethyl siloxane is to be interpreted as an average value. To avoid cumbersome and strictly inaccurate naming, the PEG derivatives will be named on the basis of the Mn of the PEG from which they are derived. The succinic acid derivative from 350 PEG will be "succinic acid mono-PEG(350) ester" and not the formal "Succinic acid mono-(2-{2-[2-(2-{2-[2-(2-methoxy-ethoxy)-ethoxy]-ethoxy}-ethoxy)-ethoxy]-ethoxy}-ethyl) ester" which does not indicate the distribution of chain lengths that exists.

Succinic Acid mono-PEG(350) Ester

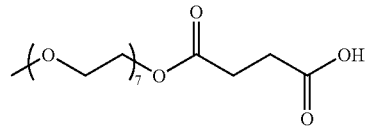

Polyethylene glycol) methyl ether (ie PEG(350) ca 7-PEG unit, Mn ca. 350 g/mol) (20 g, 57.1 mmoles) was dissolved in 50 mL of dichloromethane together with succinic anhydride (5.7 g, 57 mmoles), methanol (100 mg) and dimethylaminopyridine (50 mg) at room temperature under argon. Triethylamine (7.9 mL, 5.7 g, 57.1 mmole) was added dropwise. The reaction was stirred at room temperature for one day and then refluxed for one hour. The reaction was worked up by dilution with dichloromethane, then washed with 2 M HCl and then brine before evaporation under vacuum to give a clear oil as product (19 g, 74%). $^1$H NMR (CDCl$_3$) δ 2.55 (s, 4H, C=O—CH$_2$CH$_2$—C=O), 3.25 (s, 3H, methyl), 3.45 (mult, 2H), 3.55 (s, 22H, PEGs), 3.60 (mult, 2H, CH$_2$CH$_2$—OC=O), 4.15 (mult, 2H, CH$_2$—OC=O) ppm. $^{13}$C NMR (CDCl$_3$) 28.8 & 29.1 (succinyl methylenes), 58.9 (—OCH$_3$), 63.8 & 68.3 (CH$_2$CH$_2$—OC=O), 70.4 (most PEG units), 71.8 (—CH$_2$—O—CH$_3$), 172.2 (ester), 175.0 (acid) ppm.

Succinic Acid mono-PEG(750) Ester

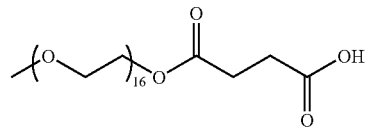

Succinic acid mono-PEG(750) ester was synthesised in a similar manner to succinic acid mono-PEG(350) ester. Yield 79%. ¹H NMR (CDCl₃) δ 2.50 (s, C=O—CH₂CH₂—C=O), 3.25 (s, methyl), 3.50 (s, PEGs), 4.10 (mult, CH₂OC=O) ppm. ¹³C NMR (CDCl₃) 28.7 & 29.0 (succinyl methylenes), 58.9 (—OCH₃), 63.7 and 68.9 (CH₂CH₂—OC=O), 70.4 (most PEG units), 71.8 (—CH₂—O—CH₃), 172.1 (ester), 174.4 (acid) ppm.

Succinic Acid Chloride mono-PEG(350) Ester

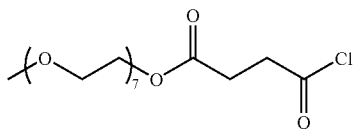

The succinic acid mono-PEG(350) ester (9 g, 20 mmoles) was dissolved in dichloromethane (10 mL) at room temperature under argon and thionyl chloride (3.5 mL) was added dropwise and the reaction stirred for 5 days and then heated at 50-70° C. for 2 hours. The reaction was evaporated under vacuum for one hour at 60° C. The oil was pure acid chloride (9.22 g, 98%). ¹H NMR (CDCl₃) δ 2.55 (t, 2H, CH₂—C=O—CH₂), 3.17 (t, 2H, O—C=O—CH₂), 3.31 (s, 3H, methyl), 3.50 (mult, 2H), 3.60 (s, 22H, PEGs), 4.22 (mult, 2H, CH₂—OC=O) ppm. ¹³C NMR (CDCl₃) 29.3 & 41.7 (succinyl methylenes), 59.0 (—OCH₃), 64.2 & 68.9 (CH₂CH₂—OC=O), 70.5 (most PEG units), 71.9 (—CH₂—O—CH₃), 170.9 (ester), 172.9 (acid chloride) ppm.

Succinic Acid Chloride Mono-PEG(750) Ester

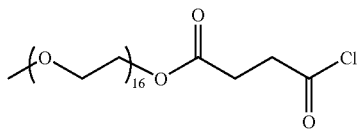

Succinic acid chloride mono-PEG(750) ester was synthesised in the same manner as described for succinic acid chloride mono-PEG(350) ester. Yield 98%. ¹H NMR (CDCl₃) δ 2.52 (t, CH₂—C=O—Cl), 3.03 (t, 2H, O—C=O—CH₂), 3.16 (s, methyl), 3.34 (small mult), 3.44 (s, 22H, PEGs), 3.51 (small mult.), 4.06 (mult, CH₂—OC=O) ppm.

Numbering of Spiro-oxazines

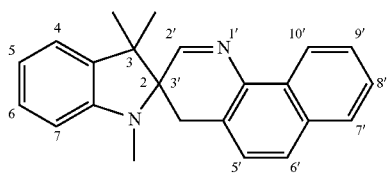

This moiety will be referred to hereinafter by the abbreviation "SOX". The examples are described in part with reference to the drawings (see Examples 8, 23 and 24).

In the drawings:

FIG. 5 is an ROE experiment referred to in Example 1.

FIG. 6 is an ROE experiment of the compound of Example 5.

FIG. 8 is an absorbance graph showing colouration and fade speeds of compound of Example 5.

FIG. 9 is a normalised absorbance graph of the test set up referred to in FIG. 8.

Figure 1:
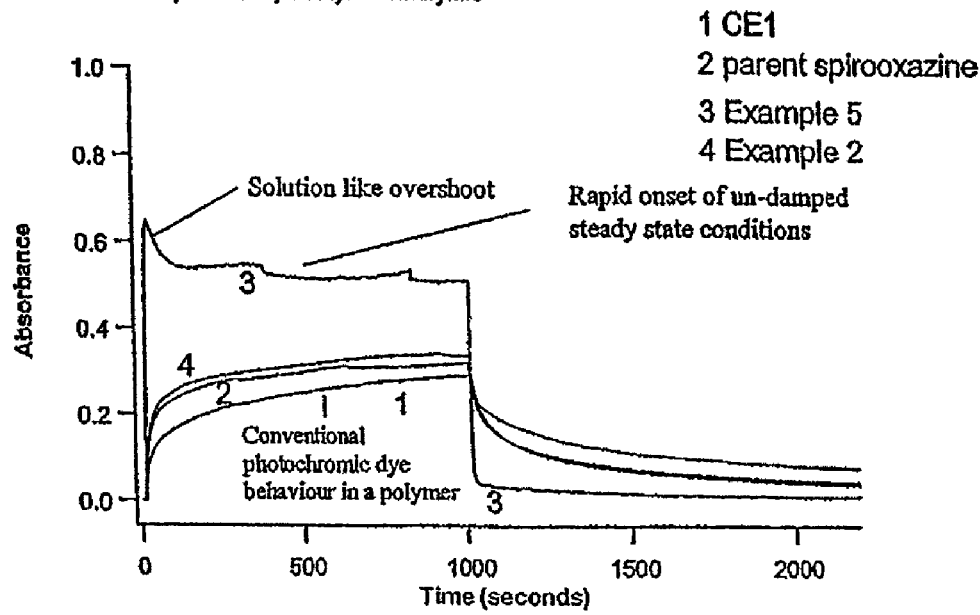
FIG. 1 is a thin film analysis in polymethyl methacrylate matrix comparing the absorbance of the photochromic dyes of Examples 2, 5 and CE1 with the parent dye.
Figure 2:
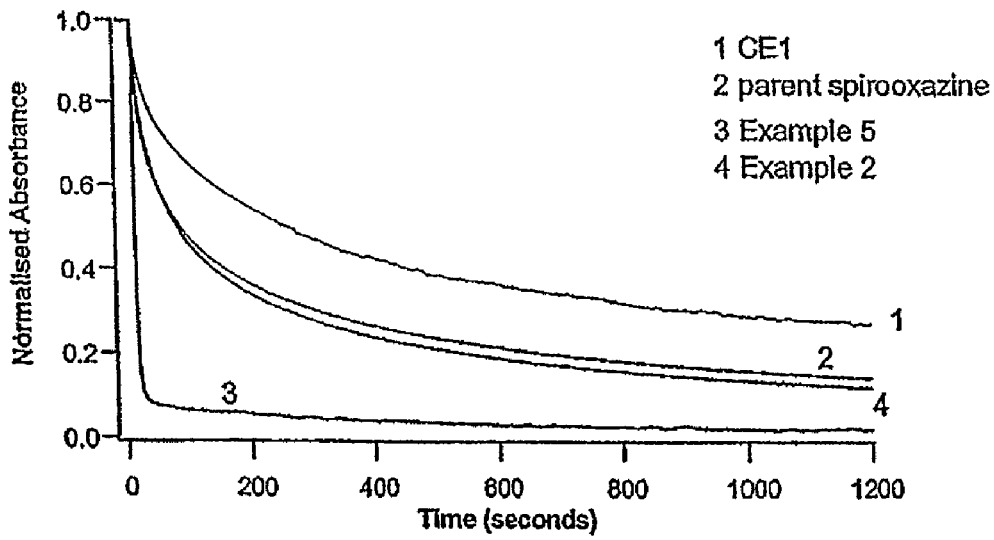
FIG. 2 is the normalised absorbance of compositions referred to in FIG. 1.
Figure 3:
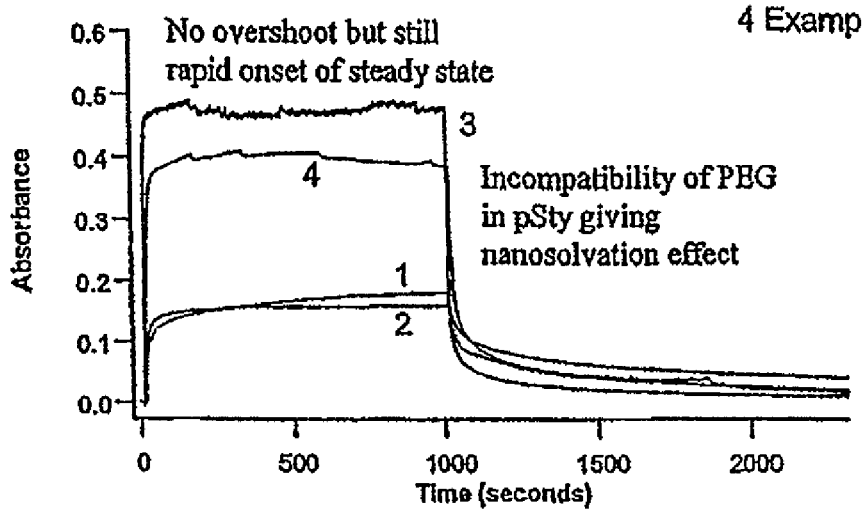
FIG. 3 is a thin film analysis graph comparing the absorbance over time of photochromic dyes of CE1, Example 5 and Example 2 with the parent dye in a polystyrene matrix.
Figure 4:
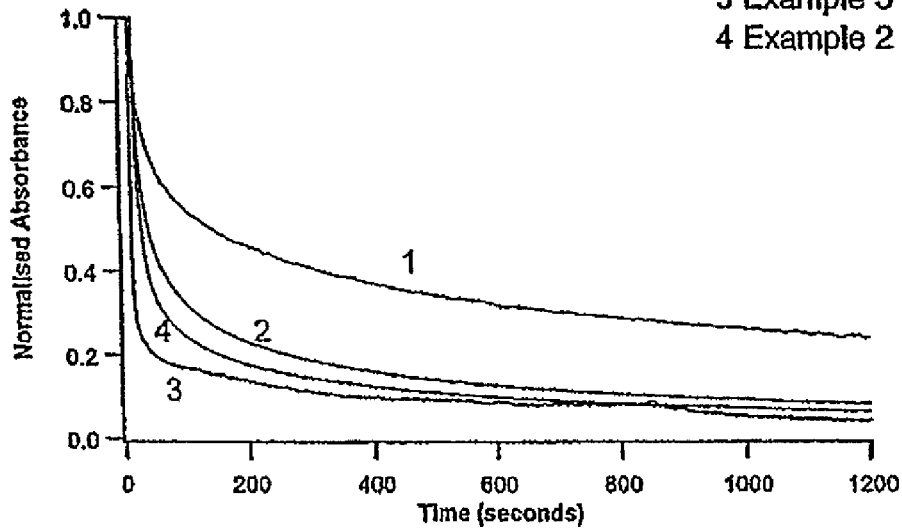
FIG. 4 is a thin film analysis graph sharing the normalised absorbance of the system referred to in FIG. 3.

FIG. 17 is a schematic representative of an instrumental set up for irradiation and absorption measurements of photochromic samples. A number of filters can be integrated into the system to select for ranges of wavelengths exciting the sample. Equally, a monochromator can also be incorporated between the 2 lenses to select for wavelength;

FIG. 18 is a graph of transmission spectra of the filters employed in the experimental set up;

FIG. 19 represents the top view of the Cary 50 sample holder and experimental setup geometrics for films;

FIG. 20 is a chromatograph of Example 18;

FIG. 21 is the chromatograph for Example 20; and

FIG. 22 is the chromatograph for Example 5.

EXAMPLE 1

9'-(PEG(350)-succinyl)-1,3,3-trimethylspiro[indoline-2,3'-[3h]naphtha[2,1-b][1,4]oxazine] (PEG(350)-suc-SOX)

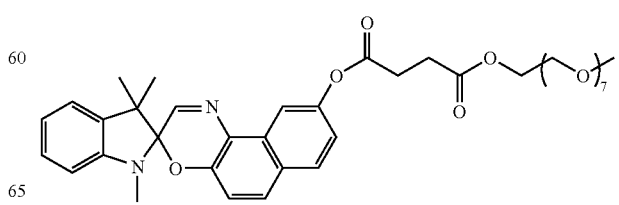

9'-Hydroxy-1,3,3-trimethylspiro[indoline-2,3'-[3H]naph-tha[2,1-h][1,4]oxazine] (1.95 g, 5.67 mmoles) and triethylamine (0.857 g, 1.18 mL, 8.5 mmoles) were added together in dichloromethane (30 mL) and then the succinic acid chloride mono-PEG(350) ester (3.19 g, 6.8 mmol) in dichloromethane was added dropwise to the solution at room temperature under argon protection. When the reaction was complete it was worked up by dilution with dichloromethane, washing with dilute sodium hydroxide, dilute HCl, and brine before final drying with magnesium sulphate to give a dark brown oil (4 g) which was purified by column chromatography to give a brown oil. $^1$H NMR (CDCl$_3$) δ 1.33 (s, 6H, C(CH$_3$)$_2$), 2.75 (s, 3H, N—CH$_3$), 2.82 & 2.94 (mulls, 4M, C=O—CH$_2$CH$_2$—C=O), 3.35 (s, 3H, O—CH$_5$), 3.53 (mutt, 2H, CH$_2$—O—CH$_3$), 3.63 (s, PEG units), 3.71 (mult, CH$_2$CH$_2$O—C=O), 4.30 (mull, 2H, CH$_2$CH$_2$O—C=O), 6.58 (d, J=7.6 Hz, 5-H), 6.82-7.27, 7.59-7.79, 8.23 (d, H=2.7 Hz. 7'-H) ppm.

EXAMPLE 2

9'-(PEG(750)-succinyl)-1,3,3-trimethylspiro[indoline-2,3'-[3H]naphtha[2,1-b][1,4]oxazine] (PEG(750)-suc-SOX)

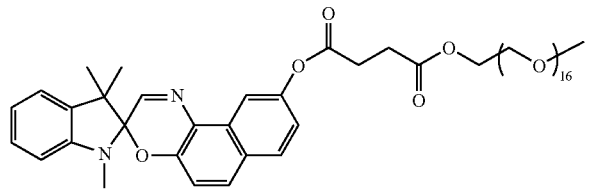

9'-(PEG(750)-succinyl)-1,3,3-trimethylspiro[indoline-2,3'-[3H]naphtha[2,1-b][1,4]oxazine] was synthesised in the same manner as 9'-(PEG(350)-succinyl)-1,3,3-trimethylspiro[indoline-2,3'-[3H]naphtha[2,1-b][1,4]oxazine] using succinic acid chloride mono-PEG(750) ester in place of succinic acid chloride mono-PEG(350) ester to give 76% yield of product. The $^1$H NMR spectrum looked the same as 9'-(PEG(350)-succinyl)-1,3,3-trimethylspiro[indoline-2,3'-[3H]naphtha[2,1-b][1,4]oxazine] except it had a correspondingly larger singlet for the PEG units at 3.63 ppm. $^1$H NMR (CDCl$_3$) δ 1.33 (s, 6H, C(CH$_3$)$_2$), 2.75 (s, 3H, N—CH$_3$), 2.82 & 2.94 (molts, 4H, C=O—CH$_2$CH$_2$—C=O), 3.35 (5, 3H, O—CH$_3$), 3.53 (mutt, 2H, CH$_2$—O—CH$_3$), 3.63 (s, PEG units), 3.71 (mull, 2H. CH$_2$CH$_2$O—C=O), 4.30 (mutt, 2H, CH$_2$CH$_2$O—C=O), 6.58 (d, J=7.6 Hz, 5-H), 6.82-7.27, 7.59-7.79. 8.23 (d, H=2.7 Hz, 7'-H) ppm.

EXAMPLE 3

Part (a)

5,9'-Dihydroxy-1,3,3-trimethylspiro[indoline-2,3'-[3H]naphtha[2,1-b][1,4]oxazine]

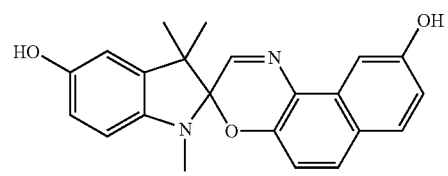

5-Hydroxy-1,2,3,3-tetramethylindolium iodide (1.65 g, 5.2 mmoles) was dissolved in methanol (10 mL) and butanone (5 mL) and piperidine (0.5 mL) were added dropwise and the solution let stand. Then 2,7-dihydroxy-1-nitrosonaphthalene (0.983 g) was added and the solution was refluxed for an hour and then let stir overnight at room temperature. The solvents were evaporated and the residue was chromatographed to give a drak blue product (300 mg 17%). $^1$H NMR (DMSO-d$_6$) δ 1.20 & 1.27 (s, 3H, methyl), 2.57 (s, 3H, N-Me), 6.37-6.61 (mult aromatic), 6.61-6.76 (mult aromatic), 0.58-0.98 (mult.aromatic), 8.80 (naphthyl aromatic), 9.88 (naphthyl aromatic) ppm.

Part (b)

5,9'-DI(PEG(350)-succinyl)-1,3,3-trimethylspiro[indulines-2,3'-[3H]naphtha[2,1-b][1,4]oxazine] (BisPEG(350)-suc)-SOX)

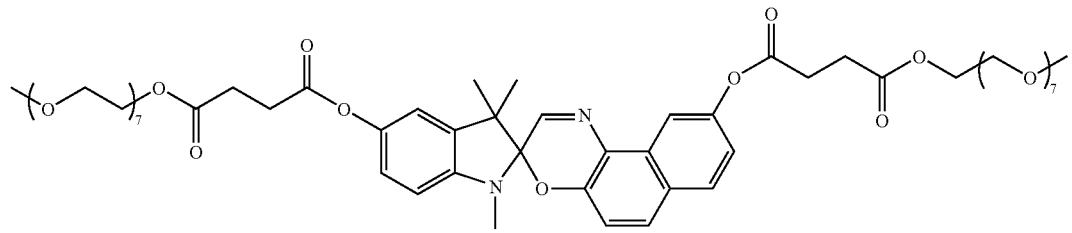

5,9'-Di(PEG(350)-succinyl)-1,3,3-trimethylspiro[indoline-2,3'-[3H]naphtha[2,1-b][1,4]oxazine] was made in the same way as 9'-(PEG(350)-succinyl)-1,3,3-trimethylspiro[indoline-2,3'-[3H]naphtha[2,1-b][1,4]oxazine using 2 molar equivalents of succinic acid chloride mono-PEG(350). The product was a brown oil (90% yield). $^1$H NMR (CDCl$_3$) δ 1.00 (s, 3H, methyl), 1.13 (s, 3H, methyl), 2.38 (s, 3H, N-methyl), 2.49 (mult, 8H, C=O—CH$_2$CH$_2$—C=O), 3.10 (s, 6H, O—CH$_3$), 3.40 (s, ca 12-14 full PEG units+2×½ PEG units), 4.12 (s, 4H, CH$_2$CH$_2$O—C=O), 6.18 (d, J=8.2 Hz, 5-H), 6.73-7.0 (mult. aromatic), 7.2-7.6 (mult. aromatic), 8.55 & 8.82 (s, naphthyl aromatic) ppm.

EXAMPLE 4

Poly(dimethylsiloxane) monocarboxydecoyl chloride terminated

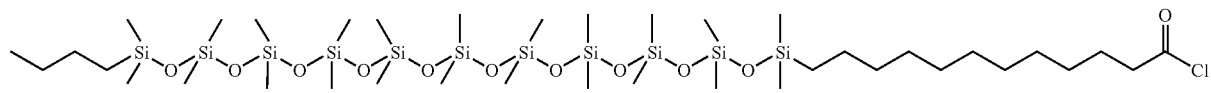

Poly(dimethylsiloxane) monocarboxydecyl (MCR-B11 ABCR Mw ca 1056)) (4 g, 4 mmole) was dissolved in 10 mL of dichloromethane, thionyl chloride (2 mL) was added and the reaction heated under argon overnight. The reaction was worked up by evaporation of solvent and thionyl chloride under vacuum and mild heating (40° C.) to give 3.77 g (94%) of very pale amber oil. $^1$H NMR (CDCl$_3$) δ 0.0 (s, Si—Me), 0.45 (m, CH$_2$), 0.8 (t, J=ca. 6.6 Hz, CH$_3$), 1.2 (s, CH$_2$), 1.6(pent, 2H, CH$_2$—CH$_2$—COCl), 2.8 (t, J=7 Hz, 2H, CH$_2$—CH$_2$—COCl). 13C NMR (CDCl$_3$) δ 0.18, 1.05, 1.18, 1.78, 13.8, 18.0, 18.3, 23.2, 25.07, 25.5, 26.4, 28.5, 29.1, 29.4, 29.48, 33.4, 47.1 (CH2—COCl), 173.7 (COCl) ppm.

EXAMPLE 5

9'-(PDMS(855)-undecoyl)-1,3,3-trimethylspiro[indoline-2,3'-3h]naphtha[2,1-b][1,4]oxazine]

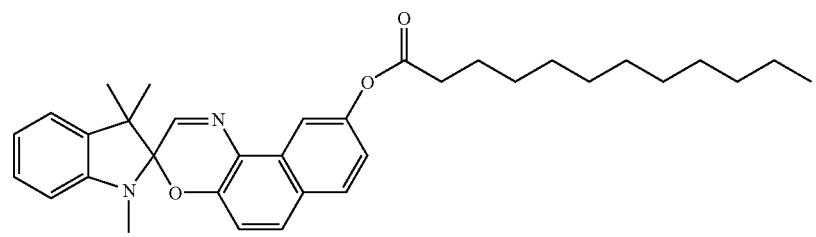

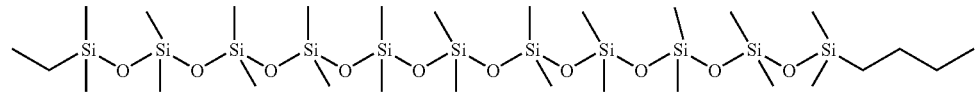

9'-Hydroxy-1,3,3-trimethylspiro[indoline-2,3'-[3H]naphtha[2,1-b][1,4]oxazine] (1 g, 2.9 mmoles) and triethylamine (0.9 mL, 655 mg, 6.5 mmoles) were added together in dichloromethane (20 mL) and then poly(dimethylsiloxane) monocarboxydecoyl chloride terminated (3.0 g, 2.8 mmol) in dichloromethane was added dropwise to the solution at room temperature under argon protection. The reaction was monitored by tlc (DCM or ether:hexane 1:1) and was completed after a few hours. The reaction was worked up by washing with water, brine (plus a little of v dilute HCl to break the emulsion), dried (MgSO$_4$) before evaporation to a dark liquid. The oil was chromatographed on silica with ether:hexane (1:3) to give 2.1 g (52%) of pale brown green oil as the desired product. A second slower fraction (200 mg) was obtained that was spectroscopically similar to the product except it had a vinyl (terminal) group and had much less DMS content. $^1$H NMR (acetone-d$_6$) δ=0.09 (d, J=1.8 Hz, Si-Me), 0.10 (d, J=1.83 Hz, Si-Me), 0.12 (d, J=1.8 Hz, Si-Me), 0.13 (s, Si—Me), 0.6 (mult., 4H, alkyl), 0.90 (mult., 4H, alkyl), 1.3-1.4 (mult, 22H, 9,10-H, alkyl, CH$_2$—CH$_3$), 1.50 (mult, 2H, 'c'-H), 1.80 (pent., J=7.3 Hz), 2H, 'b'-H), 2.68 (t, J=7.3 Hz, 2H, 'a'-H), 2.77 (s, 3H, 8-H), 6.65 (d, J=7.8 Hz, 7-H), 6.87 (t, J=7.3 Hz, 5-H), 7.03 (d, J=8.5 Hz, 5'-H), 7.14 (d, J=7.3 Hz, 4-H), 7.19 (apparent t, 2H, 6 & 8'-H), 7.80 (d, J=9.3 Hz, 6'-H), 7.82 (s, 2'H), 7.86 (d, J=8.6 Hz, 7'-H), 8.23 (d, J=2.3 Hz, 10'-H) ppm. MS (FAB), M+1368 (100%) (corresponds to 11 DMS units in oligomer), 1145.9 (90%)(corresponds to 8 DMS units in oligomer), 1591.4 (85%)(corresponds to 14 DMS units in oligomer, 923.6 (corresponds to 5 DMS units in oligomer), 1813.5 (corresponds to 17 DMS units in oligomer). Peaks for all other oligomer lengths between 4-19 DMS units were also observed in a small bell curve distribution centred around 12 DMS units (12 MDS 40% of M+ with other peaks being smaller).

EXAMPLE 6

9'-((1-(Isobutyl)-POSS)-3-propyl)-succinyl)-1,3,3-trimethylspiro[indoline-2,3'-[3h]naphtha[2,1-b][1,4]oxazine]

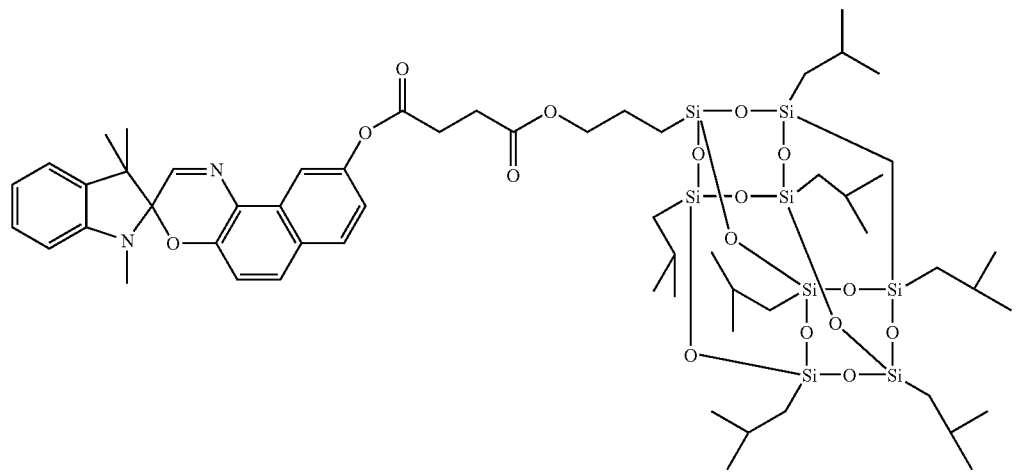

9-(Monocarboxy-succinyl)-1,3,3-trimethylspiro[indoline-2,3'-[3h]naphtha[2,1-b][1,4]oxazine (0.62 g 1.8 mmoles), hydroxypropylisobutyl-POSS (1.58 g 1.8 mmoles), dimethylaminopyridine (33 mg, 0.2 mmoles) were dissolved in dichloromethane (15 mL) and then dicyclohexylcarbodiimide (0.4 g, 1.8 mmoles) in dichloromethane was added slowly over five minutes. The solution was refluxed under argon for 4-5 hours until tlc analysis showed no starting spirooxazine was present. Product was identified on tlc as a fast moving band (ether:hexane 1:1 rf ca. 0.8). The reaction was worked up by dilution with dichloromethane (to 100 mL), cooling and filtering off the precipitated dicyclohexyl urea. The solution was washed with water, brine, dried and evaporated to give a white solid. This was chromatographed on silica (ether:hexane 1:3) until the fast moving light blue band was eluted. The solvent was evaporated from the collected band to give a white/pale green/blue solid (0.86 g, 37%). The column was eluted with ether:hexane (1:1) to give two more bands. These were evaporated to give a smear and a non-photochromic solid. The material was purified by reverse phase chromatography to give a crystalline material that displayed photochromism in the crystalline state. It turned blue when irradiated with ultra violet light. MS (1E) 1302 (M+., 100%). δ≠0.65 (14H, dd J 2.19, 6.95), 0.75 (2H, t J 8.23), 0.98 (42H, bs), 1.34 (3H, s), 1.36 (3H, s), 1.75-1.97 (9H, m), 2.77 (3H, s), 2.80 (2H, t J 6.40) 3.0 (2H, t J 6.40), 4.12 (2H, t J 6.79), 6.66 (1H, d J 7.68), 6.87 (1H, dd J 0.73, 7.32), 7.05 (1H, d J 8.78), 7.15 (1H, d J 7.32), 7.17-7.22 (2H, m), 7.82 (1H, d J 8.78), 7.83 (1H, s), 7.88 (1H, d J 8.78), 8.26 (1H, d J 2.38) ppm.

EXAMPLE 7

A simple screen for examining photochromic speed was carried out as follows: A small quantitly of the photochromic compound was dissolved in THF to give a concentration of ca 25 mmol per milliliter. This solution was then dropped onto normal photocopy paper (brand "Reflex") to give a spot of about 1-2 cm in diameter. This was allowed to dry. The spot was then irradiated with a hand held UV light (365 nm) and the spot would colorize and then decolorize when the UV light was removed. When spots of the parent SOX, CE1, Example 1, and Example 2 were examined simultaneously it was obvious to the eye that the Example 1 and Example 2 decolourised in less than 15 seconds whereas the conventional dyes (parent SOX and CE1) were still decolourising after 5 minutes. In addition, the conventional dyes would fatigue after 3-4 hours such that no colouration was observed after about 4 hours. However, the Example 1 and Example 2 dyes were protected from fatigue for an extended period. Typically, photochromism was observed for at least a week.

EXAMPLE 8

Steady state UV-Visible absorption measurements in Table 5 were collected using a Varian Cary 50 UV-visible Spectrophotometer. The instrument allows for the in-situ excitation of samples and hence the study of "real-time" changes in absorption of solutions and films. The Cary 50 is equipped with a thermostatted peltier sample holder allowing an operating temperature range of −10°-100° C.

FIG. 17 Instrumental setup for irradiation and absorption measurements of photochromic samples. A number of filters can be integrated into the system to select for ranges of wavelengths exciting the sample. Equally, a monochromator can also be incorporated between the 2 lenses to select for wavelength.

Samples were photoexcited by exposure to a 150 W Xenon Arc lamp. The excitation wavelength range was restricted to approximately 300-400 nm and above 650 nm by the use of two optical filters, WG 320 and 9863 (see FIG. 18). A water filter was also used to reduce thermal heating of the sample.

Films of the photochromic compounds (approximately 0.3 g.L$^{-1}$) were cast from a 4% w/v solution of polymer dissolved in a suitable solvent onto glass slides and air dried. Films were approximately 100° m thick.

Film samples were mounted in the spectrophotometer with a particular geometry (see FIG. 19). The face of the film was pointing away from the detector to minimise scattered excitation light saturating the detector. Another cut-off filter (GG495) was used immediately in front of the detector to further minimise scattered UV light reaching the detector.

FIG. 18: Transmission spectra of the filters employed in the experimental setup.

FIG. 19: Top view of the Cary 50 sample holder and experimental setup geometries for films.

Samples were allowed to thermally equilibrate at each temperature for about five minutes before scans were performed.

The absorbance ($A_0$), the half lives for discolouration ($t_{1/2}$, sec) and the three quarter lives ($t_{3/4}$,S) for discolouration for several photochromic compounds in different polymer films are given in Table 5. $T_{1/2}$ is the time taken for the optical density to reduce by half from the initial maximum optical density of the coloured from when UV irradiation is stopped. $T_{3/4}$ is time taken for the optical density to reduce by three quarters from the initial maximum optical density of the coloured form of the dye from when UV irradiation is stopped.

TABLE 5

| 2 | Oxford Blue [N-isobutyl-SOX] | 0.218 | 63 | 302 | 0.196 | 91 | 473 | 0.231 | 193 | 1128 |
|---|---|---|---|---|---|---|---|---|---|---|
| 3 | PEG(350)-SOX (Example 1) | 0.201 | 58 | 233 | 0.222 | 46 | 270 | 0.200 | 144 | 922 |
| 4 | PEG (750)-SOX (Example 2) | 0.253 | 44 | 228 | 0.153 | 39 | 247 | 0.195 | 93 | 614 |
| 5 | Bis Propyl-SOX | 0.155 | 110 | 555 | 0.046 | 207 | 1284 | 0.191 | 367 | 2663 |
| 6 | Bis PEG (350)-SOX (Example 3) | 0.237 | 83 | 382 | 0.115 | 49 | 402 | 0.143 | 412 | 2534 |

TABLE 5-continued

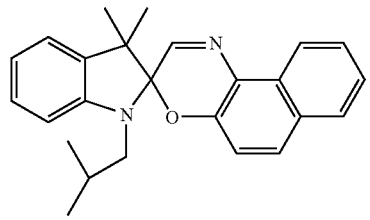

Oxford Blue
n-Isobuyl-SOX

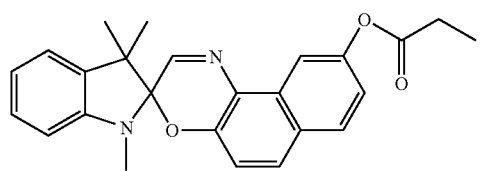

propyl-SOX

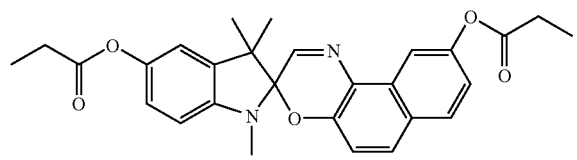

bis-propyl-SOX

Examples of the control of the fade speed by choice of oligomer and matrix can be seen in Table 5. Rows 3 and 4 show the fade enhancement of spirooxazine photochromic agents functionalised by polar polyethylene gycol (PEG) chains of increasing length respectively. Example 2 shows enhanced fade speed relative to reference compounds in rows 1 and 2 in poly(methyl methacrylate), poly(styrene) and poly (carbonate). Furthermore it is apparent that the longer the oligomer length, the better the encapsulation effect with Example 2 (row 4) fading faster than Example 1 (row 3) in all three polymers. PEG(750) has approximately 16 PEG units while PEG(350) has approximately 7. In this case of Example 2 the fade speed has almost become independent of the host matrix.

The encapsulation effect can be seen clearly in the case of Example 3 (Table 5 row 6). Here the fade speed in poly (styrene) is significantly faster than poly(methylmethacrylate) as the PEG chains will be incompatible with the polystyrene matrix and coil close to or encapsulate the photochromic. The poly(styrene) fade speed is similar to that of Example 1. However, in polymethyl methacrylate the PEG chains of Example 3 are more compatible with the matrix and the $T_{1/2}$ fade speed slows to be significantly slower as Example 1. The bis-propylate-SOX also shows this effect with a short alkyl chain. Here the non-polar alkyl chain will be incompatible with polar poly(methyl methacrylate) matrix but more compatible with non-polar poly(styrene) and so fade speed is much slower in poly(styrene). Both Example 3 and bis-propyl-SOX show very slow fade speed in polycarbonate.

Kinetic Curves

The following kinetic curves (FIGS. 1 to 4) were obtained using different films and under different conditions to those used for acquiring the data in Table 5. The experimental set up used is described in Example 24. The curves show the dramatic effect of the PDMS oligomer attached to a photochromic dye on fade speed of the photochromic dye It provides solution-like kinetic behaviour not previously observed for a photochromic dye in a polymer matrix. It allows rapid colouration to a constant maximum optical density followed by a rapid fade on cessation of irradiation. Similar effects are found with the PEG oligomer in Example 2 (SOX-suc-PEG (750)). When it is placed in a matrix that the PEG will have some incompatability [ie polystyrene] the PEG then is more available to solvate the photochromic dye and a fast fade is observed. CE1 (SOX-propylate) is electronically identical to both the Example 5 (SOX-undec-PDMS (855)) and Example 2 (SOX-suc-PEG(750)) and shows dramatically slower colouration and fade kinetics as there is no oligomer to provide a favourable switching environment.

The following curves (FIGS. 1 to 4) show the colouration and fade performance of the Example 2 (SOX-suc-PEG (750)), Example 5 (SOX-undec-PDMS (855)) in comparison with the electronically identical SOX-Propylate and parent dye (no substituents) in poly(methylmethacrylate) and poly (styrene) respectively. They show that the PDMS oligomer allows the dye to rapidly colourise and achieve a maximum optical density within tens of seconds. Conventional dyes like the CE1 (SOX-propylate) (which is electronically identical to the Example 5 (SOX-undec-PDMS (855)) and parent SOX (1,3-dihydro-1,3,3-trimethyl-spiro[2H-indole-2,3'-[3H]- naphth[2,1-b][1,4]oxazine]) typically colourise slowly and continue to do so even after 100 seconds.

The normalised fade curves focus on the fade kinetics. It is obvious to the eye that the Example 5 (SOX-undec-(PDMS (855)) undergoes fade far faster than any of the conventional dyes and reaches low if not actually 0.0 absorbance within a minute whereas the conventional dyes still have significant absorbance after 1000 secs and longer.

The PDMS is providing a highly mobile local environment for switching behaviour. Without wishing to be bound by theory it is thought that its incompatibility with the matrix allows it to aggregate near or around the dye and so provides protection from the rigidity of the bulk matrix. This occurs in poly(styrene), poly(methylmethacrylate) and poly(carbonate) where it shows the same behaviour in all the matrices. The behaviour of the dye is similar to that observed in solution. It shows rapid coloration with an initial overshoot and then rapidly reaches a constant optical density, shows undamped kinetic behaviour and then rapid fade when irradiation stops.

EXAMPLE 9

5-(PDMS(855)-undecoyl)-1,3,3-trimethylspiro[indoline-2,3'-[3H]napth[2,1-b][1,4]oxazine]

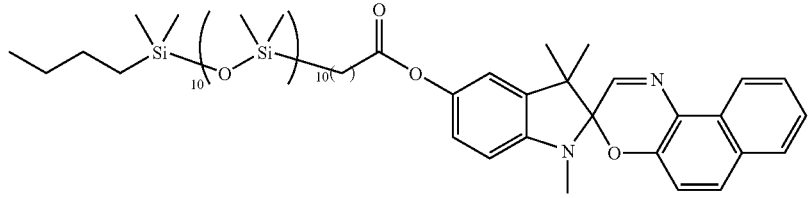

PDMS(855)-undec-SOX 5-(PDMS(855)-undecoyl)-1,3,3-trimethylspiro[indoline-2,3'-[3H]napth[2,1-b][1,4]oxazine]was synthesised according to the procedure for the preparation of 9'-(PDMS(855)-undecoyl)-1,3,3-trimethylspiro[indoline-2,3'-[3H]napth[2,1-b][1,4]oxazine] (Example 5) using 5-hydroxy-1,3,3-trimethylspiro[indoline-2,3'-[3H]napth[2,1-b][1,4]oxazine] in place of 9'-hydroxy-1,3,3-trimethylspiro [indoline-2,3'-[3H]napth[2,1-b][1,4]oxazine], column chromatography (silica) 1: 20, ethyl acetate:hexane (51%). $^1$H NMR($C_2D_6O$) δ≠0.1 (bs), 0.58 (4H, m), 0.89 (4H, m), 1.21-1.52 (242H, m), 1.72 (2H, m), 2.55 (2H, t, J 7.31), 2.76 (3H, s), 6.63 (1H, d, J 9.14), 6.88 (1H, d, J 2.19), 6.92 (1H, d, J 2.19), 7.07 (1H, d, J 8.77), 7.42 (1H, dd, J 8.41, 1.46), 7.59 (1H, dd, J 8.41, 1.46), 7.74-7.88 (3H, m), 8.85 (1H, d, J 8.41) ppm. $^{13}$C NMR ($C_2D_6O$) δ≠ 172.8, 151.5, 146.1, 145.6, 144.8, 137.8, 131.8, 131.2, 130.4, 128.7, 127.8, 125.0, 122.4, 121.5, 117.5, 116.5, 107.9, 99.8, 52.5, 34.7, 34.2, 30.3, 30.1, 30.0, 27.1, 26.2, 25.7, 25.6, 24.0, 20.9, 18.9, 18.6, 14.2, 1.4 ppm.

EXAMPLE 10

6'-Cyano-5-(PDMS(855)-undecoyl)-1,3,3-trimethyl-spiro[indoline-2,3'-[3H]napth[2,1-b][1,4]oxazine]

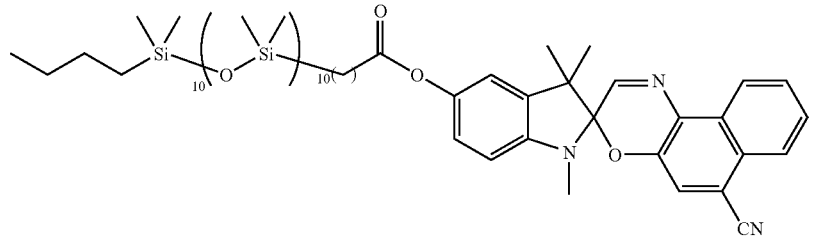

PDMS(855)-undec-SOX-cyano

6'-Cyano-5-(PDMS(855)-undecoyl)-1,3,3-trimethylspiro[indoline-2,3'-[3H]napth[2,1-b][1,4]oxazine] was synthesised according to the procedure for the preparation of 9'-(PDMS(855)-undecoyl)-1,3,3-trimethylspiro[indoline-2,3'-[3H]napth[2,1-b][1,4]oxazine] (Example 5) using 6'-cyano-5-hydroxy-1,3,3-trimethylspiro[indoline-2,3'-[3H]napth[2,1-b][1,4]oxazine] in place of 9'-hydroxy-1,3,3-trimethylspiro[indoline-2,3'-[3H]napth[2,1-b][1,4]oxazine], column chromatography (silica) 1:20, ethyl acetate:hexane (68%). $^1$H NMR($C_2D_6O$) δ=0.11 (bs), 0.60 (4H, m), 0.90 (3H, m), 1.24-1.51 (24H, m), 1.72 (2H, m), 2.56 (2H, t, J 7.31), 2.78 (1H, s), 6.65 (1H, d, J 9.5), 6.91 (1H, s,), 6.94 (1H, s), 7.63-7.83 (3H, m), 8.04 (1H, s), 8.10 (1H, d, J 8.04), 8.71 (1H, d, J 8.04) ppm. $^{13}$C NMR($C_2D_6O$) δ=172.8, 155.4, 145.9, 145.8, 144.0, 137.4, 131.5, 129.3, 127.7, 125.5, 124.4, 123.5, 121.7, 117.4, 116.6, 111.8, 108.2, 100.2, 71.7, 53.0, 34.7, 34.3, 30.3, 30.1, 30.1, 27.1, 26.2, 25.7, 25.6, 24.0, 20.9, 18.9, 18.6, 14.2, 1.5 ppm.

EXAMPLE 11

5-Methoxy-9'-(PDMS(855)-undecoyl)-1,3,3-trimethylspiro[indoline-2,3'-[3H]napth[2,1-b][1,4]oxazine]

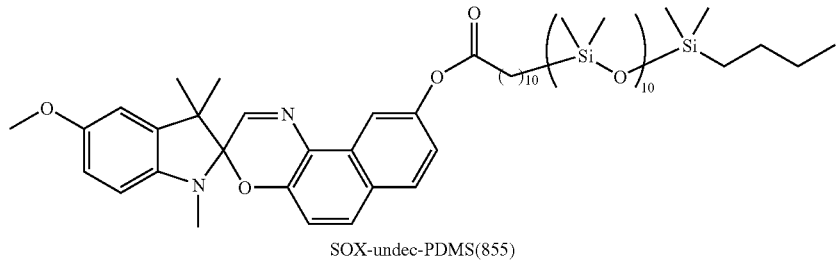

Ex. 11

SOX-undec-PDMS(855)

5-Methoxy-9'-(PDMS(855)-undecoyl)-1,3,3-trimethylspiro[indoline-2,3'-[3H]napth[2,1-b][1,4]oxazine] was synthesised according to the procedure for the preparation of 9'-(PDMS(855)-undecoyl)-1,3,3-trimethylspiro[indoline-2,3'-[3H]napth[2,1-b][1,4]oxazine] (Example 5) using 5-methoxy-9'-hydroxy-1,3,3-trimethylspiro[indoline-2,3'-[3H]napth[2,1-b][1,4]oxazine] in place of 9'-hydroxy-1,3,3-trimethylspiro[indoline-2,3'-[3H]napth[2,1-b][1,4]oxazine], column chromatography (silica) 1:20, ethyl acetate:hexane (75%). $^1$H NMR($C_2D_6O$) δ≠0.10 (bs), 0.59 (4H, m), 0.90 (3H, m), 1.24-1.55 (22 h, m), 1.79 (2H, m), 2.69 (3H, s), 2.80 (3H, s), 3.77 (1H, s), 6.57 (1H, d, J 8.77), 6.73 (1H, d, J 2.19), 6.81 (1H, d, J 2.19), 7.04 (1H, d, J 8.77), 7.18 (1H, dd, J 8.77, 2.19), 7.77-7.92 (3H, m), 8.22 (1H, d, J 2.19) ppm. $^{13}$C NMR($C_2D_6O$) δ≠172.5, 155.5, 151.8, 151.0, 145.7, 142.6, 138.2, 132.7, 130.9, 130.2, 128.1, 123.8, 120.5, 117.2, 113.7, 112.7, 110.0, 108.4, 100.1, 56.1, 52.7, 34.8, 34.3, 30.4, 30.2, 30.2, 27.1, 26.3, 25.7, 24.1, 20.9, 19.0, 18.6, 14.2, 1.5 ppm.

EXAMPLE 12

2-(9'-(PDMS(855)-undecoyl)oxy-ethyl ester)-1,3,3-trimethylspiro[indoline-2,3'-[3H]napth[2,1-b][1,4]oxazine]

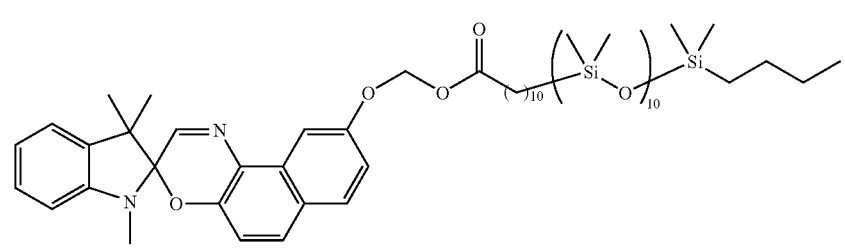

Ex. 12

SOX-ethoxy-undec-PDMS(855)

2-(9'-(PDMS(855)-undecoyl) oxy-ethyl ester)-1,3,3-trimethylspiro[indoline-2,3'-[3H]napth[2,1-b][1,4]oxazine] was synthesised according to the procedure for the preparation of 9'-(PDMS(855)-undecoyl)-1,3,3-trimethylspiro[indoline-2,3'-[3H]napth[2,1-b][1,4]oxazine] (Example 5) using 2-(9'-oxyethanol)-1,3,3,-trimethylspiro[indoline-2,3'-[3H]napth[2,1-b][1,4]oxazine] in place of 9'-hydroxy-1,3,3-trimethylspiro[indoline-2,3'-[3H]napth[2,1-b][1,4]oxazine]. $^1$H NMR($C_2D_6O$) δ=0.10 (bs), 0.58 (4H, m), 0.89 (3H, m), 1.24-1.49 (22H, m), 1.78 (2H, m), 2.51 (2H, t, J 7.31), 2.68 (2H, t, J 7.31), 2.77 (3H, s), 6.65 (1H, d, J 7.68), 6.73 (1H, dd, J 1.96), 7.04 (1H, d, J 8.77), 7.10-7.24 (3H, m), 7.75-7.93 (3H, m), 8.23 (1H, d, J 2.56) ppm. $^{13}$C NMR($C_2D_6O$) δ=170.3, 152.0, 151.0, 136.7, 132.6, 130.9, 130.2, 128.8, 128.1, 122.3, 120.7, 120.5, 117.2, 113.7, 108.0, 99.7, 52.5, 34.8, 34.2, 30.3, 30.2, 30.1, 29.9, 29.8, 28.7, 27.1, 26.2, 25.8, 25.7, 24.0, 21.0, 18.9, 18.6, 14.8, 14.2, 1.4 ppm.

EXAMPLE 13

5-methyl carboxylate-6-(PDMS(855)-undecoyl)-2,2-bis(4-methoxyphenyl)-2H-napthol[1,2-b]pyran

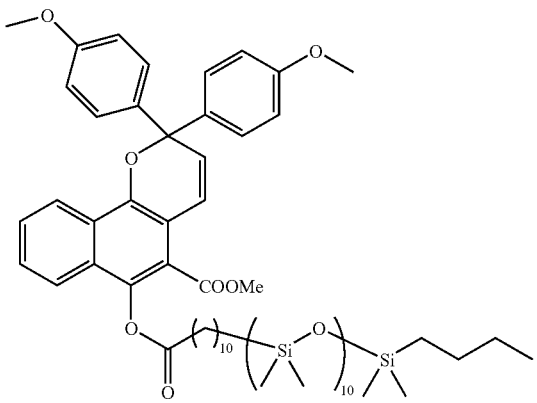

Ex. 13

A solution of the poly(dimethylsiloxane) monocarboxydecoyl chloride (0.78 g, 7.34×10$^{-4}$ mol) in dichloromethane (5 mL) was slowly added to a solution of 5-methyl carboxylate-6-hydroxy-2,2-bis(4-dimethoxyphenyl)-2H-naptho[1,2-b]pyran (0.29 g, 6.2×10$^{-4}$ mol) and triethylamine (0.12 g, 1.22 mmol) in dichloromethane (10 mL) The solution was stirred at room temperature under $N_2$ for 2 hour. Water (20 mL) was added and the solution was extracted, dichloromethane (3×20 mL), followed by removal of the solvent in vacuo then chromatography (silica, 5:1 hexane/ethyl acetate) to give a red viscous oil (0.89 g, 96%). $^1$H NMR($C_2D_6O$) δ=0.10 (bs), 0.59 (4H, m), 0.90 (3H, m), 1.34 (24H, m), 1.77 (2H, m), 2.74 (2H, t, J 7.68), 3.75 (6H, s), 3.93 (3H, s), 6.40 (1H, d, J 10.23), 6.95 (1H, d, J 8.77), 7.44 (4H, d, J 8.77), 7.53-7.72 (2H, m) 7.84 (1H, d, J 8.41), 8.41 (1H, d, J 7.68) ppm. $^{13}$C NMR($C_2D_6O$) δ=172.2, 166.3, 160.1, 146.7, 140.3, 137.7, 130.2, 128.9, 128.7, 128.5, 128.3, 127.1, 123.5, 123.1, 121.7, 120.9, 114.3, 83.5, 55.5, 52.8, 34.3, 30.4, 30.2, 30.2, 27.1, 26.3, 25.6, 24.1, 19.0, 18.7, 14.3, 1.6, 1.5 ppm.

EXAMPLE 14

5-Methyl carboxylate-6-(PDMS(855)-undecoyl)-2,2-(4-methoxyphenyl)-2H-napthol[1,2-b]pyran Ex. 14

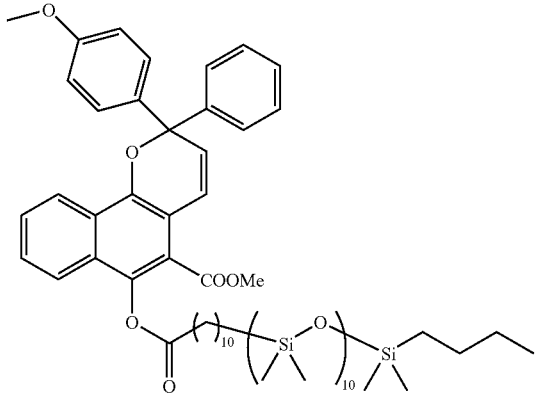

5-Methyl carboxylate-6-(PDMS(855)-undecoyl)-2,2-(4-methoxyphenyl)-2H-napthol[1,2-b]pyran was synthesised according to the procedure for 5-methyl carboxylate-6-poly(dimethylsiloxane)-undecyl-2,2-bis(4-methoxyphenyl)-2H-napthol[1,2-b]pyran (Example 13) using 5-methyl carboxylate-6-hydroxy-2,2-(4-methoxyphenyl)-2H-naptho[1,2-b]pyran in place of 5-methyl carboxylate-6-hydroxy-2,2-bis(4-dimethoxyphenyl)-2H-naptho[1,2-b]pyran. $^1$H NMR ($C_2D_6O$) δ=0.09 (bs), 0.58 (4H, m), 0.89 (4H, m), 1.35 (22H, m), 1.77 (2H, m), 2.75 (2H, t, J 7.31), 3.75 (3H, s), 3.93 (3H, s), 6.46 (1H, d, J 10.23), 6.88 (2H, d, J 8.77), 6.99 (1H, d, J 10.23), 7.21-7.42 (3H, m), 7.47 (2H, d, J 8.77), 7.51-7.74 (4H, m), 7.85 (1H, d, J 7.67), 8.45 (1H, d, J 7.67) ppm. $^{13}$C NMR($C_2D_6O$) δ=172.2, 166.3, 160.2, 146.7, 145.9, 140.4, 137.4, 130.0, 129.1, 129.0, 128.8, 128.6, 128.4, 128.3, 127.4, 127.1, 123.5, 123.0, 121.9, 120.9, 114.4, 114.3, 83.6, 55.5, 52.8, 34.3, 30.4, 30.2, 30.2, 29.9, 27.1, 26.2, 25.5, 24.0, 18.9, 18.6, 14.2, 1.5 ppm.

EXAMPLE 15

5-Methyl carboxylate-6-(PDMS(855)-undecoyl)-2,2-bis(4-dimethylaminophenyl)-2H-napthol[1,2-b]pyran Ex 15

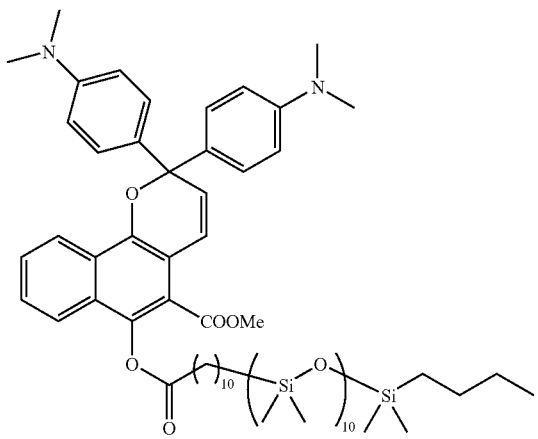

5-Methyl carboxylate-6-(PDMS(855)-undecoyl)-2,2-bis(4 dimethylaminophenyl)-2H-napthol[1,2-b]pyran was synthesised according to the procedure for 5-methyl carboxylate-6-poly(dimethylsiloxane)-undecyl-2,2-bis(4-methoxyphenyl)-2H-napthol[1,2-b]pyran (Example 13) using 5-methyl carboxylate-6-hydroxy-2,2-bis(4-dimethylaminophenyl)-2H-naptho[1,2-b]pyran in place of 5-methyl carboxylate-6-hydroxy-2,2-bis(4-dimethoxyphenyl)-2H-naptho[1,2-b]pyran. $^1$H NMR($C_2D_6O$) δ=0.10 (bs), 0.59 (4H, m), 0.89 (3H, m), 1.34 (24H, m), 1.77 (2H, m), 2.73 (2H, t, J 7.31), 2.89 (12H, s), 3.92 (3H, s), 6.33 (1H, d, J 10.05), 6.68 (4H, d, J 8.95), 6.89 (1H, d, J 10.05), 7.32 (4H, d, J 8.95), 7.50-7.69 (2H, m), 8.37 (1H, d, J 8.41) ppm. $^{13}$C NMR($C_2D_6O$) δ=172.3, 166.5, 150.9, 147.1, 139.9, 133.4, 130.9, 128.5, 128.4, 128.3, 128.2, 127.1, 123.3, 123.1, 121.0, 120.9, 114.3, 112.6, 84.0, 52.8, 40.5, 34.3, 30.4, 30.2, 30.2, 29.9, 27.1, 26.2, 25.5, 24.0, 18.9, 18.6, 14.2, 1.5 ppm.

EXAMPLE 16

5-(Carboxylic acid 2-(PDMS(855)-undecoyl)-oxy-ethyl ester)-9-(dimethylamino)-2,2-(4-dimethylaminophenyl)-2H-napthol[1,2-b]pyran

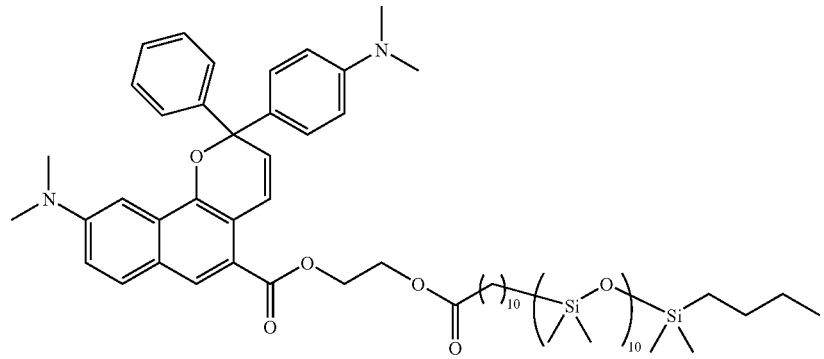

Ex 16

5-(Carboxylic acid 2-(PDMS(855)-undecoyl)-oxy-ethyl ester)-9-(dimethylamino)-2,2-(4-dimethylaminophenyl)-2H-napthol[1,2-b]pyran was synthesised according to the procedure for 5-methyl carboxylate-6-poly(dimethylsiloxane)-undecyl2,2-bis(4-methoxyphenyl)-2H-napthol[1,2-b]pyran (Example 13) using 5-(carboxylic acid 2-hydroxyethylester)-9-(dimethylamino)-2,2-(4-dimethylaminophenyl)-2H-napthol[1,2-b]pyran in place of 5-methyl carboxylate-6-hydroxy-2,2-bis(4-dimethoxyphenyl)-2H-naptho[1,2-b]pyran. $^1$H NMR($C_2D_6O$) δ=0.11 (bs), 0.58 (4H, m), 0.88 (3H, m), 1.30 (24H, m), 1.61 (2H, m), 2.36 (2H m), 2.81 (6H, s), 2.87 (6H, s), 4.48 (2H, m), 4.54 (2H, m), 5.73 (1H, s), 6.20 (1H, dd, J 9.87, 2.92), 6.46-6.69 (2H, m), 7.02-7.48 (8H, m), 7.60 (1H, d, J 10.96), 7.74 (1H, d, J 10.23), 8.15 (1H, s) ppm.

EXAMPLE 17

5-(Carboxylic acid 2-(PDMS(855)-undecoyl)-oxy-ethyl ester)-9-(dimethylamino)-2,2-bis (4-dimethylaminophenyl)-2H-napthol[1,2-b]pyran

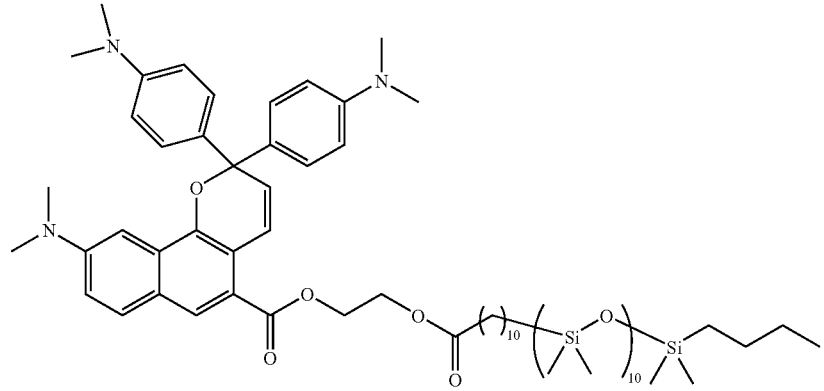

Ex 17

5-(Carboxylic acid 2-(PDMS(855)-undecoyl)-oxy-ethyl ester)-9-(dimethylamino)-2,2-(4-dimethylaminophenyl)-2H-napthol[1,2-b]pyran was synthesised according to the procedure for 5-methyl carboxylate-6-poly(dimethylsiloxane)-undecyl-2,2-bis(4-methoxyphenyl)-2H-napthol[1,2-b]pyran (Example 13) using 5-(carboxylic acid 2-hydroxyethyl ester)-9-(dimethylamino)-2,2-bis(4-dimethylaminophenyl)-2H-napthol[1,2-b]pyran in place of 5-methyl carboxylate-6-hydroxy-2,2-bis(4-dimethoxyphenyl)-2H-naptho[1,2-b]pyran. $^1$H NMR($C_2D_6O$) δ=($C_2D_6O$) 0.12 (bs), 0.58 (4H, m), 0.91 (3H, m), 1.31 (24H, m), 1.62 (2H, m), 2.35 (2H m), 2.88 (12H, s), 3.13 (6H, s), 3.92 (3H, s), 4.40-4.59 (4H, m), 6.28 (1H, d, J 10.05), 6.66 (4H, d, J 8.95), 7.23 (1H, dd, J 9.14, 2.56), 7.36 (5H, d, J 10.05), 7.72 (1H, d, J 9.14), 7.90 (1H, s). $^{13}$C NMR($C_2D_6O$) δ=173.6, 167.4, 151.1, 150.7, 148.1, 134.1, 130.9, 129.9, 129.8, 128.4, 126.1, 125.7, 122.5, 120.2, 117.4, 116.4, 112.6, 100.4, 82.8, 63.2, 62.7, 41.8, 40.5, 34.6, 34.3, 30.4, 30.2, 27.1, 26.2, 25.8, 24.0, 18.9, 18.6, 14.2, 1.4 ppm.

EXAMPLE 18

9'-(PDMS(1077)propyl-ethoxy-succinyl)-1,3,3-trimethylspiro[indoline-2,3'-[3H]naphtha[2,1-b][1,4]oxazine]

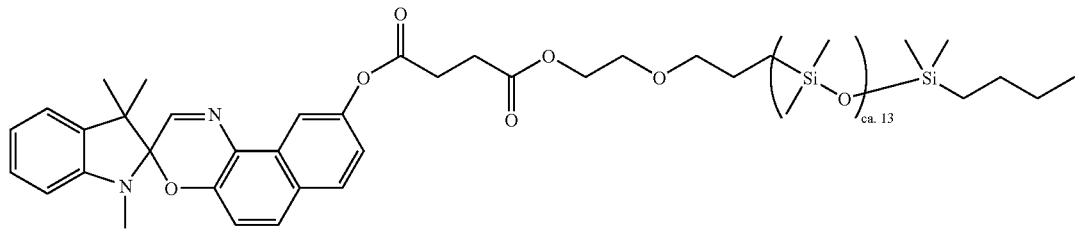

9'-(Monocarboxy-succinyl)-1,3,3-trimethylspiro[indoline-2,3'-[3h]naphtha [2,1-b][1,4]oxazine as prepared in Example 6 (0.6 g 1.35 mmoles) was dissolved in dichloromethane, then monocarbinol terminated polydimethylsiloxane (MCR-C12 from ABCR) (1.76 g, 1.1 equivalents, FW ca 1180) and dimethylaminopyridine (0.135 mmoles 0.1 me, 16 mg) were added. Then dicyclohexylcarbodiimide (0.306 g, 1.1 equiv, 1.485 mmoles) in dichloromethane was added dropwise. The reaction was allowed to stir at room temperature. Tlc analysis indicated a rapid reaction with no starting spirooxazine observed after 1 hour. The reaction was filtered and evaporated then chromatographed on silica with hexane: ether (1:1) to give 1.3 g of clear bluish green oil. $^1$H NMR (acetone-$d_6$) δ=0.09 (s, Si-Me), 0.5 (mult., 2H, alkyl) 1.62 (mult., Indole methyls and oligomer $CH_2$—Si), 1.4-1.8 (mult, alkyl oligomer), 2.77 (s, 3H, 8-H), 2.82 (mutt. succinic $CH_2$), 3.00 (mutt, succinic $CH_2$), 3.44 (t, J=7.2, 2H,), 3.65 (apparent t, J=ca. 5, 2H), 4.25 (apparent t, J=ca. 5, 2H), 6.65 (d, J=7.8, 7-H), 6.87 (t, J=7.3, 5-H), 7.04 (d, J=8.5, 5'-H), 7.14 (d, J=7.3, 4-H), 7.22 (apparent t, 2H, 6 & 8'-H), 7.81 (d, J=9.3, 6'-H), 7.82 (s, 2'H), 7.88 (d, J=8.6, 7'-H), 8.25 (d, J=2.3, 10'-H) ppm.

EXAMPLE 19

5,9'-DI(PDMS(855)-undecoyl)-1,3,3-trimethylspiro[indoline-2,3'-[3H]naphtha[2,1-b][1,4]oxazine]

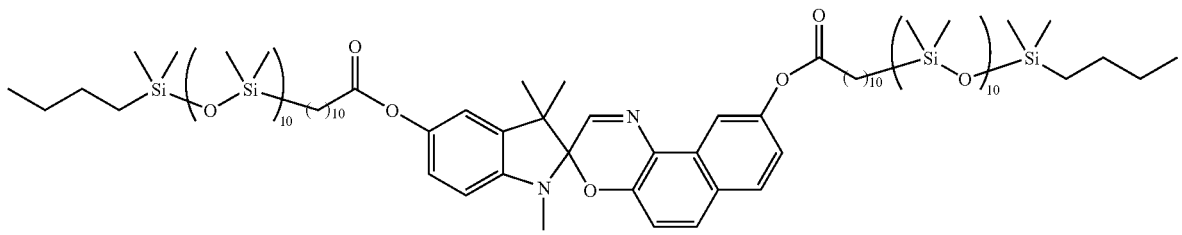

Ex 19

This was made in the same manner as described for Example 3 except poly(dimethylsiloxane) monocarboxydecyl chloride was used in place of succinic acid chloride mono-PEG(350). After addition of poly(dimethylsiloxane) monocarboxydecyl chloride (synthesised in Example 4) to a dichloromethane solution of 5,9-dihydroxy-1,3,3-trimethyl-spiro[indoline-2,3'-[3H]naphtha[2,1-b][1,4]oxazine with triethyl amine the reaction was let stir for about 1 hour. The reaction was worked up by washing with water and brine. The dichloromethane was evaporated to give 2.5 g of crude product. This was purified by column chromatography (silca, ether:hexane 2:1) to give 1.4 g of brown oil. $^1$H NMR (acetone-d$_6$) δ=0.13 (s, Si-methyl), 0.6 (mult., alkyl), 0.90 (mult., alkyl), 1.3-1.4 (mult, gem dimethyl groups+other aliphatic) 2.1-2.4 (mult, alkyl), 2.7 (s, 3H, N—CH3), 6.5-7.5 (mult, aromatic), 7.5-8.2 (mult, aromatic). Photochromic dye signals are very small due to the relatively large amount of PDMS. The methyl groups on the dye provide the clearest signals.

EXAMPLE 20

PDMS(855)-undecoyl 2-(4-phenylazo-phenoxy) ester

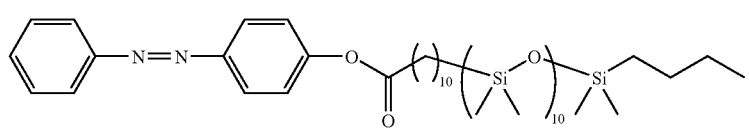

Ex. 20

4-Phenylazophenol (0.127 g, 0.6 mmoles) was dissolved in ether (5-10 mL) and triethylamine (0.1 mL) was added. Then a solution of poly(dimethylsiloxane) monocarboxydecoyl chloride terminated (prepared as Example 4) (0.73 g) dissolved in dichloromethane was added dropwise at room temperature. The reaction was stirred at room temperature for two hours and monitored by tlc (ether). The reaction was worked up by dilution with ether and washing with water and then brine. The organic layer was evaporated and chromatographed on silica with ether to give an orange oil (200 mg).

EXAMPLE 21

9'-(Stearoyl)-1,3,3-trimethylspiro[indoline-2,3'-[3h] naphtha[2,1-b][1,4]oxazine

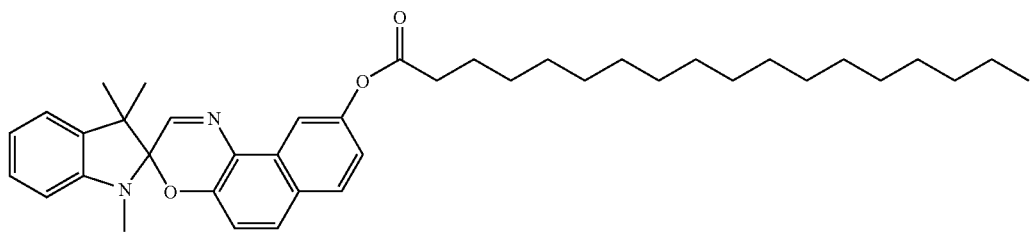

9'-Hydroxy-1,3,3-trimethylspiro[indoline-2,3'-[3H]naph-tha[2,1-b][1,4]oxazine] (0.405 g, 1.2 mmoles) and triethylamine (0.32 mL, 234 mg, 2.32 mmoles) were added together in dichloromethane (20 mL) and stearoyl chloride (456 mg, 1.5 mmol) in dichloromethane was added dropwise to the solution at room temperature under argon protection. The reaction was stirred for one hour and tlc showed reaction had completed. The reaction was worked up by washing with water, drying (MgSO$_4$) and evaporation to give 450 mg of crude product. The sample was recrystallized from 80-100° C. petroleum ether to give 300 mg (42%) of white solid. $^1$H NMR (methylene chloride-d$_2$) δ 0.88 (t, 3H, 'c'-H), 1.28 (s, —CH$_2$—), 1.34 (s, methyl), 1.78 (mult., 2H, 'b'), 2.61 (t, J=7.3, 'a'), 2.74 (s, 3H, N-methyl), 6.57 (d, J=7.7, 7-H), 6.92 (t, J=7.4, 5-H), 7.03 (d, J=8.1, 5'-H), 7.09 (d, 4-H), 7.10 (dd, J=8.8 & 2.1, 8'-H), 7.20 (t of d, J=7.7 & 1.3, 6-H), 7.69 (d, J=8.8, 6'-H), 7.74 (s, 2'-H), 7.77 (d, J=9.0, 7'-H), 8.23 (d, J=2.1, 10'-H) ppm. MS (EI): m/z 610.4 (M$^+$, 60%) 595.4 (15), 329 (20), 185 (10), 159.1 (100), 144.1 (15). MS (HR) m/z 610.4134 (C$_{40}$H$_{54}$N$_2$O$_3$ requires 610.4134).

EXAMPLE 22

9'-(2,2,3,3,4,4,5,5,6,6,7,7,8,8,9,9,10,10,11,11,11-Heneicosafluoro-1-undecyl-succinyl)-1,3,3-trimethylspiro[indoline-2,3'-[3H]napth[2,1-b][1,4]oxazine]

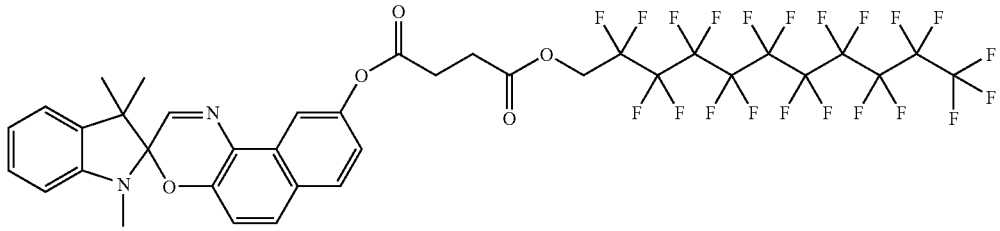

Step 1

5 g (9 mmol) of 2,2,3,3,4,4,5,5,6,6,7,7,8,8,9,9,10,10,11,11,11-heneicosafluoro-1-undecanol, 0.91 g of triethyl amine, 0.90 g succinic anhydride, 50 mg methanol and 25 mg DMAP were added to 60 mL diethyl ether/dichloromethane(6:1). The reaction was stirred overnight at 40° C. Then the product was washed with 0.5 M HCl, water and then brine and dried with MgSO$_4$. 3.9 g of a pink solid-66% yield.

Step 2

4 g of fluorinated succinic acid prepared in step 1 was added to 70 mL diethyl ether/dichloromethane solution (6:1). Then 1.83 g of thionyl chloride was added dropwise. The reaction was left to stir over forty eight hours and then refluxed for four hours. The final product was rotary evaporated to remove the thionyl chloride to give 3.8 g of yellow solid.

Step 3

1.5 g of 9'-Hydroxy-1,3,3-trimethylspiro[indoline-2,3'-[3H]napth[2,1-b][1,4]oxazine] and 0.66 g triethylamine were added to 90 mL diethyl ether/dichloromethane solution (5:1). Then 3.5 g of fluorinated acid chloride in 10 mL diethyl ether was added, dropwise under argon. The reaction was refluxed for three hours. Completion of the reaction was confirmed by tlc (3:1 ether, hexane). The reaction was washed with water, brine and MgSO$_4$ and then rotary evaporated. The final product was purified using column chromatography (3:1 ether, hexane). 1.9 g of yellow powder was obtained. $^1$H NMR (acetone-d$_6$) δ=1.33 & 1.35 (s, 6H, gem dimethyls), 2.77 (s, 3H, N-methyl), 2.85 & 3.05 (mults, 4H, succinic hydrogens), 4.90 (t, J=14.3, 2H, CH$_2$CF$_2$), 6.65 (d, J=7.7, 1H, 7-H), 6.86 (t of d, J=7.4, J=0.7, 1H, 5-H), 7.04 (d, J=9.0, 5'-H), 7.1-7.72 (mult, 3H, 4-H, 8'-H, 6-H), 7.80 (d, J=9.0, 6'-H), 7.82 (s, 1H, 2'-H), 7.88 (d, J=ca 8.7, 1H, 7'-H), 8.25 (d, J=1.8, 10'-H) ppm.

Comparative Example CE1

9'-Propionate-1,3,3-trimethylspiro[indoline-2,3'-[3H]napth[2,1-b][1,4]oxazine]

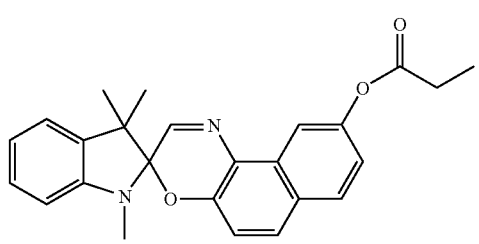

A magnetically stirred solution of 9'-hydroxy-1,3,3-trimethylspiro[indoline-2,3'-[3H]napth[2,1-b][1,4]oxazine] (91.0 g, 2.91 mmol) in dichloromethane (50 mL) was treated with triethylamine (0.84 mL, 0.61 g, 6.03 mmol) followed, dropwise, by a solution of propionyl chloride (0.54 mL, 0.58 g, 6.27 mmol) in dichlormethane (20 mL). The resulting solution was stirred under N$_2$ at room temperature for 30 minutes. Water (100 mL) was added and the solution extracted with dichloromethane (3×50 mL). Removal of the solvent in vacuo followed by flash chromatography (silica gel, 1:5 (ethyl acetate:hexane)) gave the title compound as a green solid (1.11 g, 95%). $^1$H NMR (CDCl$_3$) δ 1.32 (3H, t, J=7.31), 1.35 (6H, s), 2.57 (2H, q, J=7.31), 2.76 (3H, s), 6.58 (d, J=7.7, 1H, 7-H), 6.91 (t, J=7.3, 1H, 5-H), 6.99 (d, J=8.8, 5'-H), 7.09 (d, J=7.3, 1H, 4-H), 7.13 (d of d, J=8.0 & 2.2, 1H, 8'-H), 7.21 (t of d, J=7.7 & 1.5, 1H, 6-H), 7.66 (d, J=8.7, 6'-H), 7.75 (s, 1H, 2'-H), 7.73 (d, J=8.7, 1H, 7'-H), 8.23 (d, J=2.6, 10'-H) ppm.

Comparative Example CE2

5-Propionate-1,3,3-trimethylspiro[indoline-2,3'-[3H]napth[2,1-b][1,4]oxazine]

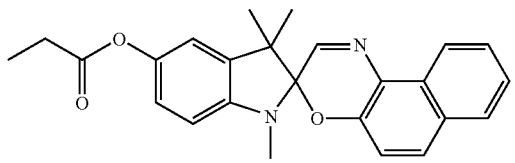

CE 2

5-Propionate-1,3,3-trimethylspiro[indoline-2,3'-[3H]napth[2,1-b][1,4]oxazine] was synthesised according to the procedure for the preparation of 9'-propionate-1,3,3-trimethylspiro[indoline-2,3'-[3H]napth[2,1-b][1,4]oxazine] (CE1) using 5-hydroxy-1,3,3,-trimethylspiro[indoline-2,3'-[3H]napth[2,1-b][1,4]oxazine] in place of 9'-hydroxy-1,3,3,-trimethylspiro[indoline-2,3'-[3H]napth[2,1-b][1,4]oxazine] (51%). $^1$H NMR($C_2D_6O$) δ=1.19 (3H, t, J 7.31), 1.33 (3H, s), 1.38 (3H, s), 2.57 (2H, q, J 7.31), 2.76 (3H, s), 6.64 (1H, d, J 8.77), 6.91 (1H, dd, J 7.31, 2.19), 6.93 (1H, s), 7.08 (1H, d, J 8.77), 7.42 (1H, dd, J 8.41, 1.46), 7.59 (1H, dd, J 8.41, 1.46), 7.75-7.88 (3H, m), 8.57 (1H, d J 8.41) ppm. $^{13}$C NMR ($C_2D_6O$) δ=173.6, 151.6, 146.1, 145.6, 144.9, 137.8, 131.8, 131.2, 130.4, 128.7, 127.9, 125.0, 123.9, 122.3, 121.5, 117.5, 116.6, 108.0, 99.8, 52.5, 30.0, 27.9, 25.6, 20.8, 9.4 ppm.

Comparative Example CE3

6'-Cyano-5-propionate-1,3,3-trimethylspiro[indoline-2,3'-[3H]napth[2,1-b][1,4]oxazine]

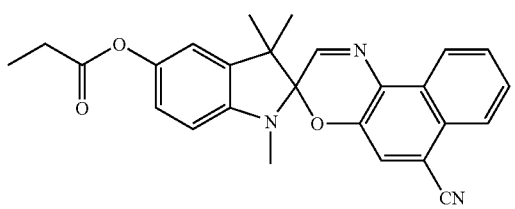

CE 3

6'-cyano-5-propionate-1,3,3-trimethylspiro[indoline-2,3'-[3H]napth[2,1-b][1,4]oxazine] was synthesised according to the procedure for the preparation of 9'-propionate-1,3,3,-trimethylspiro[indoline-2,3'-[3H]napth[2,1-b][1,4]oxazine] (CE1) using 6'-cyano-5-hydroxy-1,3,3,-trimethylspiro[indoline-2,3'-[3H]napth[2,1-b][1,4]oxazine] in place of 9'-hydroxy-1,3,3,-trimethylspiro[indoline-2,3'-[3H]napth[2,1-b][1,4]oxazine] (51%). $^1$H NMR($C_2D_6O$) δ=1.19 (3H, t, J 7.31), 1.34 (3H, s), 1.39 (3H, s), 2.58 (2H, q, J 7.31), 2.78 (3H, s), 6.66 (1H, d, J 8.95), 6.91 (1H, dd, J 7.31, 2.19), 6.95 (1H, s), 7.60-7.82 (3H, m), 8.05 (1H, s), 8.09 (1H, d, J 7.68), 8.70 (1H, d J 7.68) ppm. $^{13}$C NMR($C_2D_6O$) δ=173.6, 155.5, 145.9, 144.0, 137.5, 131.5, 129.4, 129.3, 127.7, 127.6, 127.6, 125.5, 124.4, 123.4, 121.7, 117.4, 116.6, 111.7, 108.2, 100.3, 53.0, 30.0, 27.9, 25.6, 20.8, 9.4 ppm.

Comparative Example CE4

5-Methoxy-9'-propionate-1,3,3,-trimethylspiro[indoline-2,3'-[3H]napth[2,1-b][1,4]oxazine]

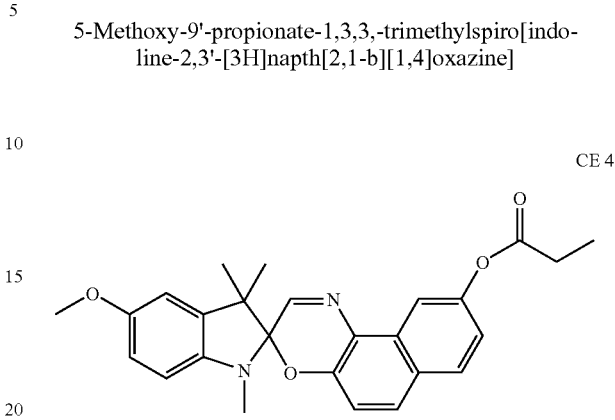

CE 4

5-Methoxy-9'-propionate-1,3,3-trimethylspiro[indoline-2,3'-3H]napth[2,1-b][1,4]oxazine] was synthesised according to the procedure for the preparation of 9'-propionate-1,3,3-trimethylspiro[indoline-2,3'43H]napth[2,1-b][1,4]oxazine] (CE1) using 5-methoxy-9'-hydroxy-1,3,3,-trimethylspiro[indoline-2,3'-[3H]napth[2,1-b][1,4]oxazine] in place of 9'-hydroxy-1,3,3-trimethylspiro [indoline-2,3'-[3H]napth[2,1-b][1,4]oxazine] (62%). $^1$H NMR($C_2D_6O$) δ=1.24 (3H, t, J 7.68), 1.30 (6H, bs), 2.69 (2H, q, J 7.68), 3.80 (3H, s), 6.72-6.93 (3H, m), 7.05 (1H, d, J 9.14), 7.19 (1H, dd, J 8.77, 2.19), 7.78 (1H, s), 7.79 (1H, d, J 7.68), 8.24 (1H, d, J 2.56) ppm. $^{13}$C NMR($C_2D_6O$) δ=173.4, 152.2, 151.0, 146.6, 145.7, 138.4, 136.0, 132.7, 131.0, 130.2, 128.1, 123.5, 121.9, 120.5, 117.2, 115.3, 113.7, 113.2, 100.4, 56.4, 52.6, 32.7, 28.1, 25.8, 20.9, 9.4 ppm.

Comparative Example CE5

2-(9'-Oropionic acid oxy-ethyl ester)-1,3,3,-trimethylspiro[indoline-2,3'-[3H]napth[2,1-b][1,4]oxazine]

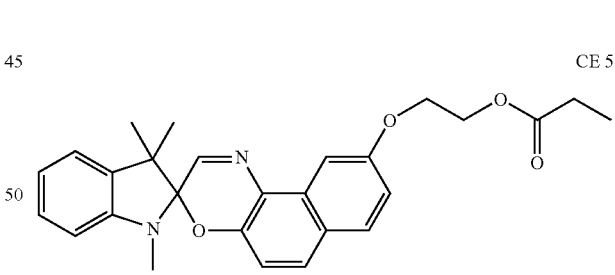

CE 5

2-(9'-Propionic acid oxy-ethyl ester)-1,3,3-trimethylspiro[indoline-2,3'-[3H]napth[2,1-b][1,4]oxazine] was synthesised according to the procedure for the preparation of 9'-propionate-1,3,3-trimethylspiro[indoline-2,3'-[3H]napth[2,1-b][1,4]oxazine] (CE1) using 2-(9'-oxyethanol)-1,3,3,-trimethylspiro[indoline-2,3'-[3H]napth[2,1-b][1,4]oxazine] in place of 9'-hydroxy-1,3,3-trimethylspiro [indoline-2,3'-[3H]napth[2,1-b][1,4]oxazine]. $^1$H NMR($C_2D_6O$) δ=1.11 (3H, t, J 7.68), 1.33 (3H, s), 1.35 (3H, s), 2.38 (2H, q, J 7.50), 2.77 (3H, s), 4.42 (2H, t, J 4.08), 4.51 (2H, t, J 4.08), 6.65 (1H, d, J 7.68), 6.83-6.93 (2H, m), 7.08 (1H, d, J 8.97), 7.11-7.23 (2H, m), 7.70 (1H, d, J 8.78), 7.76 (1H, d, J 8.78), 7.80 (1H, s), 7.95 (1H, d, J1.83) ppm.

Comparative Example CE6

5-Methyl carboxylate-6-propionic acid ester-2,2-bis(4-methoxyphenyl)-2H-naptho[1,2-b]pyran

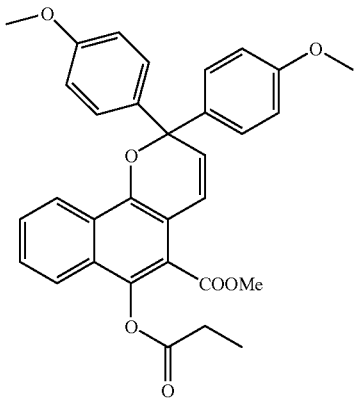

CE 6

A mechanically stirred solution of 5-methyl carboxylate-6-hydroxy-2,2-bis(4-dimethoxyphenyl)-2H-naptho[1,2-b]pyran (0.50 g, 1.07 mmol) and triethylamine (0.24 g, 2.35 mmol) in dichloromethane (10 mL) was treated dropwise with a solution of propionyl chloride (0.19 g, 2.02 mmol) in dichloromethane (10 mL).

The resulting solution was stirred at room temperature under $N_2$ for 30 minutes. Water (50 mL) was added and the solution was extracted with dichloromethane (3×50 mL). Removal of the solvent in vacuo followed by column chromatography (silica, eluent hexane/ethyl acetate 3/1) gave the title compound as an red solid (0.51 g, 91%). $^1$H NMR ($C_2D_6O$) δ=1.26 (3H, t, J 7.68), 2.76 (2H, q, J 7.68), 3.72 (6H, s) 3.94 (3H, s), 6.39 (1H, d, J 10.05), 6.88 (2H, d, J 8.77), 6.99 (1H, d, J 10.05, 7.45 (1H, d, J 8.77), 7.51-7.71 (2H, m), 7.88 (1H, d, J 8.41), 8.42 (1H, d, J 7.86) ppm. $^{13}$C NMR($C_2D_6O$) δ=173.1, 166.4, 160.1, 146.7, 140.4, 137.7, 130.3, 128.9, 128.8, 128.6, 128.3, 127.1, 123.5, 123.0, 121.6, 120.8, 114.4, 83.5, 55.5, 52.9, 27.8, 9.4 ppm.

Comparative Example CE7

5-Methyl carboxylate-6-propionic acid ester-2,2-(4-methoxyphenyl)-2H-naptho[1,2-b]pyran

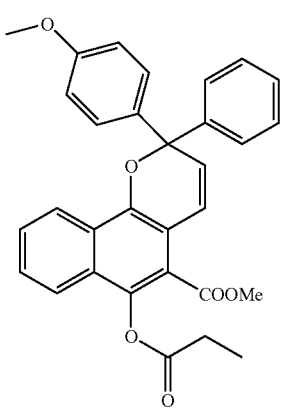

CE 7

5-methyl carboxylate-6-propionic acid ester-2,2-(4-dimethoxyphenyl)-2H-naptho[1,2-b]pyran was synthesised according to the procedure for 5-methyl carboxylate-6-propionic acid ester-2,2-bis(4-dimethoxyphenyl)-2,4-naptho[1,2-b]pyran (CE6) using 5-methyl carboxylate-6-hydroxy-2,2-(4-dimethoxyphenyl)-2H-naptho[1,2-b]pyran in place of 5-methyl carboxylate-6-hydroxy-2,2-bis(4-dimethoxyphenyl)-2H-naptho[1,2-b]pyran. This provided an orange solid (79%). $^1$H NMR($C_2D_6O$) δ=1.29 (3H, t, J 7.49), 2.78 (2H, q, J 7.49), 3.68 (3H, s), 3.95 (3H, s), 6.46 (1H, d, J 10.05), 6.88 (2H, d, J 8.77), 7.07 (1H, d, J 10.05), 7.20-7.44 (3H, m), 7.51 (2H, d, J 8.77), 7.55-7.71 (4H, m), 7.91 (1H, d, J 8.56), 8.50 (1H, d, J 8.77) ppm. $^{13}$C NMR($C_2D_6O$) δ=173.2, 166.4, 160.2, 146.8, 146.0, 140.6, 137.4, 130.1, 129.2, 129.1, 129.0, 128.7, 128.5, 128.4, 127.5, 127.2, 123.6, 123.1, 122.0, 120.8, 114.5, 114.4, 83.7, 55.6, 53.0, 27.9, 9.6 ppm.

Comparative Example CE8

5-(Carboxylic acid 2-methyl ester)-9-(piperidino)-2,2-(4-dimethylaminophenyl)-2H-napthol[1,2-b]pyran

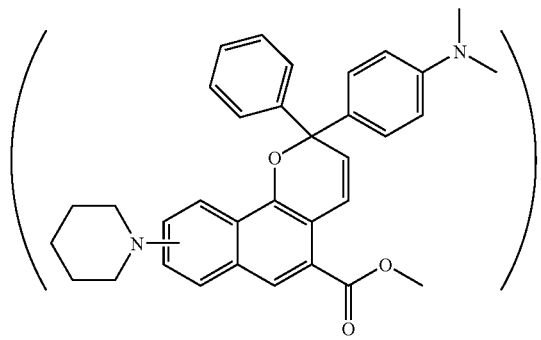

CE 8

James Robinson
Midnight grey

James Robinson Midnight Grey was used as supplied. NMR and mass spectral analysis suggested a structure given above. The structure above is the best fit with the spectral data and the information in U.S. Pat. No. 6,387,512.

Comparative Example CE9

5-Methyl carboxylate-6-propionic acid ester-2,2-bis(4-dimethylaminophenyl)-2H-naptho[1,2-b]pyran

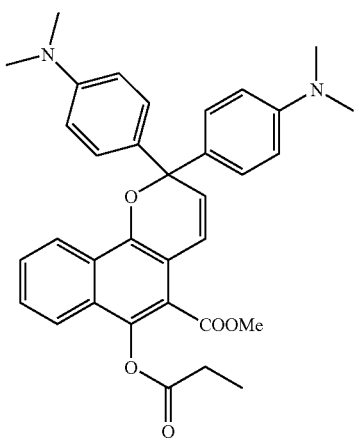

CE 9

5-Methyl carboxylate-6-propionic acid ester-2,2-bis(4-dimethylaminophenyl)-2H-naptho[1,2-b]pyran was synthesised according to the procedure for 5-methyl carboxylate-6-propionic acid ester-2,2-bis(4-dimethoxyphenyl)-2H-naptho[1,2-b]pyran (CE6) using 5-methyl carboxylate-6-hydroxy-2,2-bis(4-dimethylaminophenyl)-2H-naptho[1,2-b]pyran in place of 5-methyl carboxylate-6-hydroxy-2,2-bis(4-dimethoxyphenyl)-2H-naptho[1,2-b]pyran. This provided a pale blue solid (85%). $^1$H NMR($C_2D_6O$) δ=1.25 (3H, t, J 7.49), 2.75 (2H, q, J 7.49), 2.88 (12H, s), 3.92 (3H, s), 6.33 (1H, d, J 10.05), 6.67 (4H, d, J 6.67), 6.90 (1H, d, J 9.89), 7.33 (4H, d, J 8.95), 7.50-7.68 (2H, m), 7.83 (1H, d, J 7.68), 8.38 (1H, d, J 7.68) ppm. $^{13}$C NMR($C_2D_6O$) δ=173.1, 166.5, 150.9, 150.9, 147.1, 139.9, 136.0, 133.4, 131.0, 128.5, 128.4, 128.2, 127.1, 123.4, 123.1, 120.9, 114.3, 112.6, 84.0, 52.8, 40.5, 27.7, 9.4 ppm.

Comparative Example CE10

Propionic acid 4-phenylazo-phenyl ester

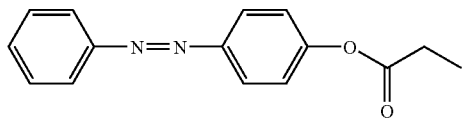

4-Phenylazophenol (0.25 g, 1.26 mmoles) was dissolved in ether (5-10 mL) and triethylamine (0.26 mL) was added. Then propanoyl chloride (0.14 g 1.5 mmoles) in ether (1 mL) was added dropwise at room temperature. The mixture was stirred and reaction was rapidly completed. The reaction mixture was washed with water, dilute acid and brine and dried with magnesium sulfate. The solvent was evaporated to give 0.23 g (72%) of product. $^1$H NMR (CDCl$_3$) δ=1.16 (3H, t, J=7.7), 2.40 (2H, q J=7.7), 7.25 (2H, m), 7.40-7.58 (3H, m), 7.88-8.0 (4H, m) ppm.

EXAMPLE 23

NMR Experimental Observation of Nanoencapsulation

The two dyes described in Example 1 and Example 5 were examined by $^1$H NMR spectroscopy to determine whether the attached oligomer was interacting with the photochromic dye in a manner that was consistent with nanosolvation/nanoencapsuation. This was carried out by dissolving the dye in deutero acetone and irradiating the dye with UV light. ROE (Rotational Overhausen Enhancement) experiment were performed while the dye was in the coloured state. ROE is a technique similar to NOE (Nuclear Overhausen Enhancement) but is modified for use in large molecules. The technique allows the through space proximity of hydrogens to be determined. Selected hydrogens are irradiated (with radio frequency) and other hydrogens are observed to see if they are enhanced. If another hydrogen is close enough, then energy is transferred to it from the irradiated hydrogen.

It was found that PEG oligomer of Example 1 does coil near or around the dye. This is shown in the ROE experiment (see top spectrum of FIG. 5) where energy irradiated into the first CH$_2$ group of the first PEG unit was transferred to the marked hydrogens on the other side of the molecule. This transfer is evidenced by an enhancement of the signals due to those hydrogens. For this to happen those hydrogens must be in close proximity to the hydrogen being irradiated. Thus the PEG is coiling near or around the dye rather than being lost into the solvent. In the clear form there is a weaker association. Thus when in a lens environment it can be expected that the PEG chains will similarly coil near/around the dye molecule and so provide a favourable switching environment. The bottom two spectra of FIG. 5 are conventional spectra of the molecule in solution obtained by subtraction and normally.

Figure 7:
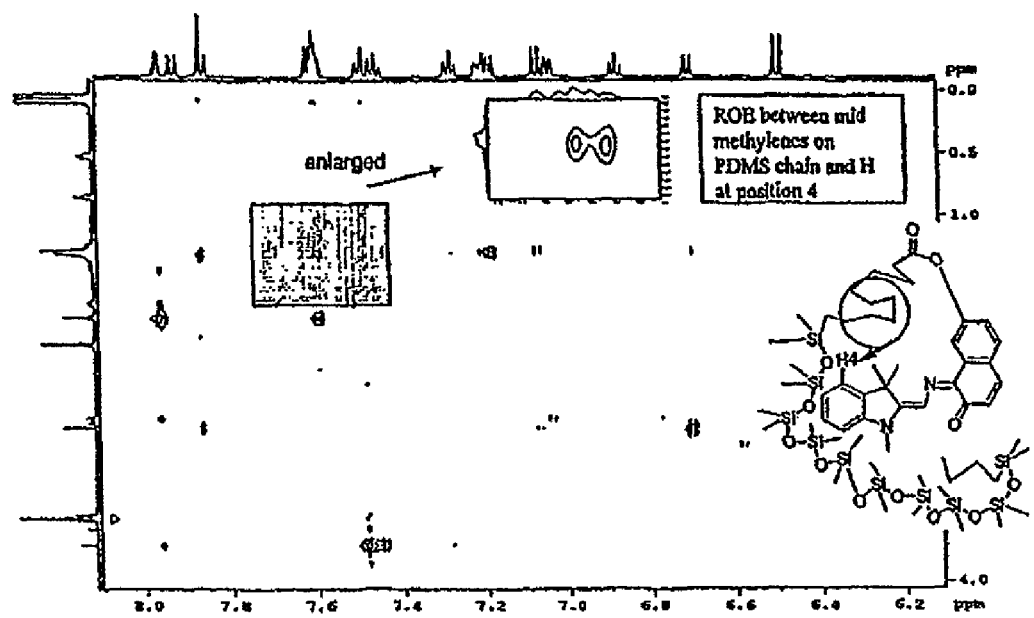
FIG. 7 is an ROE nmr experiment providing evidence of nano solvation/encapsulation in the compound of Example 5.

Similarly for the dyes of Example 5 with the PDMS oligomer it was shown that the oiligomer coils around the molecule. (FIGS. 6 and 7) In the ROE experiment, energy transfer was observed between the mid methylenes and endgroup of the PDMS chain with the central H of the coloured form of the spirooxazine (FIG. 6). Energy transfer was also observed between the mid methylenes of the undecyl portion of the oligomer and the 4 hydrogen on the indole (FIG. 7). Thus the PDMS chain must be highly localised around the spirooxazine. There is a similar but weaker association in the clear form.

These experiment show that the oligomers are not only localised around the dye molecule but wrap around the dye to varying degrees with interactions between the oligomer and the far side of the dye observed, and in the case of the PDMS oligomer there are multiple sites of interaction. This nanoencapsulation would be expected to be greater in the rigid environment of a polymer matrix where the mobility of the surrounding host medium (in this case the host polymer) is much less.

EXAMPLE 24

Photochromic Behaviour of Dyes Cast in a Cure Polymer Matrix

Table 6 gives the fade speed results for the example dyes that were cast in to test lenses directly.

The following is a standard formulation and testing procedure which we used to assess the performance of many photochromic compounds of the invention. The test is referred to in the specification and claims as "the standard photochromic cast test".

The monomer mix consisted of 16 g of 2,2'-bis[4-methacryloxyethoxy)phenyl]propane known as Nouryset 110, 4 g of polyethylenglycol 400 dimethacrylate known as NK ester 9G and 80 mg (0.4%) of AIBN. This is referred to though out as the "monomer mix A". The dye was mixed into the monomer then placed into small moulds. The moulds consisted of a small silicon or viton o-ring (14.5 mm internal diameter, width 2.6 mm). This was stuck to a microscope slide using cyanoacrylate glue. The monomer mix was poured into the mould and another microscope slide was placed on top and air bubbles were excluded. The two plates were clipped together and the sample heated at 75° C. for 16 hours. The lens was recovered and was typically 14.2 mm in diameter and 2.6 mm thick and weighed about 0.5 g.

All measurements were performed on a custom built optical bench similar to that described for the thin film observations in Example 8. The bench consisted of Cary 50 Bio UV-visible spectrophotometer fitted with a Cary peltier accessory for temperature control, a 280 W Thermo-Oriel xenon arc lamp, an electronic shutter, a water filter acting as a heat sink for the arc lamp, a Schott WG-320 cut-off filter and a Hoya U340 band-pass filter. The solution samples were placed in quartz cuvettes and solid samples were placed at 45 degree angle to both UV lamp and light path of spectrophotometer. The resulting power of UV light at the sample was measured using an Ophir Optronics Model AN/2 power meter giving 25 mW/cm$^2$.

The change in absorbance was measured by placing the appropriate sample in the bleached state and adjusting spectrophotometer to zero absorbance. The samples were then irradiated with UV light from the xenon lamp by opening the shutter and measuring the change in absorption. The absorption spectra were recorded for both the bleached and activated (coloured) state. The wavelength of the maxima in absorbance was then recorded and used for the monitoring of kinetics of activation and fade. Test lens samples were activated with 1000 seconds UV exposure.

TABLE 6

Photochromic behaviour of dyes cast into a cured polymer matrix of monomer mix A consisting of 4:1 2,2'-bis[4-(methacryloxyethoxy)phenyl]propane and poly(ethylglycol) (400) dimethacrylate.

| Example Number | Dye (mg) | Monomer (g) | $A_o$ | $T_{1/2}$ (seconds) | $T_{3/4}$ (seconds) |
|---|---|---|---|---|---|
| 2 | 7.0 | 2.0152 | 1.61 | 9 | 50 |
| CE 1 | 1.1 | 1.017 | 1.64 | 14 | 191 |
| 5 | 3.7 | 1.008 | 1.63 | 3 | 7 |
| CE 1 | 1.1 | 1.017 | 1.64 | 14 | 191 |
| 6 | 4.0 | 1.0293 | 2.1 | 13 | 92 |
| CE 1 | 1.1 | 1.017 | 1.64 | 14 | 191 |
| 9 | 3.9 | 1.009 | 1.13 | 3 | 12 |
| CE 2 | 1.0 | 1.021 | 1.07 | 34 | 633 |
| 10 | 0.16 | 2.064 | 0.58 | 50 | 144 |
| CE 3 | 0.176 | 1.871 | 1.85 | 128 | 721 |
| 11 | 5.3 | 1.56 | 2.35 | 13 | 29 |
| CE 4 | 2.1 | 1.996 | 2.16 | 21 | 167 |
| 12 | 1.3 | 2.1610 | 1.19 | 8 | 36 |
| CE 5 | 1.02 | 1.009 | 1.73 | 20 | 219 |
| 13 | 0.49 | 1.534 | 0.84 | 34 | 790 |
| CE 6 | 0.52 | 1.517 | 1.93 | 78 | 3943 |
| 14 | 0.47 | 1.637 | 0.75 | 95 | n/a |
| CE 7 | 0.4 | 1.6914 | 2.15 | 212 | 7287 |
| 15 | 0.3 | 2.553 | 0.83 | 5 | 26 |
| CE 9 | 0.74 | 2.012 | 1.10 | 247 | 2995 |
| 16 | 1.2 | 1.228 | 1.34 | 18 | 758 |
| CE 8 | 0.59 | 1.853 | 1.11 | 185 | 1691 |
| 17 | 3.07 | 1.604 | 1.03 | 7.5 | 94 |
| 18 | 2.65 | 1.2964 | 1.98 | 8 | 36 |
| CE 1 | 1.1 | 1.017 | 1.64 | 14 | 191 |
| 19 | 2.4 | 1.0072 | 0.85 | 15 | 84 |
| 20 | 1.92 | 1.030 | 0.26 | 2000 | n/a |
| CE 10 | 1.39 | 1.3392 | 0.5 | >70000 | n/a |
| 21 | 1.22 | 1.257 | 1.67 | 32 | 441 |
| CE 1 | 1.1 | 1.017 | 1.64 | 14 | 191 |
| 22 | 3.9 | 1.2912 | 1.80 | 9 | 43 |
| CE 1 | 1.1 | 1.017 | 1.64 | 14 | 191 |

It can be seen in all examples that the presence of a polydimethylsiloxane oligomer, polyethylgylcol oligomer or perfluorinated alkane oligomer gave significantly faster fade speed as measured by $T_{1/2}$ or $T_{3/4}$. $T_{1/2}$ is the time taken for the optical density to reduce by half from the initial maximum optical density of the coloured from when UV irradiation is stopped. $T_{3/4}$ is time taken for the optical density to reduce by three quarters from the initial maximum optical density of the coloured form of the dye. In all those cases except for Example 6 (and Example 21), the reduction in $T_{1/2}$ ranges from 40% to 95% and $T_{3/4}$ by 60% to 99% as compared to the electronically identical comparison examples that do not have the oligomer. The following points are illustrated by these examples:

1. It is extremely surprising and unexpected to find that the addition of a relatively large substituent such as a PDMS oligomer (ca 1000 g mwt) would cause the dyes to switch faster than the correspondingly electronically identical dye with only a propylate substituent (29 g mwt) in a rigid polymer matrix. [Note that this matrix is not tuned to encourage photochromic performance. This tuning is typically done by addition of other monomers that 'soften' the entire matrix and so compromise physical properties of the lens to some extent.] Example 5 is typical. Note the rapid colouration and overshoot of example 5 as compared to CE1. (FIGS. 8 and 9). The dyes are electronically identical yet the dye with the oligomer (Example 5) not only fades faster but does so by a large margin with the $T_{1/2}$ and $T_{3/4}$ reduced by 79% and 96% respectively as compared to the comparison dye (CE1) in the identical matrix.

2. The position of attachment of the oligomer makes no substantial difference to the dyes performance. They are all much faster than their corresponding comparison dyes. (See kinetic data for Examples 5, 9, 13, and 16 and corresponding comparative examples).

3. The nature of the linking group between the oligomer and dye has no apparent effect on the fade speed. They are all much faster than their comparison dyes See kinetic data for example 5, 12 and 18 and corresponding comparative examples.

4. The nature of the linear of PDMS oligomer has little effect on the fade performance with examples 5 and 18 with them significantly out performing CE1 although the PDMS oligomers and linking groups are different.

5. Example 6 with the POSS substituent is different among the PDMS dyes. The POSS group is relatively rigid (i.e. high Tg) as compared to linear PDMS oligomers. Example 6 was a solid where as the dyes with linear PDMS oligomers are oils or low melting point solids. Its $T_{1/2}$ is much the same as the comparison dye but its $T_{3/4}$ is significantly faster. This is likely to be due to the free volume that the large POSS group would create around it. It is thought that it is because of this free volume that the solid state crystalline photochromism observed in Example 6 occurs.

Figure 10:
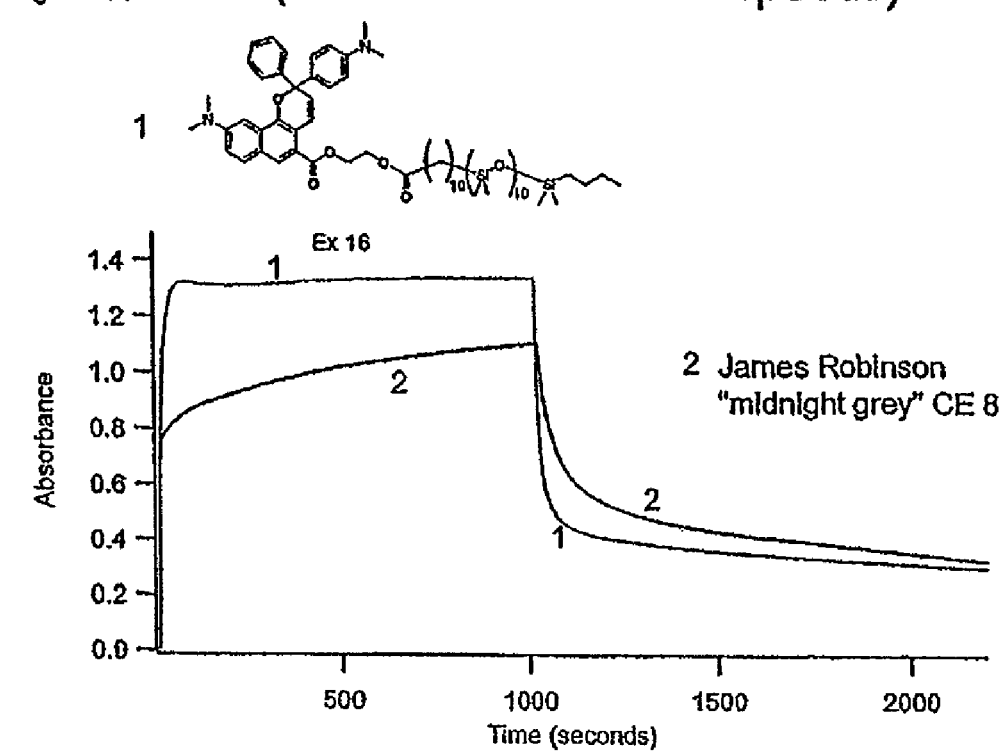
FIG. 10 is an absorbance graph showing the colouration and fade speed of the compound of Example 16.
Figure 11:
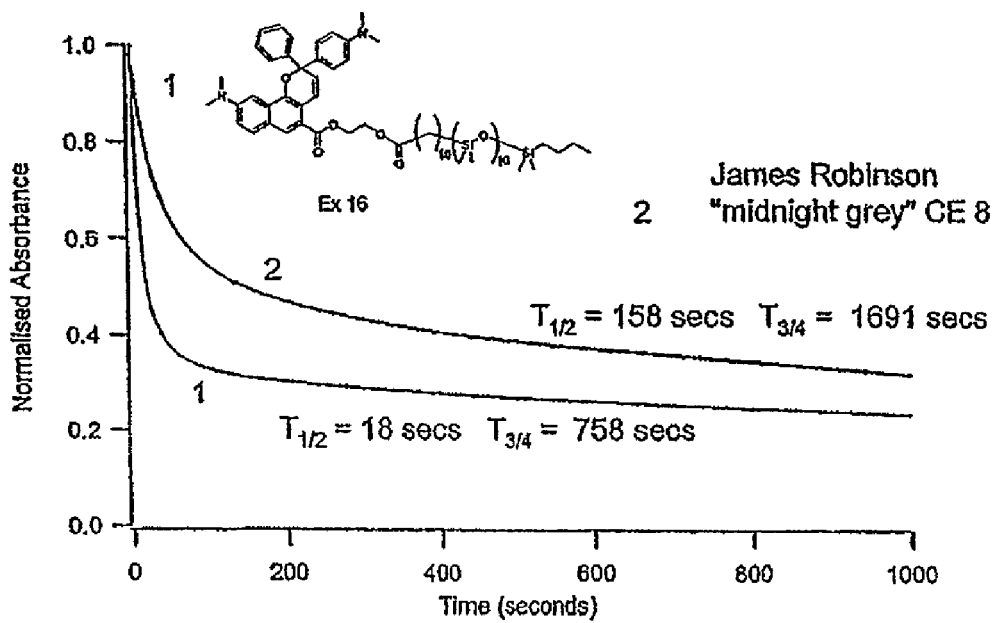
FIG. 11 is a normalised absorbance graph of the set up referred to in FIG. 10.
Figure 12:
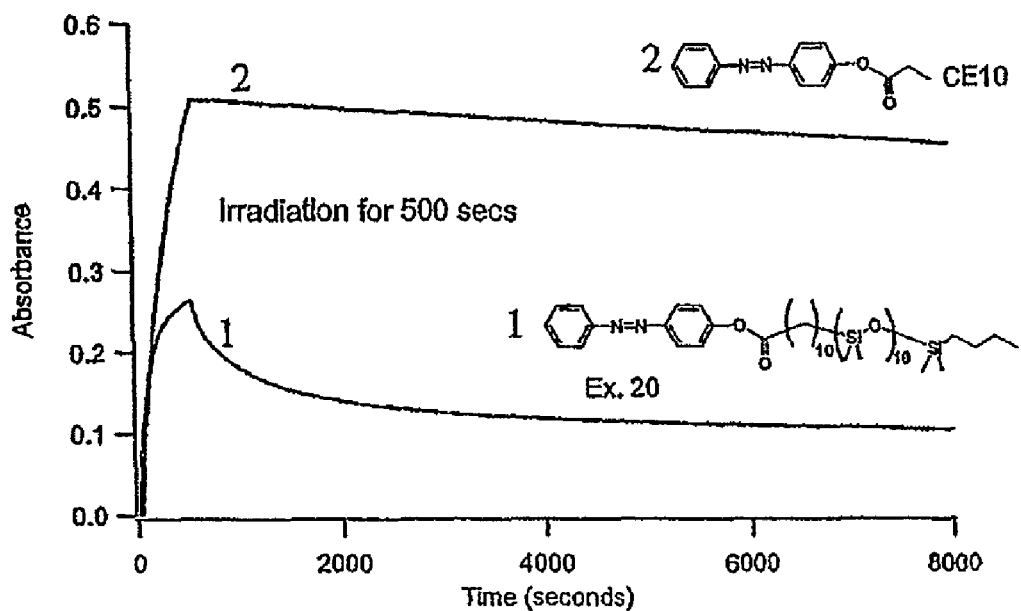
FIG. 12 is an absorbance graph showing the colouration and fade speed of the compound of Example 20.
Figure 13:
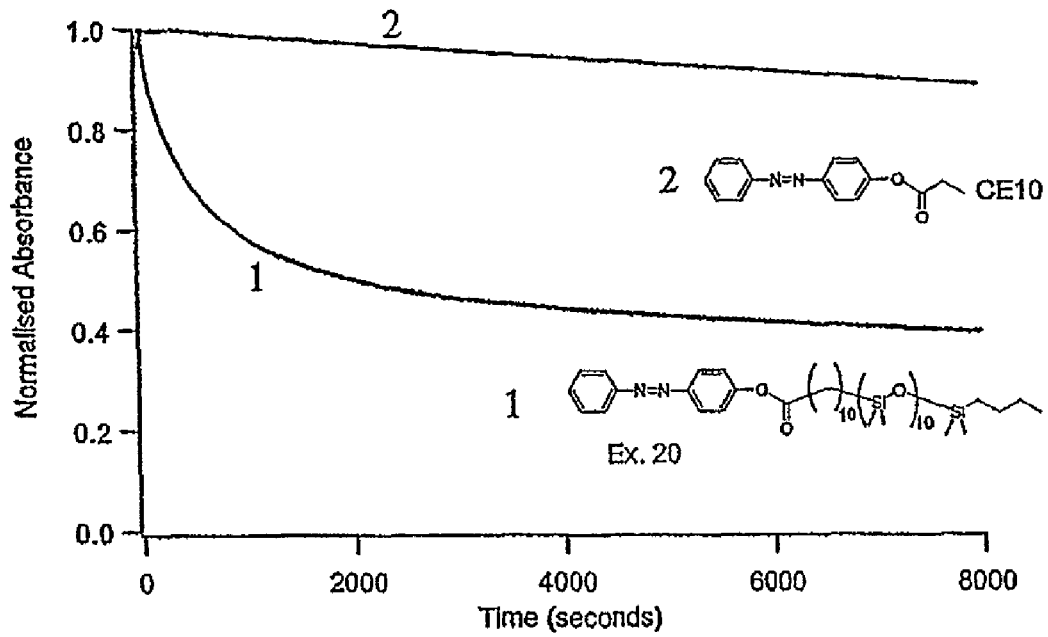
FIG. 13 is a normalised absorbance graph of the set up described for FIG. 12.

6. The concept of low Tg oligomers improving switching speed and fade speed in particular is applicable for any photochromic dye that involves a structural molecular rearrangement with spiro-oxazines (Examples 2, 5, 6, 9, 10, 11, 12, 18, 23), chromenes (13, 14, 15, 16, 17) (FIGS. 10 and 11) and the azo (Example 20)(FIGS. 12 and 13) dyes all shown to have a fade speed enhancement in their thermal reverse reactions to the coloured state. Thus this is a generic "bolt-on" solution for fade speed enhancement than does not alter the colour of the dye.

7. The addition of a high Tg oligomer such as stearyl (Example 21) gave slower fade speeds. This further illustrates the need for low Tg oligomers for fast fade speed and high Tg oligomer for slow fade speed.

8. The Tg of the oligomer is maybe more important than its compatibility but compatibility still contributes to fade speed. Example 2 which possess a long PEG chain of ca 16 units would be expected to have some compatibility with the monomer mix A which contains polyethyleneglycol) dimethacrylate. However fast fade is still observed although not as fast as the PDMS example 5 (FIGS. 8 and 9).

9. The kinetic results of examples as a whole, illustrate the control over photochromic performance that can be obtained without altering the electronic nature of the dye. This is very important as it means no change in the colour occurs yet its fade speed can be greatly changed. Note the three fade speed obtained for the electronically identical dyes Example 5, CE1 and Example 21. $T_{1/2}$ ranges from 3 second to 32 seconds (one order of magnitude) and $T_{3/4}$ ranges from 7 second to 441 seconds (one and half orders of magnitude).

10. The electronic nature of the dye not only affects the observed colour of the open form but can affect the switching speed. The oligomer can not change that part of the switching speed of the dye that is due to the electronic nature of the dye. For example, Example 10 is an inherently slow switching dye even in solution. The low Tg oligomer (ie PDMS) simply provides a near-solution like environment to allow the due to switch as fast as it can. Example 9 switches much faster than Example 10. That is due to the different electronic nature of the two dyes. But Example 10 still switches much faster than the electronically identical comparison dye CE3 and that is the effect of the low Tg nanoenvironment of the PDMS oligomer.

Importance of the Attachment of the Oligomer.

Figure 14:
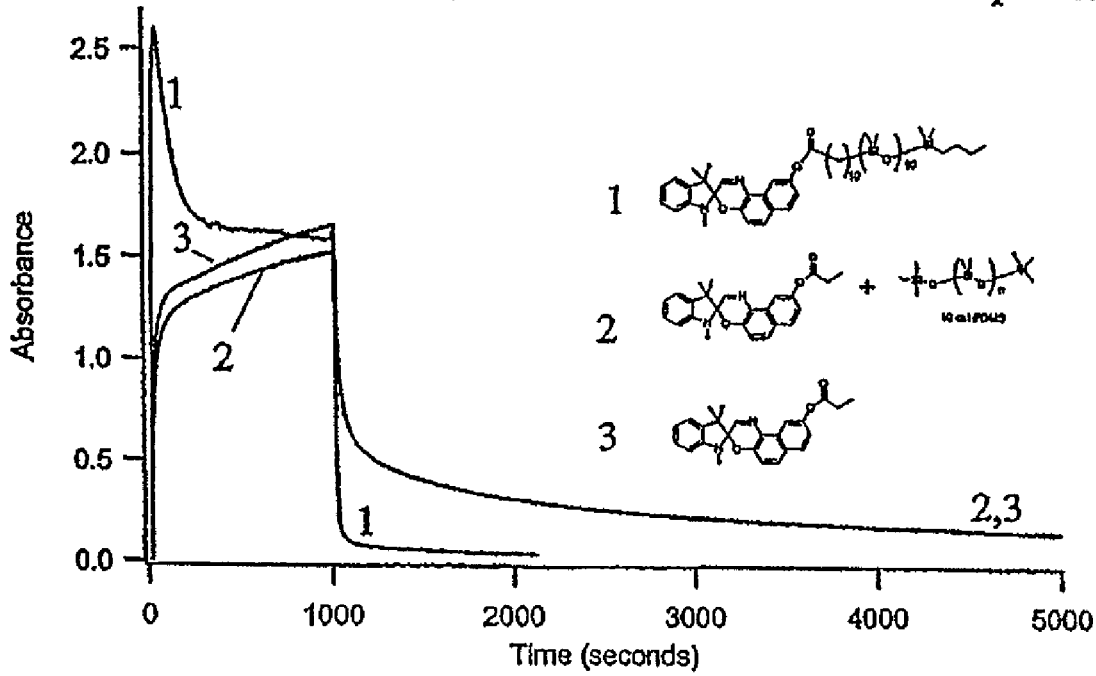
FIG. 14 is an absorbance graph showing the colouration and fade speed of the dyes of Example 5 and CE3.
Figure 15:
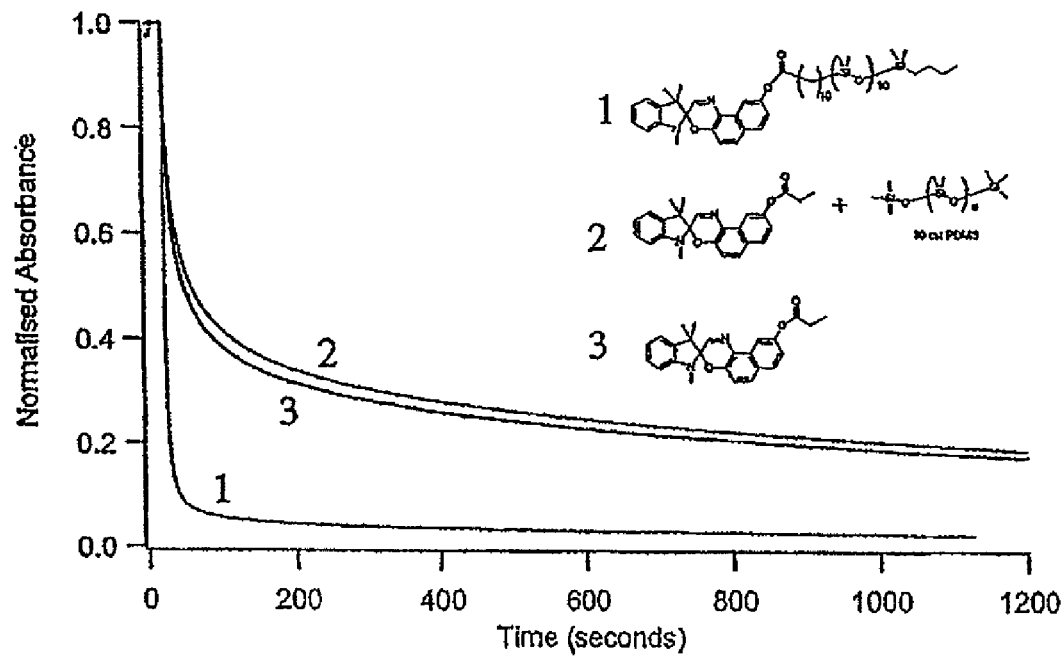
FIG. 15 is a normalised absorbance graph of the set up described for Example 14.
Figure 16:
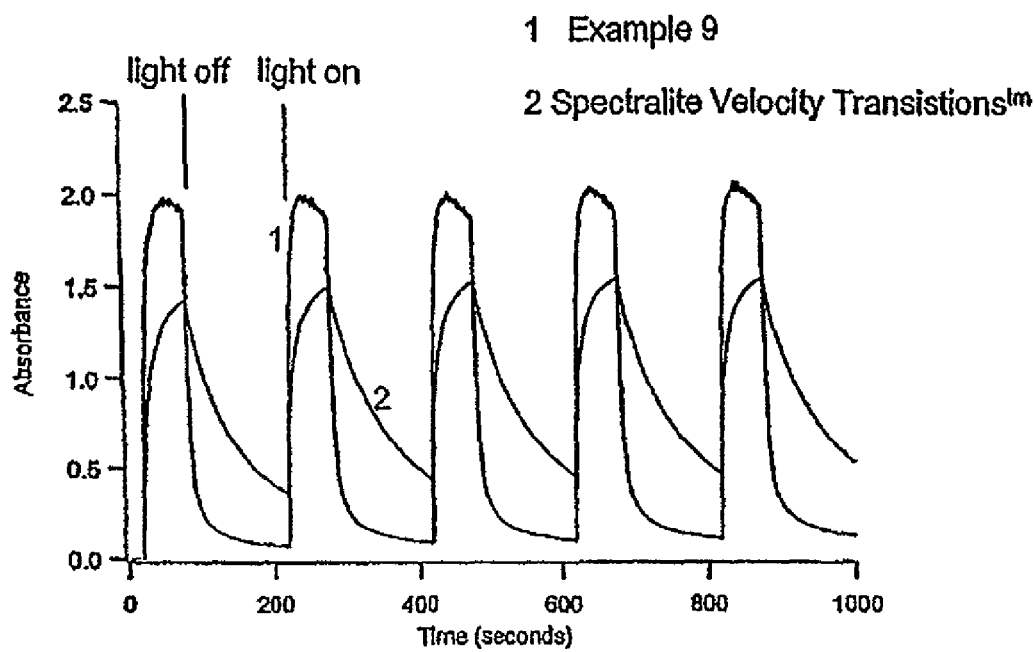
FIG. 16 is an absorbance graph comparing the rate of colouration and fade of the dye of Example 9 with the "Spectrolite Velocity Transitions" product.

It was shown that the oligomer must be attached to the dye for the fast fade effect to occur. Example 5 and CE1 were cast into separate lenses as before. A third test lens containing 1.18 mg CE5 and 1.44 mg of 10 cst PDMS in 1.1321 g of monomer mix A was also prepared. This lens was slightly hazy. It was clearly shown that the dye with the oligomer attached (Ex. 5) showed fast coloration and fade where as both the CE5 and the CE5+PDMS lens showed essentially the same slow kinetics (FIGS. 14 and 15). This also illustrates the great efficiency of the methodology of the attachment of the low Tg oligomer to the dye. Because the dye cannot be separated from its highly localised low Tg environment, very little is needed in the lens. As only small amounts of dye are needed to obtain the photochromic effect logically only a small amount of oligomer are added the formulation. However in order to get improved fade speed with conventional dyes comparatively very large amounts of "soft" monomer need to be added to the bulk host matrix. Thus the bulk mechanical properties of the lens are degraded.

Comparison Between Photochomic Dyes and a Commercial Photochromic Lens.

The improved kinetic performance of these modified photochromic dyes as compared to the state of the art is illustrated in the 16. Example 9 was cast in the monomer mix A (4:1 Nouryset 110:NK ester 9G) and compared to the premium fast fade photochromic lens "Sepctralite Velocity Transtions™". The improvement in performance of the photochromic—PDMS conjugate over the current commercial lens is clear. Example 9 gave near-square wave performance that matched the light on light off cycles and returned to near 0.0 absorbance each cycle. The commercial lens gave a saw tooth response and returned to 0.4 absorbance (ca. 40% transmission) before each next light-on cycle. It must be noted that the host matrix containing example 9 is not optimised for photochromic response where as the commercial lens is. The compounds of this invention represents a significant and large advance on existing technology.

EXAMPLE 25

The imbibition experiment was carried out by contacting the lens sample to the dye of Example 1 and paraffin oil mixture for three hours at 130° C. The lens was then cleaned with acetone when the lens was cooled to room temperature. The lens was photochromic when sufficient dye diffused into the lens.

EXAMPLE 26

Fatigue Resistance Test

The fatigue test was carried out by exposing the lens (made from monomer mix A and the appropriate dye example) sample to an accelerated weathering condition then evaluating the change of lens colour before and after the fatigue. The weathering condition is equivalent to two years actual wearing of the lens in everyday life. The lens samples indoor colour shift and intensity change as well as the activated colour shift and intensity change are used to rate the sample fatigue property. It was shown that the PDMS chain did not significantly degrade photochromic dye fatigue resistance in a ophthalmic lens formulation by comparing results obtained from Example 13 and Comparative Example 6.

The invention claimed is:

1. A photochromic compound which is an adduct comprising a photochromic moiety chemically linked to at least one pendent poly[di-($C_1$ to $C_{10}$ hydrocarbyl) siloxane] oligomer.

2. A photochromic compound according to claim 1 in which the fade half life is reduced by at least 20% compared with the corresponding photochromic compound in absence of the oligomer.

3. A photochromic compound according to claim 2 wherein the fade half life is reduced by at least 40% compared with the corresponding photochromic compound without the oligomer.

4. A photochromic compound according to claim 1 wherein said compound is formed by reaction of a photochromic moiety, optionally comprising a linker group, with a preformed oligomer.

5. A photochromic compound according to claim 1 wherein said compound is formed by growth of an oligomer chain by living polymerization initiated on the photochromic moiety.

6. A photochromic compound comprising a photochromic moiety chemically linked to at least one poly[di-($C_1$ to $C_{10}$ hydrocarbyl) siloxane]oligomer which comprises a combined number of di($C_1$ to $C_{10}$ hydrocarbyl)siloxane monomer units of at least 5.

7. A photochromic compound according to claim 6 having the formula I:

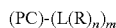   I wherein
PC is a photochromic moiety
L is a bond or linking group;
R is an oligomer chain;
n is an integer from 1 to 3;
m is an integer from 1 to 3; and
R is an oligomer comprising a poly[di-($C_1$ to $C_{10}$ hydrocarbyl) siloxane]
wherein the total number of polydi($C_1$ to $C_{10}$ hydrocarbyl) siloxane monomer units in the oligomer R is at least 5.

8. A photochromic compound according to claim 7 wherein the linking group L and oligomer R provide a longest chain length of at least 12 atoms.

9. A photochromic compound according to claim 7 wherein the longest chain length is at least 15 atoms.

10. A compound according to claim 7 wherein the photochromic moiety (PC) is selected from the group consisting of chromenes, spiropyrans, spiro-oxazines, fulgides, fulgimides, anils, perimidinespirocyclohexadienones, stilbenes, thioindigoids, azo dyes and diarylethenes.

11. A photochromic compound according to claim 7 wherein the photochromic moiety (PC) is selected from the group consisting of naphthopyrans, benzopyrans, indenonaphthopyrans, phenanthropyrans, spiro(benzindoline) naphthopyrans, spiro(indoline)benzopyrans, spiro(indoline) naphthopyrans, spiroquinopyrans, spiro(indoline)pyrans, spiro(indoline)-naphthoxazines, spiro(indoline)pyridobenzoxazines, spiro(benzindoline)pyrido-benzoxazines, spiro (benzindoline)naphthoxazines, spiro(indoline)benzoxazines, fulgides and fulgimides.

12. A photochromic compound according to claim 7 wherein R is an oligomer selected from the group consisting of polydialkylsiloxane oligomers.

13. A photochromic compound according to claim 7 wherein R is a poly[di-($C_1$ to $C_4$ alkyl) siloxane]oligomer.

14. A photochromic compound according to claim 7 wherein R comprises a group of formula I(a)

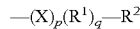

wherein:
X is selected from the group consisting of oxygen, sulfur, amino, $C_1$ and $C_6$ alkyl amino, and $C_1$ to $C_4$ alkylene;
p is 0 or 1;
q is the number of the monomer units; q is at least 5;
$R^1$ is di-($C_1$ to $C_{10}$ hydrocarbyl) siloxane; and
$R^2$ is selected from the group consisting of hydrogen, $C_1$ to $C_6$ alkyl, $C_1$ to $C_6$ haloalkyl, hydroxy, optionally substituted amino, optionally substituted alkyl carboxylic acid, optionally substituted aryl carboxylic acid and derivatives thereof.

15. A photochromic compound according to claim 7 wherein the oligomer R is selected from the group consisting of formula v and vi;

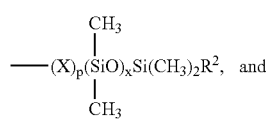

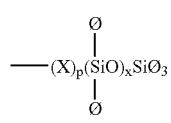

wherein X is selected from the group consisting of oxygen, sulfur, amino and alkylene;
$R^2$ is selected from the group consisting of hydrogen, $C_1$ to $C_6$ alkyl, $C_1$ to $C_6$ haloalkyl, hydroxyl, optionally substituted amino, optionally substituted alkyl carboxylic acid, optionally substituted aryl carboxylic acid and derivatives thereof p is 0 or 1;
x is at least 7 and ø is alkyl or aryl and includes at least a portion of aryl groups.

16. A photochromic compound according to claim 7 wherein the oligomer R is linked to the photochromic moiety (PC) by a linker group of at least one of the formulae selected from IIa to IIk:

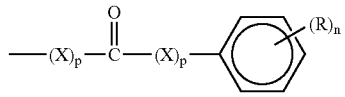

IIa

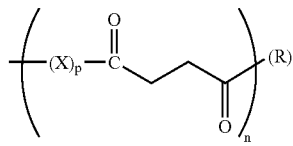

IIb

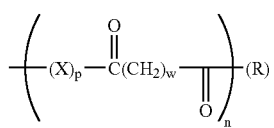

IIc

IId

IIe

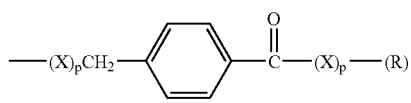

IIf

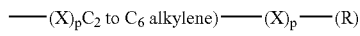

IIg

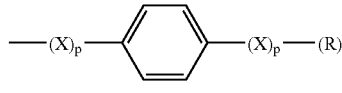

IIh

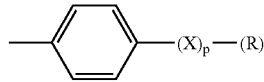

IIi

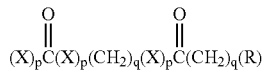

IIj

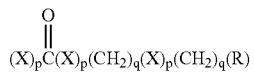

IIk wherein in the formula IIa to IIk:
X which may be the same or different is selected from the group consisting of oxygen, sulphur, amino and alkylene;
$R^4$ is selected from the group consisting of hydroxy, alkoxy, amino and substituted amino;
n is an integer from to to 3;
w is an integer from 1 to 4;
q is an integer from 0 to 15;
p which when there is more than one may be the same or different is 0 or 1; and
(R) shows the radial for attachment of oligomer R.

17. A photochromic compound according to claim 7 wherein the photochromic moiety (PC) is selected from the group consisting of chromenes, spirooxazines, fulgides; fulgimides, azo dyes and diarylethenes.

18. A photochromic compound according to claim 7 wherein the photochromic moiety (PC) is selected from the group consisting of:

(a) spiro-oxazines of formula III

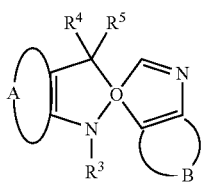

III in the general formula III, $R^3$, $R^4$ and $R^5$ may be the same or different and are each selected from the group consisting of an alkyl group, a cycloalkyl group, a cycloarylalkyl group, an alkoxy group, an alklyleneoxyalkyl group, an alkoxycarbonyl group, a cyano, an alkoxycarbonylalkyl group, an aryl group, an arylalkyl group, an aryloxy group, an alkylenethioalkyl group, an acyl group, an acyloxy group and an amino group, $R^4$ and $R^5$ may together form a ring, and $R^3$, $R^4$ and $R^5$ may optionally each have a substituent(s); and the group represented by moiety IIIa

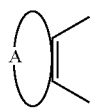

IIIa is a substituted or unsubstituted bivalent aromatic hydrocarbon group or a substituted or unsubstituted bivalentunsaturated heterocyclic group and the group represented by moiety IIIb:

IIIb is a substituted or unsubstituted bivalent aromatic hydrocarbon group or a substituted or unsubstituted bivalent unsaturated heterocyclic group;

(b) chromenes of formula XX

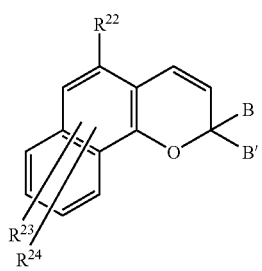

XX wherein

B and B' are independently selected from optionally substituted aryl and heteroaryl; and $R^{22}$, $R^{23}$ and $R^{24}$ are independently selected from the group consisting of hydrogen; halogen; $C_1$ to $C_3$ alkyl; the group $L(R)_n$; and the group of formula COW wherein W is $OR^{25}$, $NR^{26}R^{27}$, piperidino or morpholino wherein $R^{25}$ is selected from the group consisting of $C_1$ to $C_6$ alkyl, phenyl, ($C_1$ to $C_6$ alkyl)phenyl, $C_1$ to $C_6$ alkoxyphenyl, phenyl $C_1$ to $C_6$ alkyl [($C_1$ to $C_6$ alkoxy)phenyl], $C_1$ to $C_6$ alkoxy $C_2$ to $C_4$ alkyl and the group $L(R)_n$; $R_{26}$ and $R_{27}$ are each selected from the group consisting of $C_1$ to $C_6$ alkyl, $C_5$ to $C_7$ cycloalkyl, phenyl, phenyl substituted with one or two groups selected from $C_1$ to $C_6$ alkyl and $C_1$ to $C_6$ alkoxy and the group $L(R)_n$; $R^{22}$ and $R^{23}$ may optionally form a carboxylic ring of 5 or 6 ring members optionally fused with an optionally substituted benzene and wherein at least one of the substituents is selected from the group of substituents consisting of B and B', $R^{22}$, $R^{23}$, $R^{24}$, $R^{25}$, $R^{26}$ and $R^{27}$ is the group $L(R)_n$;

(c) fulgides and fulgimides of formula XXX:

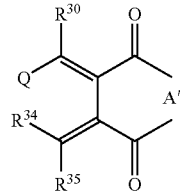

XXX wherein

Q is selected from the group consisting of optionally substituted aromatic, optionally substituted heteroaromatic; where said aromatic/heteroaromatic may be mono or polycyclic aromatic/heteroaromatic;

$R^{30}$ is selected from the group consisting of a $C_1$ to $C_4$ alkyl, $C_1$ to $C_4$ alkoxy phenyl, phenoxy mono- and di($C_1$-$C_4$) alkyl substituted phenyl or phen($C_1$ to $C_4$) alkyl;

A' is selected from the group consisting of oxygen or =N—$R^{36}$, in which $R^{36}$ is $C_1$-$C_4$ alkyl or optionally substituted phenyl, $R^{34}$ and $R^{35}$ independently represents a $C_1$ to $C_4$ alkyl, phenyl or phen($C_1$ to $C_4$) alkyl or one of and $R^{34}$, $R^{35}$ is hydrogen and the other is one of the aforementioned groups selected from $C_1$ to $C_4$ alkyl, phenyl or phen($C_1$ to $C_4$) alkyl, or $R^{34}R^{35}$=represents an adamantylidine group; and wherein at least one of Q, $R^{30}$, $R^{34}$, $R^{35}$ and $R^{36}$ comprises the group $L(R)_n$; and (d) azo dyes of formula XL

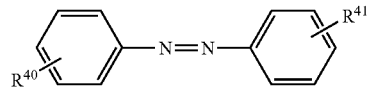

XL wherein:

$R^{40}$ and $R^{41}$ are independently selected from the group consisting of hydrogen; $C_1$ to $C_6$ alkyl; $C_1$ to $C_6$ alkoxy; —$NR^{42}R^{43}$ wherein $R^{42}$ and $R^{43}$ are as defined for $R^{26}$ and $R^{27}$; aryl, aryl substituted with one or more substituents selected from $C_1$ to $C_6$ alkyl and $C_1$ to $C_6$ alkoxy, substituted $C_1$ to $C_6$ alkyl wherein the substituent is selected from aryl and $C_1$ to $C_6$ alkoxy, substituted $C_1$ to $C_6$ alkoxy wherein the substituent is selected from $C_1$ to $C_6$ alkoxy, aryl and aryloxy.

19. A photochromic article comprising a photochromic compound of claim 6.

20. A photochromic article according to claim 19 selected from optical lenses, face shields, goggles, visors, camera lenses, windows, automotive windshields, aircraft and automotive transparencies, plastic films and sheets, textiles and coatings, and inks.

21. A method of preparing a photochromic compound comprising reacting a photochromic moiety with an oligomer to provide a photochromic compound which is an adduct comprising a photochromic moiety chemically linked to at least one pendent poly[di-($C_1$ to $C_{10}$ hydrocarbyl) siloxane] oligomer.

22. A compound according to claim 7 of formula:

$$(PC)\text{-}(L(R)_n)_m$$

wherein PC is a photochromic moiety selected from the group consisting of chromenes, spiropyrans and spirooxazines and the group $(L(R)_n)_m$ is polydimethyl siloxane propyl ethoxy succinyl.

\* \* \* \* \*